United States Patent [19]

Walser et al.

[11] 4,349,476
[45] Sep. 14, 1982

[54] PROCESS FOR PRODUCING IMIDAZODIAZEPINES

[75] Inventors: Armin Walser, West Caldwell; Rodney I. Fryer, North Caldwell, both of N.J.

[73] Assignee: Hoffmann-La Roche Inc., Nutley, N.J.

[21] Appl. No.: 242,946

[22] Filed: Mar. 12, 1981

Related U.S. Application Data

[60] Division of Ser. No. 905,820, May 15, 1978, Pat. No. 4,280,957, which is a continuation of Ser. No. 663,660, Mar. 4, 1978, abandoned, which is a continuation-in-part of Ser. No. 602,691, Aug. 7, 1975, abandoned, which is a continuation-in-part of Ser. No. 504,924, Sep. 11, 1974, abandoned.

[51] Int. Cl.³ .................... C07D 487/04; C07D 487/14
[52] U.S. Cl. .......................... 260/244.4; 260/239 BC; 260/239 BD; 260/245.6
[58] Field of Search ........................... 260/244.4, 245.6; 544/250, 281; 548/324

[56] References Cited

U.S. PATENT DOCUMENTS

| | | | |
|---|---|---|---|
| 3,597,422 | 8/1971 | Winn | 548/324 X |
| 3,600,390 | 8/1971 | Sherlock | 544/250 |
| 3,823,157 | 7/1974 | De Wald et al. | 260/245.6 |
| 3,850,956 | 11/1974 | van der Burg | 260/245.6 |
| 3,910,946 | 10/1975 | Gall | 260/245.6 |
| 4,005,099 | 1/1977 | Gall | 260/245.6 X |
| 4,247,463 | 1/1981 | Walser | 260/245.6 |

OTHER PUBLICATIONS

Fryer, et al., J. Heterocyclic Chemistry, vol. 15, pp. 619-624 (6/78).

Primary Examiner—Donald G. Daus
Assistant Examiner—Diana G. Rivers
Attorney, Agent, or Firm—Jon S. Saxe; Bernard S. Leon; Frank P. Hoffman

[57] ABSTRACT

This invention is directed toward pharmacologically active compound of the formula wherein A is $-\underset{R_6}{C}=N$ ;

$R_1$ is selected from the group consisting of hydrogen, lower alkyl, hydroxy lower alkyl, acyloxy lower alkyl, phenyl, alkoxy lower alkyl, halo lower alkyl, amino lower alkyl, substituted amino lower alkyl, substituted phenyl, pyridyl, aralkyl and the groups $\underset{RCO}{|}$ wherein R is hydrogen or lower alkyl and ROOC where R is lower alkyl; $R_2$ is selected from the group consisting of hydrogen, lower alkyl, hydroxy lower alkyl, acyloxy lower alkyl, alkoxy lower alkyl, halo lower alkyl, amino or substituted amino lower alkyl, amino, cyano, cyano lower alkyl, substituted amino, chloro, bromo and iodo, the group —COOR where R is hydrogen or lower alkyl, the group $\underset{RCO}{|}$ where R is hydrogen or lower alkyl, or derivatives thereof, e.g., the group R—C=N—R' wherein R' is hydrogen, lower alkyl, hydroxy, phenyl, alkoxy, amino, mono or di-alkylamino and arylamino and R is hydrogen or lower alkyl, the group $-\text{CON}\underset{R'}{\overset{R}{\diagup}}$ (where R and R' are individually hydrogen, lower alkyl, hydroxy lower alkyl, lower alkenyl, aryl or together R and R' form a part of a heterocyclic ring and the group $(CH_2)_n NRR'$ where R and R' are hydrogen, lower alkyl, hydroxy lower alkyl, lower alkenyl or together R and R' form a part of a heterocyclic ring and n is 1 to 4); the group $-\text{CONN}\underset{R^{12}}{\overset{R^{10}\ R^{11}}{\diagup}}$ where $R^{10}$, $R^{11}$, $R^{12}$ are hydrogen or lower alkyl and the group $(CH_2)_n NR^{13}R^{14}$ where n is 1 to 4 and $R^{13}$, $R^{14}$ are hydrogen, lower alkyl, hydroxy lower alkyl, lower alkenyl or $R^{13}$ and $R^{14}$ together form part of a heterocyclic ring, with the limitation that where $R^{10}$, $R^{11}$ or $R^{12}$ is a basic side chain, then the remaining substituents are hydrogen or lower alkyl; $R_3$ is selected from the group consisting of hydrogen and lower alkyl;

$R_5$ is selected from the group consisting of hydrogen, lower alkanoyloxy and hydroxy; $R_4$ is selected from the group consisting of hydrogen, halogen, nitro, cyano, trifluoromethyl, lower alkyl, substituted amino, amino, hydroxy lower alkyl and lower alkanoyl; $R_6$ is selected from the group consisting of phenyl, mono-substituted phenyl, di-substituted phenyl, pyridyl and mono-substituted pyridyl; and

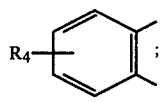 ; 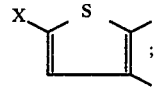 ; 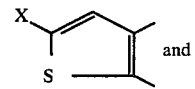

wherein X is chlorine, bromine iodine or hydrogen wherein X is chlorine bromine, iodine or hydrogen

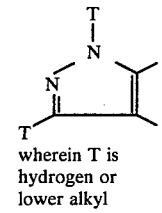

wherein T is hydrogen or lower alkyl

is selected from the group consisting of and the pharmaceutically acceptable salts thereof.

Also provided are methods for the preparation of these compounds as well as pharmaceutical formulations which contain the active compounds of this invention. The compounds of the formulas illustrated above and their analogs are useful as anticonvulsants, muscle relaxants, anxiolytic and sedative agents.

1 Claim, No Drawings

PROCESS FOR PRODUCING IMIDAZODIAZEPINES

This is a division of application Ser. No. 905,820 filed May 15, 1978, now U.S. Pat. No. 4,280,957 which is a continuation of Ser. No. 663,660, filed Mar. 4, 1978 (now abandoned) which is a CIP of Ser. No. 602,691, filed Aug. 7, 1975 (now abandoned) which is a CIP of Ser. No. 504,924, filed Sept. 11, 1974 (now abandoned).

DESCRIPTION OF THE INVENTION

This invention relates to the pharmacologically active imidazo[1,5-a][1,4]diazepine compounds series. The chemical structure of these compounds may be depicted by the following formula:

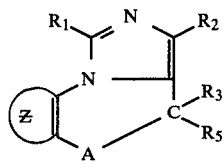

wherein A is

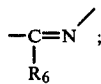

$R_1$ is selected from the group consisting of hydrogen, lower alkyl, hydroxy lower alkyl, acyloxy lower alkyl, phenyl, alkoxy lower alkyl, halo lower alkyl, amino lower alkyl, substituted amino lower alkyl, substituted phenyl, pyridyl, aralkyl and the groups

wherein R is hydrogen or lower alkyl; and ROOC where R is lower alkyl; $R_2$ is selected from the group consisting of hydrogen, lower alkyl, hydroxy lower alkyl, acyloxy lower alkyl, alkoxy lower alkyl, halo lower alkyl, amino lower alkyl, amino, cyano, cyano lower alkyl, substituted amino, chloro, bromo or iodo, substituted amino lower alkyl, the group ROOC where R is hydrogen or lower alkyl, the group

where R is hydrogen or lower alkyl, or derivatives thereof, i.e., the group

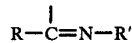

wherein R' is hydrogen, lower alkyl, hydroxy, phenyl, alkoxy, amino, mono or di-alkylamino and arylamino and R is hydrogen or lower alkyl, the group

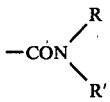

(where R, R' are individually hydrogen, lower alkyl, hydroxy lower alkyl, lower alkenyl, aryl or together R and R' form a part of a heterocyclic ring and the group $(CH_2)_n NRR'$ where R and R' are hydrogen, lower alkyl, hydroxy lower alkyl, lower alkenyl or together R and R' form a part of a heterocyclic ring and n is 1 to 4); the group

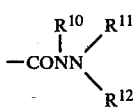

where $R^{10}$, $R^{11}$, and $R^{12}$ are hydrogen are hydrogen or lower alkyl and the group $(CH_2)_2 NR^{13}R^{14}$ where n is 1 to 4 and $R^{13}$, $R^{14}$ are hydrogen, lower alkyl, hydroxy lower alkyl, lower alkenyl or $R^{13}$ and $R^{14}$ together form part of a heterocyclic ring, with the limitation that where $R^{10}$, $R^{11}$ or $R^{12}$ is a basic side chain, then the remaining substituents are hydrogen or lower alkyl; $R_3$ is selected from the group consisting of hydrogen and lower alkyl; $R_5$ is selected from the group consisting of alkanoyloxy, hydroxy or hydrogen; $R_4$ is selected from the group consisting of hydrogen, halogen, nitro, cyano, trifluoromethyl, lowr alkyl, substituted amino, amino, hydroxy lower alkyl and lower alkanoyl; $R_6$ is selected from the group consisting of phenyl, monosubstituted phenyl, di-substituted phenyl, pyridyl and mono-substituted pyridyl; and

is selected from the group consisting of

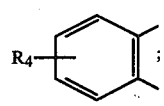 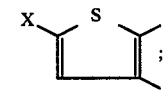 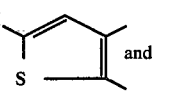

wherein X is chlorine bromine, iodine or hydrogen wherein X is chlorine, bromine, iodine or hydrogen

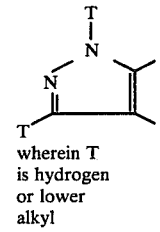

wherein T is hydrogen or lower alkyl and the pharmaceutically acceptable salts thereof.

Various analogous compounds derived from the above compounds, together with various novel intermediates leading to the above compounds, are also considered to be within the scope of the invention and exhibit pharmacological activity per se or are useful intermediates to pharmacologically active compounds.

Analogs of the above compounds which form a part of this invention include compounds of the formula

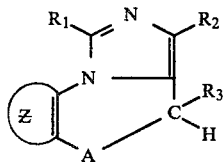

IA wherein

A is selected from the group consisting of

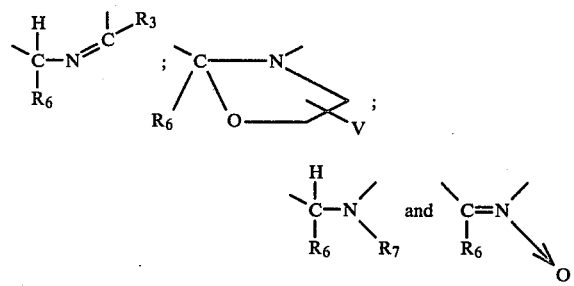

wherein
V = hydrogen or lower alkyl
$R_1$, $R_2$, $R_6$ and

are in Formula I above, $R_7$ is selected from the group consisting of hydrogen, lowr alkyl, lower alkenyl, lower alkynyl, acyl, hydroxy, nitroso, aromatic and aliphatic sulfonyl groups and lower alkoxycarbonyl; and $R_3$ is hydrogen or lower alkyl and the pharmaceutically acceptable salts thereof.

As used in this disclosure, the term "lower alkyl" or "alkyl" comprehends both straight cyclo and branched chain ($C_1$–$C_7$) carbon-hydrogen radicals, preferably $C_1$–$C_4$ carbon-hydrogen radicals such as methyl, ethyl, propyl, isopropyl, butyl and the like.

By the term "lower alkanoyl" or "acyl" as utilized herein, an acyl moiety of a $C_1$–$C_7$ preferably a $C_1$–$C_4$ alkanoic acid is intended, e.g., acetyl, propionyl, butyryl and the like, i.e., moieties of the formula

wherein $R^{20}$ is $C_1$–$C_6$ or hydrogen. Also as utilized herein, the term "lower alkanoyl" comprehends a protected carbonyl such as an acetal or ketal having 2 to 7 carbon atoms, e.g., a group of the formula

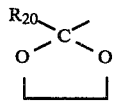

wherein $R^{20}$ is $C_1$–$C_6$ or hydrogen. The ketal or aldehyde protecting group is utilized to prevent conversion of the contained ketone or aldehyde

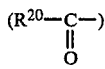

in oxidation, reduction and condensation reactions.

The term "halogen" is used to include all four forms thereof, i.e., chlorine, bromine, fluorine and iodine.

The terms "aromatic and aliphatic sulfonyl grouping" comprehends compounds of the formula $SO_2X$ wherein X is a branched or straight chain $C_1$–$C_7$, preferably $C_1$–$C_4$ aliphatic group e.g., methyl or a substituted or unsubstituted aromatic group such as a phenyl or substituted phenyl derivative e.g., tolyl.

The $R_6$ phenyl moiety may be mono- or di-substituted provided that such di-substitution occurs in the 2,3; 2,5; or, most preferably, in the 2,6 position of the phenyl moiety. Suitable mono-substituents include halogen and nitro and preferably are substituted in the 2-position of the phenyl moiety. Suitable di-substituents are 2,6 or 2,5 di-halogen and 2,6 or 2,5 halogen-nitro. In the case of mono-substituted pyridyl, suitable substituents include halogen and nitro.

In the case of differently substituted $R_3$ and $R_5$ substituents, optical isomerism will occur and such optical antipodes and racemates are within the ambit of this invention.

By the term "aryl" is meant a substituted or unsubstituted monocyclic aromatic moiety such as phenyl, chlorophenyl, tolyl, and the like. When various moieties are set herein to form a part of a heterocyclic ring, it is intended that the moieties, together with the nitrogen atom to which they are attached form, preferably, a 5 or 6 membered ring which contains at the most one additional hetero atom, preferably nitrogen or oxygen as the hetero atom. Thus, by the heterocyclic ring, there is intended such moieties as morpholino, piperazino, piperidino and pyrrolidino.

By the term "alkoxy" is meant straight or branched chain saturated hydrocarbonoxy group containing from 1 to 7 carbon atoms, preferably from 1 to 4 carbon atoms, such as methoxy, ethoxy, propoxy and the like.

By the term "lower alkenyl" herein is meant straight or branched chain hydrocarbon groups which contain an olefinic double bond and have from 2 to 10, preferably 2 to 6 carbon atoms, i.e., the radical of compounds of the formula $C_nH_{2n}$ wherein n is 2–10, e.g., allyl.

By the term "substituted amino" herein is meant an —$NH_2$ group which may be mono or disubstituted by lower alkyl, e.g., methylamino or dimethylamino groups or an acyl amino group e.g., acetamino which may then be substituted on the nitrogen atom by lower alkyl or aryl e.g., methyl, phenyl or tolyl groups or substituted carbonyloxy i.e., COOR where R is lower alkyl or aralkyl, e.g., benzyl.

By the term "aralkyl" is meant a hydrocarbon group having both aromatic and aliphatic structures, that is, a hydrocarbon group in which a lower alkyl H atom is substituted by a monocyclic aryl group, e.g., phenyl, tolyl and the like.

Preferred compounds encompassed by the present invention include those wherein $R_1$ is hydrogen or lower alkyl, preferably methyl; $R_3$ and $R_5$ are hydrogen

is

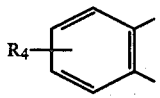

wherein R₄ is located preferably in the 8-position of the imidazobenzodiazepine molecule and is hydrogen, nitro and halogen, preferably halogen; A is

wherein $R_6$ is phenyl or halo, nitro or lower alkyl substituted phenyl, preferably halo substituted preferably in the 2-position of the phenyl moiety and $R_2$ is selected from the group consisting of hydrogen, lower alkyl, hydroxy lower alkyl, e.g., hydroxy methyl, carboxylic acid hydrazide i.e., a group of the formula —CONHNH₂ and carboxamide, i.e., a group of the formula —CONH₂ e.g., compounds of the formula

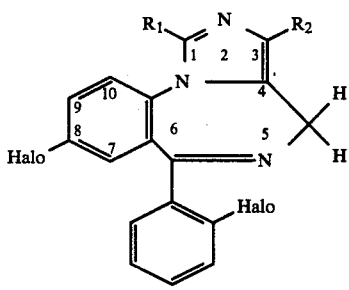

IB

Thus, it is apparent from the above, an especially preferred genus included within the perview of the present invention encompasses a compound of the formula

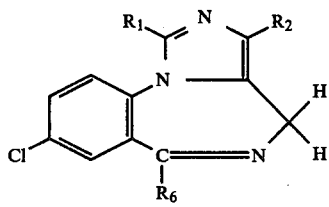

IC wherein $R_1$ is hydrogen and lower alkyl preferably methyl; $R_3$ and $R_5$ are hydrogen; $R_4$ is hydrogen, nitro and halogen, most preferably, chlorine, and in a most preferred embodiment when positioned on the fused benzo portion of the imidazobenzodiazepine is in the 8-position thereof, $R_6$ is phenyl or halo, nitro, or lower alkyl-substituted phenyl, Preferably, halo, with fluorine being the preferred halogen, the substituted fluoro being positioned in the 2-position of the phenyl moiety and $R_2$ is hydrogen and lower alkyl.

Another preferred class of compounds falling within the scope of formula I are those wherein $R_1$, $R_2$, $R_4$, $R_5$, $R_6$ and A are as in Formula IC above and $R_3$ is lower alkyl, preferably methyl, i.e., compounds of the formula

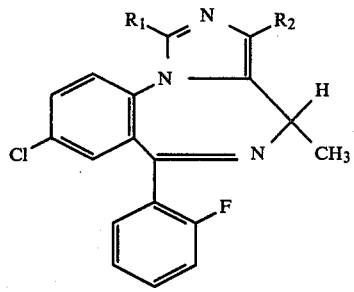

ID

Compounds of formula ID and their pharmaceutically acceptable salts exhibit optical isomerism. Such a compound (ID) where $R_5$=H and $R_3$=CH₃ has been resolved into its optical enantiomers by a procedure similar to the one generally outlined in *Advanced Organic Chemistry*, L. Fieser and M. Fieser, 1961, pp. 85–88, Rheinhold Publishing Co. Both the optical isomers and the racemic form of compound ID exhibit pharmacological activity. For example, in the case of the tartrate salt of compounds of formula ID the (+) isomer is considerably more active than the (−) isomer. The less active (−) isomer may, if desired, be converted to the active racemic form thereof such as by treatment with a non-aqueous base, e.g., sodium tertiary butoxide in the presence of an organic solvent in which the isomer is soluble.

A further preferred group of compounds are those of formula I wherein

is an 8-chlorophenyl or an 8-chlorothieno [3,2-f] group, $R_1$ is hydrogen or methyl, $R_2$ is acetyl, carboxamido or dimethylcarboxamido, $R_6$ is 2-fluoro- or 2-chlorophenyl and $R_3$ and $R_5$ are hydrogen.

The expression "pharmaceutically acceptable salts," is used to include salts with both inorganic and organic pharmaceutically acceptable acids such as hydrochloric acid, hydrobromic acid, nitric acid, sulfuric acid, phosphoric acid, citric acid, formic acid, maleic acid, acetic acid, succinic acid, tartaric acid, methanesulfonic acid, para toluenesulfonic acid and the like. Such salts can be formed quite readily by those skilled in the art, with the prior art and the nature of the compound to be placed in salt form, in view.

The most preferred pharmaceutically acceptable acid addition salts of the compounds of formula IC and ID respectively are:

8-chloro-6-(2-fluorophenyl)-1-methyl-4H-imidazo [1,5-a][1,4]benzodiazepine maleate;

8-chloro-1,4-dimethyl-6-(2-fluorophenyl)-4H-imidazo[1,5-a][1,4]benzodiazepine maleate.

Also within the ambit of the instant invention are compounds which are obtained by ring opening of formula I compounds. Such compounds are of the formula

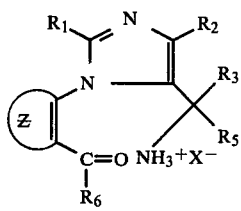

wherein $X^-$ is the anion of an organic or inorganic acid, and $R_1$, $R_2$, $R_3$, $R_4$, $R_5$, $R_6$ and

are as in formula I. It has been found that certain compounds of Formula I in solution open to corresponding compounds of Formula IE. Such open compounds exist in a pH-dependent equilibrium in solution with compounds of Formula I, i.e., their corresponding ring closed compounds. The compounds of Formula IE can be isolated as acid addition salts by treatment of their corresponding closed ring compounds with an aqueous mineral acid followed by evaporation of solvent. When isolated, these salts exhibit pharmacological activity comparable to their corresponding closed ring parents.

The compounds of formula I above including the preferred imidazobenzodiazepines of formulas IC and ID can be prepared following a variety of synthetic routes including the following novel process aspects which form a part of the present invention.

In one of the aforementioned novel process aspects of this invention, the compounds of formula I above may be prepared by the nitrosation of a compound of the formula

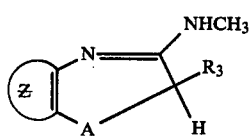

wherein A is

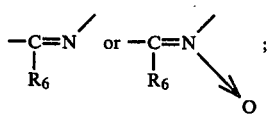

$R_3$ is hydrogen or lower alkyl and

$R_4$ and $R_6$ are as described in Formula I, to produce a compound of the formula

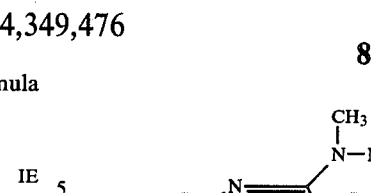

wherein A, $R_3$, $R_4$, $R_6$ and

are as described in Formula II.

Such a nitrosation may be affected by "in situ formed" nitrous acid. Reagents which may be employed include (1) alkali metal nitrites, i.e., sodium nitrites, in the presence of organic or inorganic acids, i.e., glacial acetic acid, and aqueous or non-aqueous solvents; (2) alkyl nitrites, i.e., methyl nitrites, in the presence of an inert solvent such as alcohol, chlorinated hydrocarbon or, for example, dimethylformamide; and (3) a nitrosyl chloride gaseous solution in an inert solvent and in the presence of an acid acceptor such as pyridine. Such a nitrosation reaction should be affected at around or below room temperature, i.e., in the range of $-20°$ C. to $25°$ C.

The 2-position nitrosoalkylamine, e.g.,

represents a "leaving group." Equivalent leaving groups which may be utilized as 2-position substituents include groups such as alkoxide, e.g., $-OCH_3$; alkylthio, e.g., $-SCH_3$; halo, e.g., chloro; cyano, e.g., $-CN$, and phosphate, e.g.,

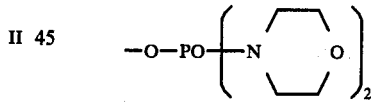

Reactions which form the alkoxide and alkylthio 2-position substituents are well known in the art; see, for example, G. A. Archer and L. H. Sternbach, *Journal of Organic Chemistry*, 29, 231 (1964) and U.S. Pat. No. 3,681,341, issued Aug. 1, 1972 to Fryer et al.

Compounds of formula III may then be condensed with a nitroalkane to form a novel intermediate of the formula

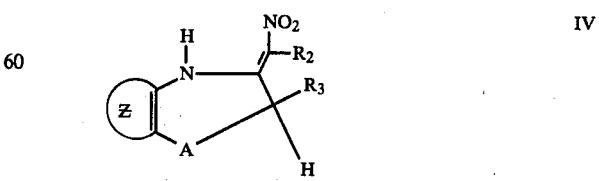

wherein $R_2$ is hydrogen or lower alkyl, A, $R_3$, $R_4$, $R_6$ and are as described in Formula II The condensation reaction is affected with a nitroalkane, ($R_2$—$CH_2$—$NO_2$), where $R_2$ is hydrogen or lower alkyl, i.e., nitromethane, nitroethane, etc., in the presence of a base which is strong enough to generate the nitroalkane anion. Suitable bases include the alkali metal or alkaline earth metal alkoxides, e.g., potassium tertiary butoxide, amides, e.g., lithium amide or hydrides, e.g., sodium hydride. The reaction is preferably carried out in an inert solvent, such as dimethylformamide, dimethylsulfoxide, or an ether, e.g., THF, at temperatures below or above room temperature, i.e., in the range of −50° C. to 150° C., preferably at about room temperature.

The novel compounds of formula IV and formula V below, besides being major intermediates in the synthesis of compounds of formula I, also exhibit activity as central nervous system depressants.

Compounds of formula IV may then be catalytically hydrogenated, for example, with Raney nickel in the presence of hydrogen or by other reductants such as lithium aluminum hydride (with limitation that A is not N-oxide) to produce a compound of the formula

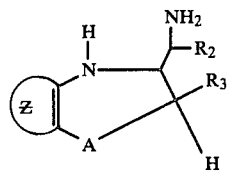
V wherein A is

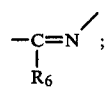

$R_3$, $R_4$,

and $R_6$ are as in Formula II except that $R_4$ is not nitro or cyano, and $R_6$ is not nitro substituted and $R_2$ is hydrogen or lower alkyl.

The exclusion of nitro and cyano above from the substituent groups present results from the conversion of nitro into amino and cyano into methylamino under the reaction conditions employed in the step IV→V.

Solvents suitable for hydrogenation with Raney nickel include alcohols, e.g., ethanol, ethers, e.g., THF, diethylether, etc., hydrocarbon solvents, e.g., toluene and dimethylformamide. The reaction temperature may be above or below room temperature (i.e., −50° C. to 150° C.) and the reaction may be carried out with or without pressure, i.e., pressure of one atmosphere or higher.

Solvents suitable for hydrogenation employing a reductant such as lithium aluminum hydride include ethers, e.g., THF, dioxane, diethylether and mixtures of ethers and hydrocarbon solvents, e.g., THF and benzene. The reaction may be carried out from below room temperature to reflux temperature, i.e., preferably in the range of −50° C. to 60° C.

The compounds of formula V may then be acylated with an acylating agent such as an acid halide or acid anhydride, i.e., a group of the formula ($R_1CO)_2O$ wherein $R_1$ is hydrogen, lower alkyl, phenyl, pyridyl, substituted phenyl, alkoxy lower alkyl and aralkyl, e.g., acetic anhydride and acetyl chloride to produce a compound of the formula

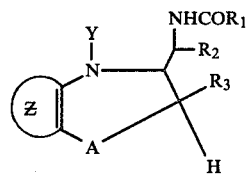
VI wherein A, $R_2$, $R_3$, $R_4$,

are as described in Formula V, $R_1$ is hydrogen, lower alkyl, phenyl, pyridyl, substituted phenyl, alkoxy lower alkyl and aralky and Y is hydrogen or —$COR_1$.

In acylating the compounds of formula V to compounds of formula VI, there may be present a mixture consisting of the predominant monoacylated product, i.e., wherein the $NH_2$ group of V (position 2) is converted to $NHCOR_1$, and the diacylated product wherein both the $NH_2$ of V (position 2 ) and 1-position nitrogen are acylated. The yield of diacylated product may be increased by subjecting the compounds of formula V to more rigorous conditions, i.e., excess of acylating agent and increased reaction time. It should be noted where any of the substituents may be hydroxy lower alkyl that this substituent should be protected by, for example, esterification a subsequent mild hydrolysis will reconvert the protected substituent to the original substituent.

The acylation is preferably carried out in the presence of an aqueous or non-aqueous solvent e.g., water, methylene chloride, benzene, chloroform, etc., and preferably with an acid acceptor such as an organic or inorganic base such as triethylamine, pyridine or an alkali metal carbonate. The compounds of formula VI may then be cyclized to novel compounds of the formula

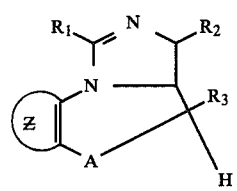
VII wherein A, $R_1$, $R_2$, $R_3$, $R_4$ and

are as described in formula VI.

The cyclization reaction is affected with a dehydrating agent such as phosphorus pentoxide, polyphosphoric acid or other suitable acid catalysts, i.e., organic or inorganic acids, e.g., conc. H2SO4. A solvent is not required but a solvent such as an aromatic hydrocarbon solvent, e.g., toluene, xylene, may be employed. The reaction is carried out at a temperature range of from about 100° C. to 200° C.

The compounds of formula V may also be reacted with an acylating agent such as an orthoester, e.g., triethylorthoacetate, an orthoamide, e.g., the dimethylacetal of N,N-dimethylformamide, or a compound of the formula

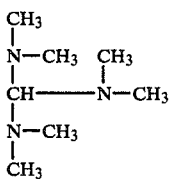

optionally in the presence of an acid catalyst, e.g., an organic or inorganic acid, e.g., p-toluene sulfonic acid, phosphoric acid, etc., and at room temperature or above, i.e., 25° C. to 150° C., in which instance the cyclization to compound VII occurs spontaneously. Other useful acylating agents include esters, e.g., methyl acetate; amidines, e.g., acetamidine; nitriles, e.g., acetonitrile and ester imidates, e.g., a compound of the formula

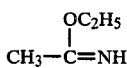

The compounds of formula VII may then be dehydrogenated to yield compounds of the formula

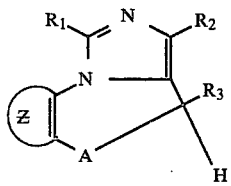 IF wherein A, $R_1$, $R_2$, $R_3$, $R_4$ and

are as described in formula VI.

Preferred reactants for the dehydrogenation (VI→VII) include manganese dioxide and palladium on carbon although potassium permanganate may also be utilized. Solvents which may be utilized include chlorinated hydrocarbon solvents, aromatic hydrocarbons, dimethylformamide, etc. The dehydrogenation is carried out at room temperature or above, i.e., in the range of about 25° C. to 200° C.

The novel compounds of formula VII also exhibit activity as central nervous depressants and form part of this invention.

The above novel process may proceed, if desired, from intermediate compounds IV or V to compounds of formula IF without the requirement of isolating any formed intermediate compounds before proceeding to the next process step.

It should be noted in acylating the compounds of Formula V to the compounds of Formula VI when $R_4$ is amino or alkyl amino that the amino may also be acylated to acylamino. The acylamino may be converted back to amino or alkylamino by subjecting the compounds of Formula VII or IF to a mild hydrolysis.

Also within the ambit of this invention, it has been found that compounds of the formulas IV, V, VI and VII may exhibit both optical and geometric isomerism.

The reaction of a compound of the formula V with acetic acid and zinc or any other suitable reductants e.g., hydrogen in the presence of a catalyst e.g., platinum in dilute acetic acid solution, produces a compound of the formula

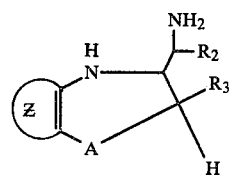 V' wherein A is

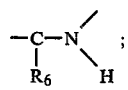

$R_2$, $R_3$, $R_4$,

and $R_6$ are as in formula V.

Depending on the above method of reduction chosen, formula V' when $R_2$ is hydrogen can be isolated as a recemic mixture of either of the two possible diastereomers.

A compound of the formula V' may be converted to its dihydimidazo derivative of the formula

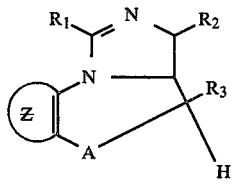 VII' wherein A, $R_2$, $R_3$, $R_4$ and

are as in formula V' and $R_1$ is as in formula VI with retention of stereochemistry, by utilizing the direct reaction set forth above, i.e., the reaction of formula V compounds with an acylating agent such as an orthoester e.g., triethylorthoacetate and maintaining the reaction parameters set forth above for such a reaction.

Compounds of formula VII' can also be prepared by reduction of a compound of formula VII by utilizing reductants as mentioned above e.g., acetic acid and zinc or H₂/platinum catalyst in dilute acetic acid, with the particular stereoisomer produced dependent on the reductant chosen.

Compounds of the formula VII' can, if desired, be oxidized directly to analogous compounds of the formula I using an oxidant such as manganese dioxide in toluene or benzene solution. Reaction conditions utilized and various alternate useful oxidants are found in U.S. Pat. No. 3,322,753 issued May 30, 1967 to Fryer et al.

Another process to produce the novel intermediates of formula V where R₄ and R₆ are other than nitro or cyano consists of the reduction of compounds of the formula

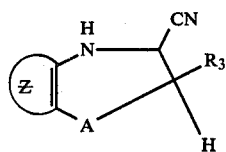                                X wherein A is

$-C=N\diagup$
$\ \ |$
$\ R_6$ and $R_3$, $R_4$,

and $R_6$ are as described in formula II except that $R_4$ is not nitro or cyano and $R_6$ is not nitro-substituted.

The reduction comprises the reaction of the compounds of formula X with a known reductant such as Raney nickel in the presence of hydrogen or by other reductants such as lithium aluminum hydride. Solvents suitable for hydrogenation with Raney nickel include alcohols e.g., ethanol ethers e.g., THF, hydrocarbon solvents e.g., toluene, and dimethylformamide. The reaction temperature may be above or below room temperature (i.e., −50° C. to 150° C.) and the reaction may be carried out with or without pressure, i.e., pressure of one atmosphere or higher.

Solvents suitable for hydrogenation employing a reductant such as lithium aluminum hydride include ethers, such as dioxane, diethyl ether and THF. The reaction may be carried out from below room temperature to reflux temperature i.e., preferably in the range of −50° C. to 60° C.

A variation of the above process comprises a mild acid hudrolysis of the compounds of formula X to produce compounds of the formula

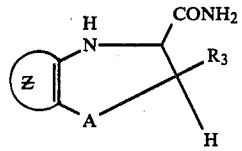                                XI wherein A, R₄, R₃,

and $R_6$ are as in formula X.

The mild acid hydrolysis is suitably affected by a dilute mineral acid, e.g., aqueous H₂SO₄ in aqueous alcohol. The reaction temperature may range from room temperature, i.e., about 25° C. to above room temperature, i.e., about 60° C. The compounds of formula XI may then be reduced to the novel intermediates of formula V.

Another process, although it does not form a part of the present invention, is useful in producing the novel intermediates of formulas IV and V. The following process is included in this specification for the sake of unity.

The compounds of formula IV above may be produced by the successive reaction of the compounds of the formula

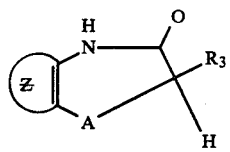                               XII wherein A,

$R_3$ and $R_4$ are as in formula II with dimorpholinophosphinic chloride to produce compounds of the formula

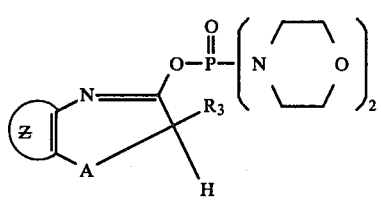                               XIII wherein A,

R3 and R4 are as in formula XII; which imino phosphates are then displaced by the anion of a nitroalkane to produce the novel intermediates

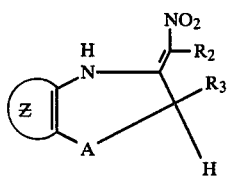

wherein A,

R3 and R4 are as described in formula XII.

The displacement reaction is affected with nitroalkane, i.e., nitromethane, nitroethane, etc., in the presence of a base which is strong enough to generate the nitroalkane anion. Suitable bases include the alkali metal or alkaline earth metal alkoxides, hydrodes, amides or hydroxides. The reaction is preferably carried out in an inert solvent, such as dimethylformamide, dimethylsulfoxide, or an ether, at temperatures below or above room temperature, i.e., in the range of $-50°$ C. to $150°$ C.

Another process to produce intermediates of formula IV wherein $R_2$ is hydrogen and A is an N-oxide comprises the ring expansion of compounds of the formulae

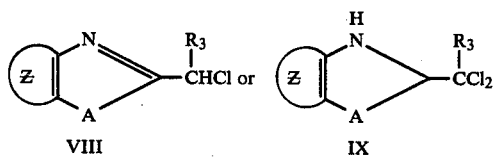

wherein A is

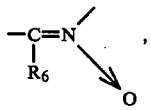

$R_6$,

$R_3$ and $R_4$ are as described in formula II except that $R_4$ is not amino or substituted amino.

The ring expansion comprises the reaction of the compounds formulae VIII or IX with nitromethane in the presence of a base strong enough to generate the nitromethane anion. Suitable bases include the alkali metal and alkaline earth mertal alxoxides e.g., potassium tertiary butoxide, amides e.g., lithium amide or hydrides e.g., sodium hydride. The reaction may be preferably carried out in an inert solvent such as anhydrous ether e.g., THF, dimethylformamide, dimethylsulfoxide, etc.

and at a temperature in the range of about $-20°$ C. to $25°$ C.

Compounds of the formula IA wherein A is

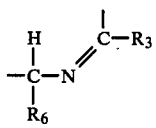

may be formed by isomerization of the 5,6-double bond in Formula I compounds to the 4,5-position. Formula IA compounds may be formed by the treatment of formula I compounds with an anhydrous base in the presence of an inert organic solvent.

All that is required of the base is that it be suitable for the purposes of the present invention, that is, that it effect the conversion of a compound of formula I above to the corresponding compound of the formula IA above. Among the many suitable bases can be included alkali metal lower alkoxides, such as sodium methoxide, potassium tertiary butoxide and the like and alkali metal hydrides, such as sodium hydride.

Representative, but by no means exclusively so, of inert organic solvent suitable for the purpose of the present invention are dimethylformamide, dimethylsulfoxide, tetrahydrofuran and the like. Here again, temperature and pressure are not critical aspects of this conversion step. However, it has been observed that temperatures of from about 31 50° C. to about 80°, most preferably from about $-30°$ to $25°$ C. are useful.

Compounds of the formula IA where A is

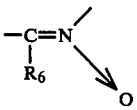

are formed by the conversion of corresponding formula I compounds into the N-oxides thereof. This conversion is affected by oxidizing a formula I compound with an organic peracid. A conventional organic peracid, such as peracetic acid, perpropionic acid, m-chloroperbenzoic acid, etc., can be utilized in carrying out this reaction. The oxidation can be affected at room temperature, or above or below room temperature.

Compounds of the formula IA where A is

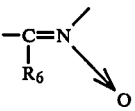

may be then utilized to produce compounds of formula I wherein $R_5$ is alkanoyloxy or hydroxy by methods known in the art, such as, for example, a Polonvski rearrangement utilizing an acid anhydride to form the alkanoyloxy radical which may be converted to the hydroxy by treatment with an alkali metal hydroxide such as sodium hydroxide. An example of such a Polonovski rearrangement is found in U.S. Pat. No. 3,296,249 issued Jan. 3, 1967 to S. C. Bell.

Compounds of the formula IA where A is

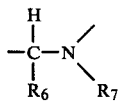

are formed by the reduction of corresponding formula I compounds to compounds of the formula

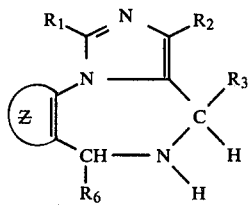

IA' wherein $R_1$, $R_2$, $R_3$, $R_4$, $R_6$ and

are as in formula I with the exception that $R_4$ is not nitro and $R_6$ is not nitro-substituted (since nitro substituents may be reduced to amino under the reaction conditions), which may be then converted to compounds of the formula

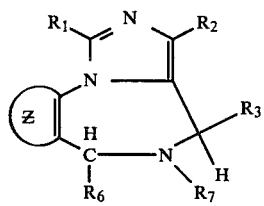

IA"

wherein $R_1$, $R_2$, $R_3$, $R_4$ and $R_6$ are as in formula IA' and $R_7$ is hydroxy, acyl or an aromatic or aliphatic sulfonyl group.

The reduction of formula I compounds to IA' compounds is accomplished by any suitable reducing agent but most preferably accomplished by hydrogen in the presence of a platinum oxide catalyst or zinc in the presence of acetic acid. These compounds (IA') may be converted to IA" compounds having an $R_7$-radical other than hydroxy by reaction with a member, for example, from the group comprising a lower alkyl halide, e.g., methyl iodide lower alkenyl halide, e.g., allyl bromide, lower alkynyl halide, e.g., propargyl-bromide, alkyl or aryl sulfonyl halide, e.g., tosyl chloride, mesyl chloride, nitrosyl chloride and a lower alkanoyl group providing agent, e.g., acetyl chloride. Also used above the term "lower alkynyl" includes unsaturated straight and branched chain carbon-hydrogen radicals which contain triple bonds, i.e., the radical compounds of the formula $C_nH_{2n-2}$ wherein n is 3–7, e.g., propargyl.

This process aspect is conveniently effected in the presence of an inert organic solvent such as an alkanoyl, e.g., ethanol and methanol, an ether such as diethyl ether and tetrahydrofuran, dimethylformamide and the like. Suitably, an acid acceptor is provided to the reaction zone to accept the hydrogen halide formed when utilizing a halide, e.g., an aryl sulfonyl (e.g., tosyl) halide or an alkyl sulfonyl (e.g., mesyl) halide, with a compound of the formula IA' above. Suitable acid acceptors are tertiary amines, e.g., triethylamine, pyridine and the like.

Temperature and pressure are not crticial aspects of the first stage of the process involving the conversion of the compound of the formula I above to the corresponding compound of the formula IA. However, the reaction is most preferably effected at about room temperature and atmospheric pressure for the preparation of compounds IA' and room temperature and above for the conversion of compounds IA' to IA" bearing an $R_7$ radical other than hydroxy.

Reduction of IA compounds wherein A is

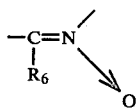

with hydrogen in the presence of platinum catalyst and acetic acid leads to IA" compounds wherein $R_7$ is hydroxy.

Compounds of formula IA" wherein $R_7$ is hydroxy, may be converted to the corresponding formula I unsaturated imine by treatment of the IA" compound with an acetic anhydride/pyridine mixture. No other solvent is necessary for this reaction and temperature is not critical although the reaction is best effected at room temperature.

Compounds of formula IA" above wherein $R_7$ is acetyl, mesyl or tosyl may be converted to the corresponding formula I unsaturated imine by treatment of the IA" compound with a non-aqueous base, e.g., potassium tertiary butoxide, in the presence of an inert solvent e.g., THF, DMF, etc. Such as reaction and the conditions at which it is run are well known in the art, see, for example U.S. Pat. No. 3,625,957 issued Dec. 7, 1971 to Fryer et al.

Compounds of Formula IA' above may be converted to the analogous formula I unsaturated compounds by oxidation of the secondary amine at the 5-position. Such a selective oxidation may be accomplished by known oxidants and reaction schemes see, for example, U.S. Pat. No. 3,322, 753, issued May 30, 1967 to Fryer et al.

Conversion of compounds of formula I which contain a Schiff base at the 5,6-position wherein $R_4$ is amino to compounds wherein $R_4$ is nitro may be suitably affected by, for example, the Sandmeyer Reaction wherein the amino group is replaced by a nitro group, for example by the treatment of a formula I compound wherein

is an amino substituted benzo moiety, with excess sodium nitrite in the presence of a copper sulfate/sodium sulfite mixture and utilizing as a solvent dilute sulfuric acid.

The resulting intermediate of the formula

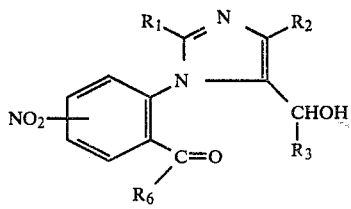   XXIII'

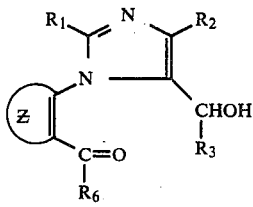   XXIII wherein $R_1$, $R_2$, $R_3$, and $R_6$ are as in formula I may then be converted to an analogous formula I compound. This process may be effected in a two-step sequence without isolation of the intermediate XXIV formed by treatment of the above formula XXIII' compound or its analogous diazepine of formula I with phosphorus tribomide in an inert organic solvent e.g., dichloromethane at about −10° to 25° C. (although temperature is not critical) and then subsequent treatment in situ with ammonia, preferably liquid ammonia which is allowed to warm to room temperature.

The Sandmeyer reaction has been found to also be applicable in producing compounds which contain a cyano, chloro or bromo in place of a nitro group. Such corresponding compounds of formula XXIII' can be converted to their ring closed analogs in the same manner as described above for nitro compounds.

It should be noted that certain compounds which contain a Schiff base at the 5,6-position may not readily open to a XXIII' type compound. These compounds proceed directly to the desired analogous formula I compounds wherein $R_4$ is nitro. Similarly, the above Sandmeyer reaction may be utilized to convert $R_4$=amino to $R_4$=cyano. As above, both analogous XXIII' type compounds and closed compounds may be present.

It should be noted and be obvious to one skilled in the art that certain oother substituents which may be present as $R_1$, $R_2$, $R_3$ and $R_6$ substituted may also be attacked during the above reactions, such as, for example, where $R_1$ or $R_2$ are a primary amine, alcohols, carboxylic acids or esters thereof, etc., but such vulnerable groups may be blocked by a suitable protecting group or modified before the above reaction sequence is carried out. Such methods of modifying or protecting groups subject to attack are well known in the art. Further, certain of the substituents which might be attacked during the above reaction sequence and reaction sequences set forth throughout this application may be reconverted to the original substituents utilizing methods known in the art or disclosed herein.

Compounds of the formula IA where A is

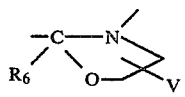

and wherein V is hydrogen or methyl, may be formed by the direct reaction of formula I compounds with ethylene oxide or propylene oxide in the presence of a Lewis acid catalyst or where V is lower alkyl or hydrogen by the reaction of a compound of the formula wherein $R_1$, $R_2$, $R_3$,

and $R_6$ are as in formula I except that $R_4$ is not amino or substituted amino with phosphorus tribomide and subsequent treatment of the intermediate (XXIV) with a compound selected from the group consisting of ethanol amine, a 1-alkyl substituted ethanolamine and a 2-alkyl substituted ethanolamine as shown in the following reaction scheme:

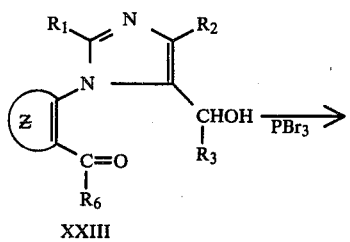
XXIII

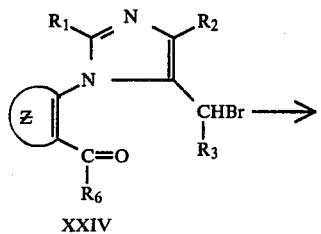
XXIV

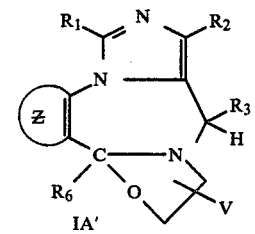
IA'

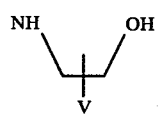

V is hydrogen or lower alkyl

The compounds of formula XXIII may be formed by the reaction of a compound of the formula IE with sodium nitrite in the presence of a compatible solvent such as water or dilute mineral acid. The temperature of the reaction may be −10° C. to room temperature. The reaction of formula XXIII compounds with phosphorus tribromide is effected as illustrated above, preferably in an inert organic solvent such as dichloromethane at about room temperature although such temperature is not critical.

The reaction of the compound of formula XXIV with ethanolamine or 1-alkyl or 2-alkyl substituted ethanolamine is effected in situ, i.e., with a suitable inert solvent such as dichloromethane, at a temperature range of −10° C. to reflux, with about room temperature preferred.

The direct reaction of formula I compounds with ethylene oxide or propylene oxide is preferably catalyzed by a Lewis acid, e.g., titanium tetrachloride, boron trifluoride, etc.

In compounds of formula I and their analogs wherein the ketal group, e.g.

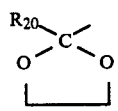

is present as a 8-position substituent in an imidazobenzodiazepine, such ketal group may be converted to an 8-position ketone by subjecting the ketal roup to a mild acid hydrolysis. The 8-ketone can then be converted to a 8-position secondary or tertiary alcohol which is racemic in nature. The reaction conditions therefor, for the above two steps, are found in U.S. Pat. No. 3,846,410 issued Nov. 5, 1974.

As stated above compounds of formula I may be directly reacted with ethylene oxide or propylene oxide to produce formula IA compounds, i.e., oxazolo type compounds. Reaction parameters and conditions to effect such a reaction are known in the art, see for example U.S. Pat. No. 3,868,362 issued Feb. 25, 1975 to Fryer et al and U.S. Pat. No. 3,905,956 issued Sept. 16, 1975 to Derieg et al.

Yet another process to produce the compounds of formula I consists of the following reaction scheme:

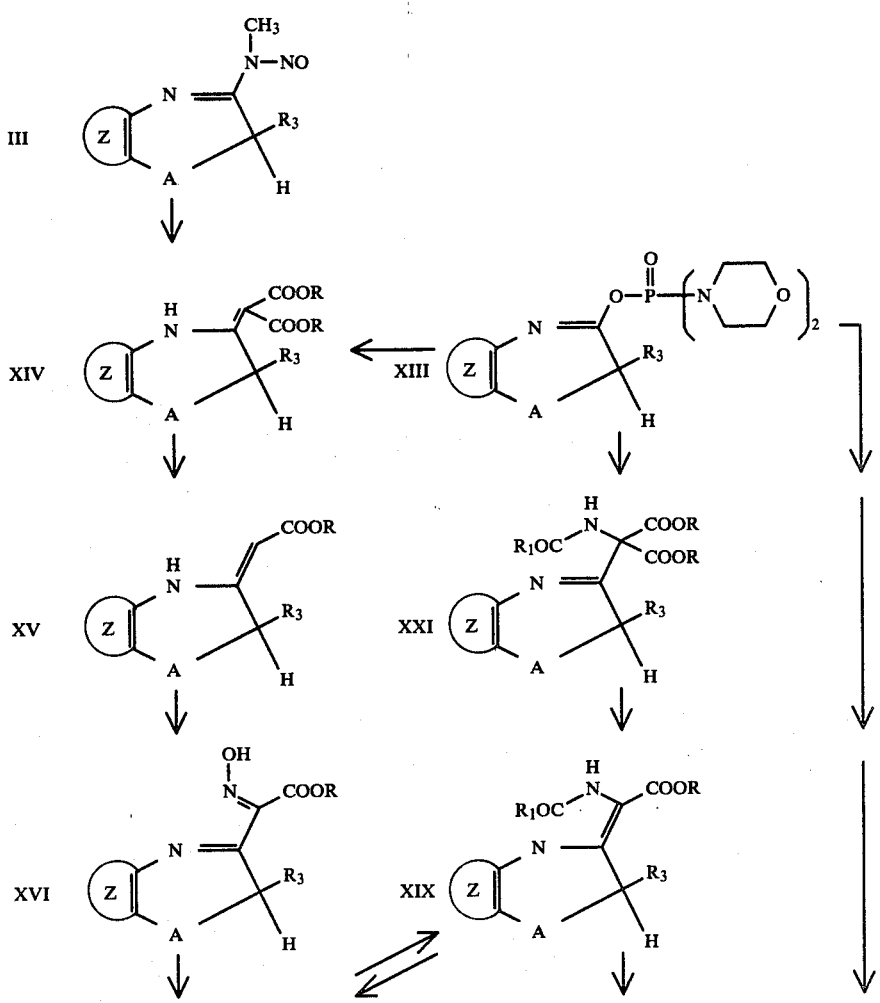

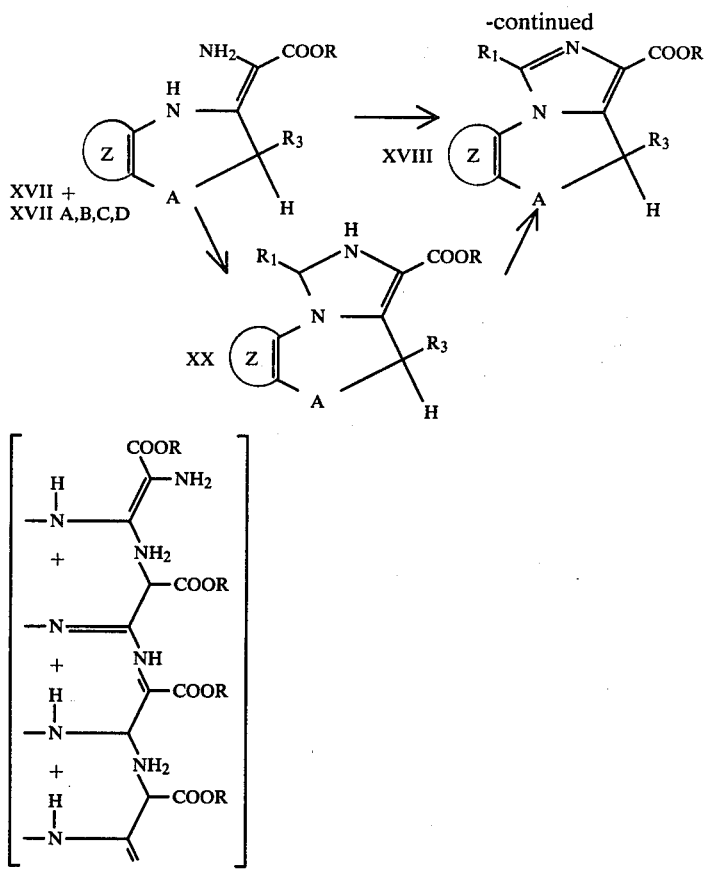

In the above reaction scheme unless otherwise indicated R is lower alkyl, $R_1$, $R_3$, $R_4$ and $R_6$ are as in formula I and A is as in formula I but may also be

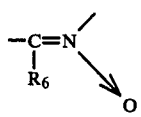

but any N-oxide moiety present in the above reaction scheme will be removed during the reaction step XVI→XVII+isomers.

It is obvious to one skilled in the art that certain of the substituents may be attacked during the above reactions but such vulnerable groups may be protected or modified prior to the above reactions or if allowed to be attacked may be reconverted to the original substituent utilizing well known methods after such reaction is carried out.

XIII or III→XIV—Compounds of formula XIII may be condensed with the anion generated from malonic ester e.g., of the formula

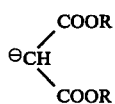

to produce compound of formula XIV. The anion is generated by deprotonating malonic ester with a suitable strong base such as alkali metal or alkaline earth metal alkoxides, hydrides or amides. The reaction of the formula XIII or III compounds with the malonic ester anion is preferably effected in a solvent such as hydrocarbons, e.g., benzene, toluene, hexane, ethers, e.g., dioxane, THF, diethyl ether, DMF, DMSO etc., at a range of below room temperature to 150° C., preferably 0° C. to 100° C., most preferably room temperature. It should be pointed out that any amino or substituted amino group may be present in protected form in this reaction step. The protected moiety can be removed afterwards at any convenient stage, for example, subsequent to formation of formula XVIII compound.

XV→XVI—Compounds of formula XVI are produced by the nitrosation of compounds of formula XV by reacting same with nitrous acid generated from, for example, an alkali metal nitrite, alkyl nitrite or nitrosyl chloride, by reaction with organic or inorganic acid. Suitable solvents for the nitrosation reaction include ethers, alcohols, water, acids, e.g., acetic acid, DMF, DMSO and chlorinated hydrocarbons. The reaction may be carried out at about room temperature although such temperature is not critical.

XVI→XVII+XVII A,B,C and D—Compounds of the formula XVII are produced by the reduction of compounds of formula XVI with Raney nickel and hydrogen or with zinc and acetic acid. This reduction results in the predominant production of compounds of formula XVII with concurrent side production of small amounts of several possible isomers, i.e., compounds of the formulas XVII A, B, C and D. It should be noted that the above reductive step would remove any N-oxide moiety present on the 4-position nitrogen and would reduce vulnerable groups, if present, as $R_4$, such as, a 7-position $NO_2$, or a 7-position CN. These groups may be subsequently replaced by methods known in the art, for example, a compound of formula XVII wherein $R_4$ is amino can be converted to corresponding compounds wherein $R_4$ is nitro or cyano via a Sandmeyer reaction as set forth in this specification.

A method for preparing compounds of formula XVII, particularly, wherein $R_4$ is nitro or cyano consists of, for example, in the conversion of a formula XIX compound, shown in the above reaction scheme, wherein $R_1$ is benzyloxy or any other equivalent protecting group which may be cleaved, e.g., carbobenzoxy group, and R is lower alkyl. The conversion consists of cleavage of the $R_1$ substituent by reaction with HBr in acetic acid. The reaction may be run at from 0° C. to 100° C. most preferably at about room temperature in an inert solvent such as hydrocarbons, e.g., benzene, toluene, hexane, etc., or chlorinated hydrocarbons or, if desired, in acetic acid alone.

XIV→XV—Compounds of formula XV are formed decarboxylation of compounds of formula XIV by reacting formula XIV compound with an alkali metal hydroxide e.g., NaOH or KOH in a suitable solvent e.g., alcohols, ethers or DMSO at a temperature range of from temperature to reflux temperature, preferably 60° C. to 100° C.

XVII→XIX—Compounds of formula XIX may be formed by the acylation of formula XVII compounds with a compound of the formula:

$$R_1COX \text{ or } (R_1CO)_2O$$

wherein X is halo and $R_1$ is hydrogen, lower alkyl, phenyl, alkoxy lower alkyl, substituted phenyl, pyridyl or aralkyl.

Solvents for the above process step include methylene chloride, ethers, chlorinated hydrocarbons, etc., preferably in combination with an acid acceptor such as an organic or inorganic base such as triethylamine, pyridine or an alkali metal carbonate. The reaction may be effected at above or below room temperature but preferably is carried out at room temperature. Compounds of the formula XIX are isomeric in nature, that is, may exhibit either of the following stereochemical structures

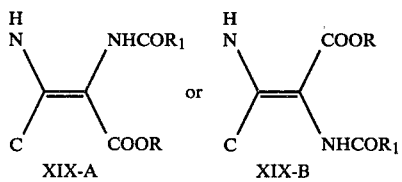

XIX-A     XIX-B

XVII→XVIII—Compounds of the formula XVIII are then formed by the reaction of formula XVII compounds with an alkanoic acid ortho ester of the formula:

$$R_1C(OR)_3$$

wherein R is lower alkyl and $R_1$ is hydrogen, lower alkyl, alkoxy lower alkyl or halo lower alkyl or its equivalents, e.g., ortho amides, the dimethylacetal of N,N dimethylformamide, N,N,N',N', N'',N''-hexamethyl methane triamine, or nitriles, such as, acetonitrile, and ester imidates e.g.,

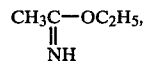

following the disclosed reaction conditions and parameters set forth previously in the specification wherein formula V compounds are directly converted to formula VII compounds.

XVII→XX—Compounds of the formula XX are formed by the reaction of formula XVII compounds with an aldehyde of the formula $R_1$CHO wherein $R_1$ is as in formula I, but any amino, substituted amino and preferably any RCO group should be present in protected form. The protecting moiety can be removed afterwards, e.g., subsequent to the formation of formula XVIII compounds. Solvents suitable for this reaction step are hydrocarbons such as benzene, alcohols, ethers, chlorinated hydrocarbons, DMF, DMSO, etc., with or without the presence of water-binding agents, e.g., molecular sieves at above or below room temperature, preferably from room temperature to reflux temperature of the solvent.

XX→XVIII—Compounds of the formula XX may be converted to formula XVIII compounds by oxidation in situ by oxidizing agents such as manganese dioxide, air, oxygen, etc.

XIX→XVIII—Compounds of the formula XVIII may also be formed by the dehydration of formula XIX compounds or isomers thereof with concurrent cyclization by heating. In this reaction step, $R_1$ is restricted to hydrogen, lower alkyl, phenyl, alkoxy lower alkyl, substituted phenyl, pyridyl and aralkyl. This reaction step may be carried out with or without solvent, e.g., DMF, ethylene glycol, hexamethyl phosphoric triamide, at a temperature range of 100° C. to 300° C., preferably at 150° C. to 250° C., e.g., 200° C., with or without the presence of catalysts and water binding agents. Compounds of the formula XVIII may also be formed from formula XIII compounds in situ without isolation of compounds of the formulae XXI and XIX.

XIII→XXI—Compounds of the formula XXI may be formed by the condensation reaction of a compound of the formula XIII with the anion generated from acyl amino malonic ester of the formula

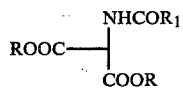

wherein R is lower alkyl and $R_1$ is hydrogen, lower alkyl, alkoxy lower alkyl, substituted phenyl, phenyl, pyridyl, aralkyl, benzyloxy, i.e., $OCH_2C_6H_5$ to produce compound of formula XXI. The anion is generated by deprotonating acylamino malonic ester with a suitable strong base such as alkali metal or alkaline earth metal alkoxides, hydrides or amides. The reaction of the formula XIII compounds with the acyl amino malonic ester anion is preferably effected in a solvent such as hydrocarbons e.g., benzene, toluene, hexane, ethers, e.g., dioxane, THF, diethyl ether, DMF, DMSO etc., at a temperature range of below room temperature to 150° C., preferably 0° C. to 100° C., most preferably room temperature.

XXI→XIX—Compounds of formula XIX and isomers thereof are formed by the decarboxylation of formula XXI compounds with an alkali metal alkoxide in a solvent such as ethers, alcohols, DMSO, DMF, etc., at above or below room temperature, preferably at room temperature.

The following general reaction scheme is illustrative of several of the reactions of the intermediate compound of formula XVIII to produce compounds of the formula I. It is obvious to one skilled in the art that certain of the substituents may be attacked during the below reactions but such vulnerable groups may be modified before or reconverted after the below reaction sequence is carried out.

In the below reaction schemes, unless otherwise indicated, R is lower alkyl.

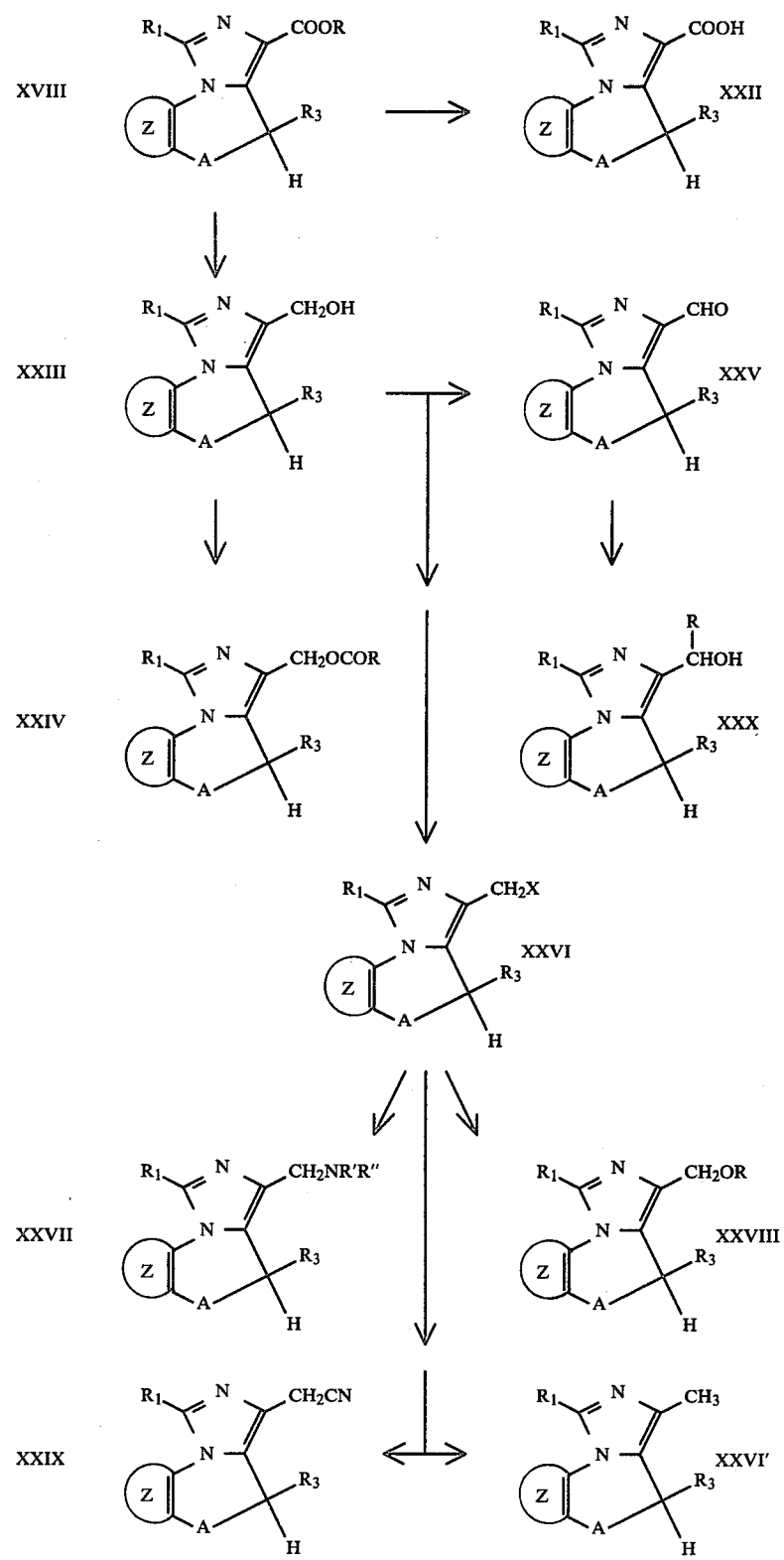

-continued
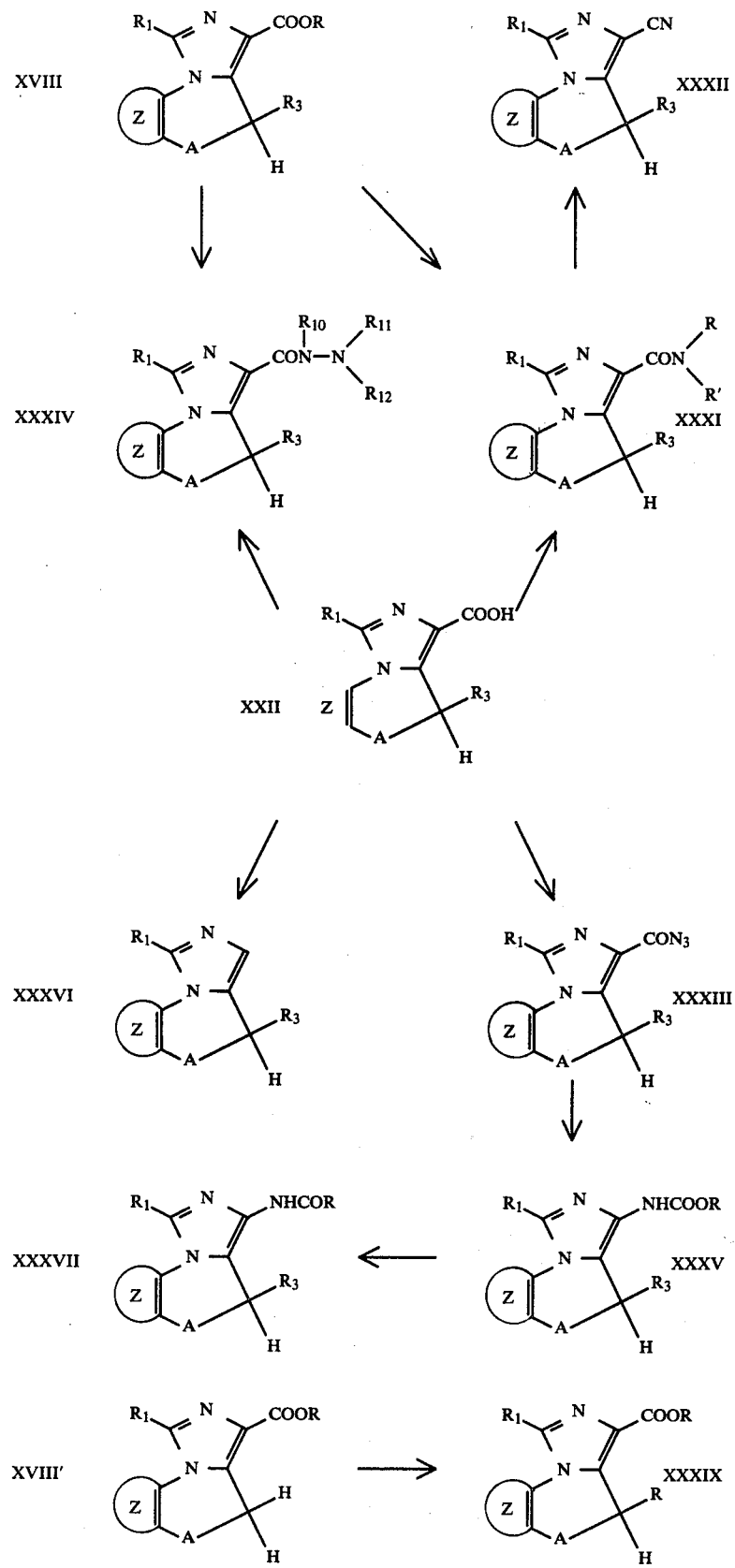

-continued
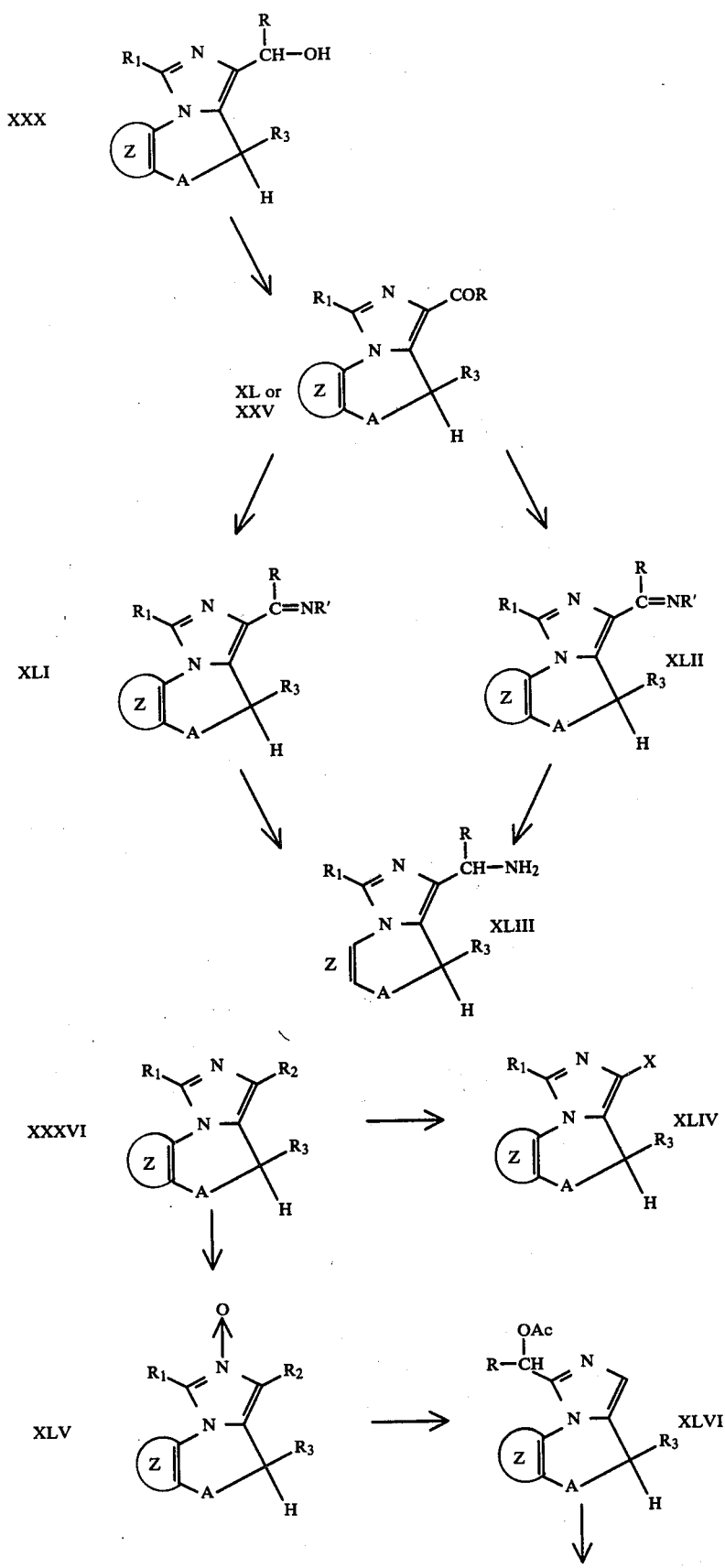

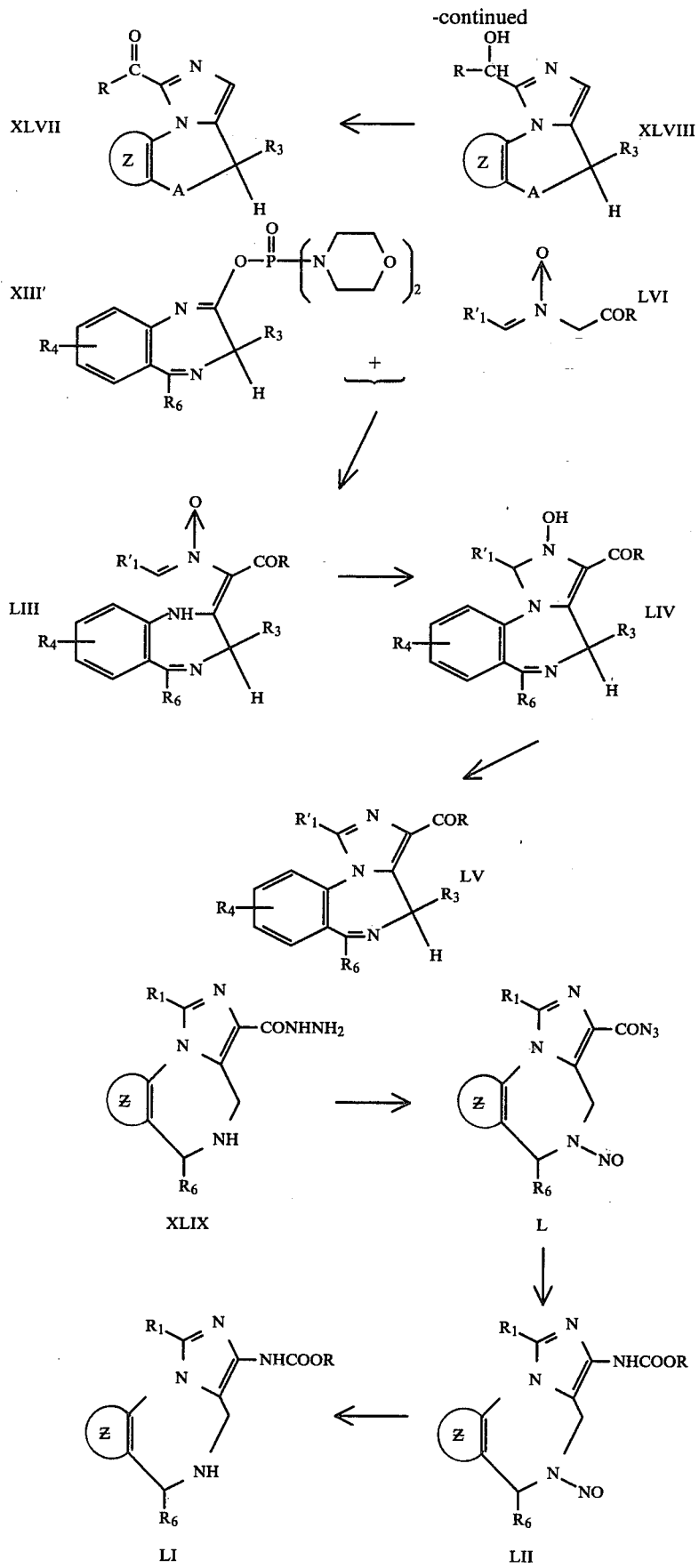

XVIII→XXII—Formula XXII compounds are formed by hydrolyzing formula XVIII compounds to the corresponding acids, preferably with alkali metal hydroxides, e.g., NaOH or KOH. This hydrolysis is conveniently effected in an inert solvent. Suitable solvents are alcohols, e.g., methanol, ethanol; ethers, e.g., dioxane, tetrahydrofuran; dimethylformamide, in combination with water. It is preferable to conduct this reaction step at a temperature between room temperature and the boiling point of the reaction mixture.

It is evident that during this reaction step an acyloxyalkyl group present will be hydrolyzed to the corresponding hydroxyalkyl group which in turn can be converted back to the acyloxyalkyl group at a convenient later stage. An $R_1$- group having the meaning of —COOR will also be hydrolyzed and decarboxylated to a corresponding compound wherein $R_1$ is hydrogen. The —COOR moiety can be reintroduced from a formyl or hydroxymethyl group in known manner. A haloalkyl group present may be affected in this reaction step yielding a corresponding hydroxyalkyl compound which may also be converted back to the halo alkyl compound at a later stage in usual manner. Any compound of formula XVIII wherein $R_4$ is hydroxyalkyl should be protected during this halogenation reaction step, e.g., in form of the tetrahydropyranylether derivative thereof.

XVIII→XXIII—Formula XXIII compounds are formed by the reduction of formula XVIII compounds, preferably with lithium aluminum hydride or an equivalent reducing agent. This reduction is conveniently conducted in an inert solvent. Suitable solvents are hydrocarbons, e.g., hexane, toluene; ethers, e.g., diethylether, tetrahydrofuran, dimethoxyethane; or mixtures thereof. It is preferable to perform this reduction at a temperature between about $-50°$ C. and the boiling point of the reaction mixture, most preferably between about $-20°$ C. and $0°$ C.

Nitro and cyano groups present may be affected during this reaction step. Such groups can be formed at a later stage of the synthesis utilizing methods of reconversion previously discussed.

XXIIIΔXXIV—Compounds of formula XXIII can be converted to compounds of formula XXIV by acylation with acid anhydrides or acid chlorides in presence or absence of an acid acceptor. This acylation is conveniently conducted in an inert solvent. Suitable solvents are hydrocarbons, e.g., hexane, toluene; chlorinated hydrocarbons, e.g., methylene chloride; ethers, e.g., tetrahydrofuran; dimethylformamide. Preferably this acylation is conducted at a temperature between about $-50°$ C. and $150°$ C., most preferably at room temperature. Acid acceptors that can be used in this reaction step are for instance pyridine, triethylamine, potassium carbonate.

It is evident that any substituent present as $R_1$ and/or $R_4$ and liable to being acylated during this reaction step should be protected in the usual manner in order to avoid any undesired acylation of such groups.

XXIII→XXV—Compounds of formula XXV can be prepared by oxidation of formula XXIII compounds by known oxidants such as chromium trioxide and manganese dioxide. This oxidation is conveniently conducted in an inert solvent. Suitable solvents are hydrocarbons, e.g., hexane, toluene; chlorinated hydrocarbons, e.g., methylene chloride; ketones, e.g., acetone; organic acids, e.g., acetic acid; pyridine, dimethylformamide, dimethylsulfoxide. The oxidation is preferably performed at a temperature between about $-50°$ C. and the boiling point of the reaction mixture, most preferably at about $0°$ C. and room temperature.

It is evident that any substituent present as $R_1$ and/or $R_4$ as hydroxyalkyl must be protected in the usual manner during this reaction step.

XXIII→XXVI—Compounds of formula XXVI are prepared by substitution of hydroxy group in the 3-substituent of formula XXIII compounds with a halogen. This reaction is preferably carried out by reagents such as a phosphorous halide, e.g., phosphate trichloride, phosphorous tribromide or thionyl chloride. This reaction step is conveniently conducted in an inert solvent or in the absence of a solvent. Suitable solvents are hydrocarbons, e.g., hexane, toluene; chlorinated hydrocarbons, e.g., methylene chloride; ethers, e.g., tetrahydrofuran. The temperature at which this reaction step is performed is preferably situated between about $-50°$ C. and $100°$ C., most preferably between about $0°$ C. and room temperature.

It is evident that any $R_1/R_4$ hydroxyalkyl group should be protected in case a conversion into the corresponding haloalkyl derivative is deemed undesirable.

XXVI→XXVII; XXVIII; XXIX—Compounds of formula XXVI can be reacted such that the halogen in the 3-substituent is nucleophilically displaced by other nucleophilic groups such as an amine (XXVII, wherein R' is hydrogen or lower alkyl and R" is hydrogen, lower alkyl or acyl), alkoxide (XXVIII) and cyanide (XXIX).

In the reaction step XXVI→XXVII a compound of formula XXVI is treated with ammonia or a mono- or dialkylamine. A compound obtained wherein R; and/or R" is hydrogen can, if desired, be acylated with a suitable acylating agent. This reaction step can be effected in the absence or in the presence of an inert solvent. Suitable solvents are hydrocarbons, e.g., hexane, toluene; chlorinated hydrocarbons, e.g., methylene chloride, chlorobenzene; ethers, e.g., diethylether, tetrahydrofuran; dimethylformamide, dimethylsulfoxide. This reaction is preferably conducted at a temperature between about $0°$ C. and the boiling point of the reaction mixture with or without applying pressure above atmospheric pressure.

It is evident that a compound of formula XXVII wherein $R_1$ is haloalkyl has to be produced in a further step, e.g., using the corresponding hydroxyalkyl derivative as starting material, in known manner.

The reaction step XXVI→XXVIII is conveniently effected by treating a compound of formula XXVI with an alkali metal alkoxide, preferably in the presence of an inert solvent. Suitable solvents are hydrocarbons, e.g., hexane, toluene; ethers, e.g., tetrahydrofuran; dimethylformamide, dimethylsulfoxide, alcohols corresponding to the alkoxide used. Alternatively, a compound of formula XXVI is treated with an alkanol in the presence of an organic base, e.g., pyridine or triethylamine. The temperature to be applied for this reaction step is preferably between about $-50°$ C. and the boiling point of the reaction mixture, most preferably between room temperature and about $100°$ C., with or without using pressure above atmospheric pressure.

It is evident that a compound of formula XXVIII wherein $R_1$ is haloalkyl has to be produced in a further step as indicated above.

It is also evident that any hydroxyalkyl substituent present will have to be protected during this reaction step and deprotected at a later stage.

The reaction step XXVI→XXIX is conveniently effected by treating a compound of formula XXVI with an alkali cyanide, preferably in an inert solvent. Suitable solvents are hydrocarbons, e.g., hexane, toluene; ethers, e.g., tetrahydrofuran; dimethylformamide, dimethylsulfoxide. The temperature for this reaction step is preferably situated between room temperature and the boiling point of the reaction mixture, most preferably between about 25° C. and 160° C.

It is evident that also in this step a compound of formula XXIX wherein $R_1$ is haloalkyl has to be produced in a further step as indicated above.

XXVI→XXVI'—Compounds of formula XXVI' are formed by reduction of compounds of formula XXVI with hydrogen using a suitable catalyst, e.g., palladium or Raney nickel. This reaction step is conveniently effected in the presence of an inert solvent. Suitable solvents are hydrocarbons, e.g., hexane, toluene; ethers, e.g., tetrahydrofuran, dioxane. The reaction is preferably conducted at a temperature between about room temperature and the boiling point of the reaction mixture, most preferably at room temperature. If desired, pressure above atmospheric pressure can be applied.

It is evident that any nitro, cyano or additional haloalkyl substituent in a compound of formula XXVI' has to be formed at a later stage of the synthesis.

XXV→XXX—Compounds of formula XXX are formed by reaction of formula XXV 3-position aldehyde with an organometallic reagent such as a Grignard reagent or an alkyl lithium reagent. This reaction is conveniently effected in an inert solvent. Suitable solvents are hydrocarbons, e.g., hexane, toluene; chlorinated hydrocarbons, e.g., methylene chloride, ethers, e.g., diethylether tetrahydrofuran, dimethoxyethane. The reaction is preferably conducted at a temperature between about $-100°$ C. and 50° C., most preferably between about $-20°$ C. and room temperature.

It is evident that any carbonyl group in the substituent $R_1$ and $R_4$ has to be protected during this reaction step. Since an ROOC-group would be affected in the step XXV→XXX such a group has to be formed after production of the compound of formula XXX, e.g., by using the corresponding aldehyde with protected α-hydroxyalkyl substituent in the 3-position as starting material. Further, any cyano substituent will have to be formed at a later stage of the synthesis.

XVIII or XXII→XXXI—Compounds of formula XXXI may be produced by direct aminolysis of formula XVIII (with an amino compound of the formula H$_2$NR where R represents hydrogen, lower alkyl, lower alkenyl, aryl or the group —(CH$_2$)$_n$NR$_{13}$R$_{14}$ wherein n is 1 to 4 and $R_{13}$, $R_{14}$ are defined above) or by the conversion of a formula XXII compound to an acid chloride, e.g., by treatment with phosphorus pentachloride and subsequent reaction with an amino compound of the formula HNRR' (wherein R, R' represent individually hydrogen, lower alkyl, hydroxy lower alkyl, lower alkenyl, aryl or form part of a heterocyclic ring or the group —(CH$_2$)$_n$NR$_{13}$R$_{14}$ wherein n is 1 to 4 and $R_{13}$, $R_{14}$ are defined above).

The step XVIII→XXXI is conveniently effected in an inert solvent or in the absence of a solvent. Suitable solvents are hydrocarbons, e.g., hexane, toluene; ethers, e.g., tetrahydrofuran; alcohols, e.g., methanol, ethanol; dimethylformamide, dimethylsulfoxide, hexamethyl phosphoric triamide. It is preferable to perform this reaction step at a temperature between about 50° C. and 200° C., must be preferably between about 100° C. and 150° C., applying atmospheric pressure of pressure above atmospheric pressure.

It is evident that any haloalkyl or ROOC- substituent has to be formed subsequent to production of the formula XXXI compound.

The step XXII→XXXI is conveniently effected in an inert solvent. Suitable solvents are hydrocarbons, e.g., hexane, toluene; ethers, e.g., tetrahydrofuran, chlorinated hydrocarbons, e.g., methylene chloride, chlorobenzene. It is preferable to perform this reaction at a temperature between about $-20°$ C. and the boiling point of the reaction mixture, most preferably between about 0° C. and 50° C.

It is evident that a hydroxyalkyl substituent has to be protected during this reaction step.

XXXI→XXXII—Formula XXXII compounds are formed by dehydration of formula XXXI compounds where R and R' are hydrogen. Dehydration is accomplished by reactants such as phosphorus pentoxide, phosphorusoxy chloride in a compatible solvent. Suitable solvents are pyridine, hydrocarbons, e.g., hexane, toluene; chlorinated hydrocarbons, e.g., methylene chloride. Preferably this reaction is conducted at a temperature between room temperature and the boiling point of the reaction mixture, most preferably between about 50° C. and 120° C.

XVIII or XXII→XXXIV—Formula XXXIV compounds are formed by direct hydrazinolysis or conversion to acid chloride, e.g., by treatment with phosphorous pentachloride, and subsequent treatment by a hydrazine. The symbols $R^{10}$, $R^{11}$ and $R^{12}$ in formula XXXIV have the same meaning as indicated in formula I. The same reaction conditions as indicated for the step XXII→XXXI can also be used for the step XXII→XXXIV and the same restrictions as to substituents liable to being affected during the reaction should be observed. The reaction XVIII→XXXIV is conveniently performed in an inert solvent or in the absence of a solvent. Suitable solvents are hydrocarbons, e.g., hexane, toluene; ethers, e.g., tetrahydrofuran; alcohols, such as methanol, ethanol. Preferably this reaction is conducted at a temperature between about 50° C. and 150° C., most preferably between about 80° C. and 100° C. The same restrictions as to substituents liable to be affected during this reaction step should be observed as indicated for the reaction step XVIII→XXXI.

XXII→XXXVI—Formula XXXVI compounds are formed by decarboxylation with or without catalyst and with or without solvent. This decarboxylation is conveniently effected by application of heat, e.g., at a temperature between about 100° C. and 350° C., preferably about 150° C. and 230° C. Solvents that can be used in this reaction step are hydrocarbons, e.g., mineral oil; chlorinated hydrocarbons, ethers, alcohols, e.g., ethylene glycol, dimethylformamide, dimethylsulfoxide, hexamethyl phosphoric triamide. Useful catalysts are for instance metals such as copper powder or metal salts such as Cu$^+$ or Ag$^+$ salts.

XXII→XXXV—Formula XXXV compounds are formed by modified Curtius reaction, i.e., by reaction of formula XXII compounds with phosphoryl azides, e.g., N$_3$PO(OC$_6$H$_5$)$_2$, to form azides, i.e., formula XXXIII compounds, and subsequent heating of these azides with an alcohol which takes part in reaction. The azide formation is conveniently performed in an inert solvent. Suitable solvents are hydrocarbons, e.g., hexane, toluene; ethers, e.g., tetrahydrofuran. This reaction step is preferably conducted at a temperature between about 0° C. and 100° C., preferably at room temperature, if desired, utilizing pressure above atmospheric pressure although pressure is not critical. Preferred solvents include triethylmine and pyridine.

It is obvious that any amino and substituted amino group present has to be protected during this reaction step. It is also advisable to use a compound of formula XXII with protected hydroxyalkyl groups. Removal of the protecting group(s) can be effected after formation of compound of formula XXXV.

The conversion of the azide of formula XXXIII to the carbamic acid ester of formula XXXV, wherein R is lower alkyl or aralkyl, is conveniently effected in the alcohol reactant serving as solvent. Additionally, inert solvents may be present such as hydrocarbons, e.g., hexane, toluene; chlorinated hydrocarbons, e.g., methylene chloride; ethers, e.g., tetrahydrofuran; pyridine, triethylamine. Preferably the reaction is conducted at a temperature between about 50° C. and 200° C., most preferably between about 80° C. and 160° C.

It is evident that a haloalkyl substituent present would be affected during this reaction step and thus has to be formed subsequent to the production of compound of formula XXXV in known manner.

XXV→XXXVII—Formula XXXVII compounds are formed by reaction of formula XXXV compounds where R is benzyl with palladium and hydrogen to yield a free amine which is acylated with an acid halide or acid anhydride. The formation of the free amine is conveniently effected in an inert solvent. Suitable solvents are hydrocarbons, e.g., hexane, toluene; ethers, e.g., tetrahydrofuran, alcohols, e.g., methanol, ethanol; organic acids, e.g., acetic acid, acid anhydrides, e.g., acetic anhydride, in which case the acylation occurs in situ. The preferred temperature range for this reaction step is between room temperature and above 100° C., if desired, using pressure above atmospheric pressure. For the acylation the same reaction conditions can be used as indicated for the step XXIII→XXIV.

It is evident that any haloalkyl, nitro and cyano substituents has to be formed subsequent to the production of the compound of formula XXXVII in known manner. It is also evident that an amino group has to be protected, e.g., in form of the corresponding phthalyl derivative.

XVIII'→XXXIX—Formula XXXIX compounds are formed by alkylation of formula XVIII' compounds wherein $R_3$ is hydrogen with alkyl halides in the presence of strong base, e.g., methyl iodide in the presence of potassium tertiary butoxide. This reaction step is conveniently effected in an inert solvent. Suitable solvents are hydrocarbons, e.g., hexane, toluene; ethers, e.g., tetrahydrofuran; dimethylformamide, dimethylsulfoxide. Preferably the reaction is conducted at a temperature between about −50° C. and room temperature, most preferably between about −30° C. and −10° C.

It is evident that any substituent present should not be a haloalkyl substituent or a substituent with active hydrogen in case alkylation of such latter substituent is undesirable.

XXX→XL—Formula XL (including XXV) compounds are formed by oxidation of formula XXX compounds as carried out in step XXIII→XXV (R is hydrogen or lower alkyl).

XL→XLI—Formula XLI compounds, wherein R is hydrogen or lower alkyl are formed by treatment of formula XL (including XXV) compounds with a hydrazine of formula $NH_2R'$, wherein $R'$ is amino, mono- or dialkyl amino or arylamino. This reaction is conveniently effected in an inert solvent. Suitable solvents are hydrocarbons, e.g., hexane, toluene; chlorinated hydrocarbons, e.g., methylene chloride; ethers, e.g. tetrahydrofuran; alcohols, e.g., methanol, ethanol; organic acids, e.g., acetic acid, pyridine. Preferably the reaction is conducted at a temperature between room temperature and the boiling point of the reaction mixture.

It is evident that any $R_1$ and/or $R_4$ acyl group has to be protected during this reaction step and that any haloalkyl group has to be formed subsequent to the production of the compound of formula XLI.

XL→XLII—Formula XLII compounds wherein $R'$ is hydrogen, hydroxy, lower alkyl or lower alkoxy and R is hydrogen or lower alkyl are formed by reaction of formula XL (including XXV) compounds with ammonia, hydroxyl amine, a lower alkylamine or a lower alkoxyamine. This reaction step is conveniently effected in an inert solvent. Suitable solvents are hydrocarbons, e.g., hexane, toluene; chlorinated hydrocarbons, e.g., methylene chloride; ethers, e.g., tetrahydrofuran; alcohols, e.g., methanol, ethanol; organic acids, e.g., acetic acid; pyridine. Preferably the reaction is conducted at a temperature between room temperature and about 150° C., if desired, at a pressure above atmospheric pressure.

It is evident that any $R_1$ and/or $R_4$ acyl group has to be protected during this reaction step and that any haloalkyl group has to be formed subsequent to the production of the compound of formula XLII.

XLI or XLII→XLIII—Formula XLIII compounds, wherein R is hydrogen or lower alkyl are obtained by reduction of formula XLI or XLII compounds e.g. utilizing Raney nickel and hydrogen. This reaction step is conveniently effected in an inert solvent. Suitable solvents are hydrocarbons, e.g., hexane, toluene; ethers, e.g., tetrahydrofuran; alcohols, e.g., methanol, ethanol; dimethylformamide; organic acids, e.g., acetic acid; organic acid anhydrides, e.g., acetic acid anhydride, in which case acylation at the amino group formed occurs in situ leading to an acylated compound of formula XLIII. It is preferable to conduct this reaction step at a temperature between about 0° C. and 100° C., most preferably at room temperature, if desired, applying pressure above atmospheric pressure.

It is evident that any haloalkyl, nitro and cyano group has to be formed subsequent to the production of the compound of formula XLIII.

XXXVI→XLIV—Formula XLIV compounds wherein X is chloro, bromo or iodo are obtained by reacting formula XXXVI compounds wherein $R_2$ is hydrogen with an appropriate halogenating agent such as bromine, N-bromosuccinimide, N-chlorosuccinimide, etc. This reaction step is conveniently effected in an inert solvent. Suitable solvents are hydrocarbons, e.g., hexane, toluene; chlorinated hydrocarbons, e.g., methylene chloride; organic acids, e.g., acetic acid, inorganic acids, e.g., sulfuric acid. Preferably the reaction is conducted at a temperature between about 0° C. and the boiling point of the reaction mixture depending on the reagent used.

It is evident that any hydroxyalkyl and aminoalkyl substituent present must be protected during this reaction step. Furthermore the meaning of $R_1$ must be other than hydrogen. A compound of formula XLIV wherein $R_1$ is hydrogen can be produced from a corresponding compound wherein $R_1$ is —COOR by means of saponification and subsequent decarboxylation.

XXXVI→XLV→XLVI—Formula XLV compounds wherein $R_2$ is hydrogen, lower alkyl, lower alkoxy alkyl or acyloxy lower alkyl are obtained by reacting corresponding formula XXXVI compounds with a peracid such as meta chloro perbenzoic acid or peracetic acid. In the instances where $R_1$ is lower alkyl and $R_2$ is hydrogen, a compound of the formula XLVI is formed by subsequent reaction with an acid anhydride. The symbol A in formulae XLV and XLVI stand for the group —C($R_6$)=N— and —C($R_6$)=N(→O)— and R in formulae XLVI, XLVIII and XLVII is hydrogen or lower alkyl. The reaction step XXXVI→XLV is conveniently effected in an inert solvent. Suitable solvents are hydrocarbons, e.g., hexane, toluene; chlorinated hydrocarbons, e.g., methylene chloride; organic acids, e.g., acetic acid. Preferably the reaction is conducted at a temperature between about 0° C. and 50° C.

It is evident that any acyl group and preferably also any hydroxyalkyl group present should be protected during this reaction step. Furthermore, the presence of tertiary amino groups, ROOC-groups as well as

representing pyrazolo and $R_6$ representing pyridyl is excluded for this reaction step. An acyloxy alkyl group present may be transformed into a hydroxyalkyl, a haloalkyl, an aminoalkyl, a substituted aminoalkyl or a cyanoalkyl group subsequent to the formation of the compound of formula XLV.

The treatment with an acid anhydride, e.g., acetic acid anhydride for the conversion XLV→XLVI is conveniently effected in an inert solvent. Suitable solvents are hydrocarbons, e.g., hexane, toluene; chlorinated hydrocarbons, e.g., methylene chloride; ethers, e.g., tetrahydrofuran; dimethylformamide; dimethylsulfoxide. Acid anhydrides taking part in the reaction can also be used as solvents. This reaction step is advantageously effected at a temperature between room temperature and about 150° C., preferably between about 80° C. and 100° C.

It is evident that any amino group present will be acylated and any hydroxyalkyl group present will be esterified during this reaction step.

XLVI→XLVIII—Formula XLVIII compounds wherein A is as in formula XLV are obtained by reacting corresponding formula XLVI compounds with an alkali metal alkoxide or hydroxide. This reaction step is conveniently effected in an inert solvent. Suitable solvents are hydrocarbons, e.g., hexane, toluene; chlorinated hydrocarbons, e.g., methylene chloride; ethers, e.g., tetrahydrofuran; alcohols, e.g., methanol, ethanol; dimethylformamide; dimethylsulfoxide; hexamethyl phosphoric triamide; pyridine, amines, e.g., triethylamine. This reaction is preferably conducted at a temperature between about 0° C. and the boiling point of the reaction mixture depending on the reagent used.

XLVIII→XLVII—Formula XLVII compounds wherein A is as in formula XLV are formed by oxidation as in step XXIII→XXV.

XIII'→LV—Compounds of the formula LV are prepared by reacting a formula XIII' compound with a nitrone anion formed by the reaction of a formula LVI compound wherein $R_1'$ is phenyl, substituted phenyl or pyridyl and R is lower alkoxy or di-lower alkyl amino with a strong base, such as, butyl lithium, potassium tertiary butoxide, etc. The reaction (XIII'→LV) is effected in situ without isolation of intermediate compounds such as LIII and LIV. Solvents suitable for this reaction include hydrocarbons such as hexane, toluene, etc., ethers, e.g., THF, DMF and DMSO. Reaction temperature should be in the range of −100° C. to room temperature, preferably −80° C. to 25° C. e.g., about −70° C. with subsequent warming to room temperature to effect in situ cyclization.

XLIX (XXXIV')→L—Compounds of formula L are formed by reaction of formula XLIX compounds with nitrous acid to the azide. Solvents for this reaction include chlorinated hydrocarbons, alcohols such as methanol, ethanol, etc., organic acids, water and aqueous inorganic acids. The temperature at which the reaction is carried on can vary between −20° C. to room temperature with 0° C. to room temperature being preferred.

L→LII—Formula LII compounds are formed by the reaction of a formula L compound as disclosed in step XXII→XXXV utilizing the reaction parometers set forth.

LII→LI—Formula LI compounds are formed by reduction of formula LII compounds using Raney nickel and hydrogen. Solvents include hydrocarbons, e.g., hexane, toluene, benzene; ethers, e.g., THF and DMSO; alcohols, e.g., methanol, ethanol, etc., and organic acids. The reaction temperature ranges from 0° C. to 50° C. with room temperature being preferred. The reaction may be run, with or without the utilization of pressure.

Homologs of compounds of formulae XXVII, XXIX, XXIV, XXVI, XXVIII and XXVI' and compounds of formula XXX where the functional group in the substituent $R_2$ is in another position than the α-position can be prepared by homologation and/or modification of appropriate compounds disclosed above. For instance compounds of formula XXIX can be converted to the corresponding ester which in term can be subjected to similar reactions as disclosed above for the conversion of compounds of formula XVIII.

Compounds of the formulae I, IA, IB, IC, ID and IE and their pharmaceutically acceptable acid addition salts are useful as muscle relaxants, sedatives and anticonvulsants and many are particularly useful when utilized in intravenous and intramuscular preparations because of the acid addition salts' solubility in aqueous solution. As contemplated by this invention, the novel compounds of the formula I and their acid addition salts can be embodied in pharmaceutical dosage formulations containing from about 0.1 to about 40 mgs. most preferably 1–40 mg with dosage adjusted to species and individual requirements. The novel compounds of formulae I, IA, IB, IC, ID and IE and their pharmaceutically acceptable salts can be administered internally, for example, parenterally or enterally, in conventional pharmaceutical dosage forms. For example, they can be incorporated in conventional liquid or solid vehicles such as water, gelatin, starch, magnesium stearate, talc, vegetable oils and the like to provide tablets, elixirs, capsules, solutions, emulsions and the like according to acceptable pharmaceutical practices.

Applicants, in setting forth the disclosure of the above specification have cited the teaching of various articles and U.S. Patents. Such citations are meant to incorporate the teachings of these references for completeness of disclosure.

The following examples are illustrative but not limitative of the present invention. All temperatures are stated in degrees Centigrade.

EXAMPLE 1

7-Chloro-5-(2-fluorophenyl)-2-methylamino-3H-1,4-benzodiazepine

A solution of 200 g. (0.695 m) of 7-chloro-1,3-dihydro-5-(2-fluorophenyl)-2H-1,4-benzodiazepin-2-one in 2 l. of tetrahydrofuran and 250 ml. of benzene was saturated with methylamine with cooling in an ice bath. A solution of 190 g. (1 m) of titaniumtetrachloride in 250 ml. of benzene was added through a dropping funnel within 15 minutes. After addition the mixture was stirred and refluxed for 3 hours. Water, 600 ml., was added slowly to the cooled reaction mixture. The inorganic material was separated by filtration and was washed well with tetrahydrofuran. The water layer was separated and the organic phase was dried over sodiumsulfate and evaporated. The crystalline residue was collected with m.p. 204°–206°. The analytical sample was recrystallized from methylene chloride/ethanol, m.p. 204°–206°.

EXAMPLE 2

7-Chloro-5-(2-chlorophenyl)-2-methylamino-3H-1,4-benzodiazepine

Reaction as in Example 1 of 152.5 g. (0.5 m) of 7-chloro-5-(2-chlorophenyl)-1,3-dihydro-2H-1,4-benzodiazepin-2-one saturated with methylamine with 133 g. (0.7 m) of titaniumtetrachloride in 2 l. of tetrahydrofuran and 400 ml. of benzene yielded product with m.p. 216°–219°. The analytical sample was recrystallized from methylene chloride/ethanol and had m.p. 217°–219°.

EXAMPLE 3

5-(2-Chlorophenyl)-7-nitro-2-methylamino-3H-1,4-benzodiazepine

A solution of 94.6 g. (0.3 m) of 5-(2-chlorophenyl)-1,3-dihydro-7-nitro-2H-1,4-benzodiazepin-2-one in 2 l. of tetrahydrofuran and 300 ml. of benzene was cooled in ice-water and saturated with methylamine. A solution of 40.2 ml. (0.36 m) of titaniumtetrachloride in 300 ml. of benzene was added through a dropping funnel. After addition the mixture was stirred and refluxed for 3 hours. Water, 300 ml., was added slowly to the cooled reaction mixture. The inorganic solids were separated by filtration and washed well with tetrahydrofuran. The water was separated from the filtrate and the organic phase was dried over sodiumsulfate and evaporated. The residue was chromatographed over 500 g. of silica gel using 10% (v/v) ethanol in methylene chloride. Crystallization of the clean fractions from methylene chloride/ethanol yielded a yellow product with m.p. 219°–221°.

EXAMPLE 4

5-(2-Chlorophenyl)-7-nitro-2-(N-nitrosomethylamino)-3H-1,4-benzodiazepine

Sodium nitrite, 8.63 g. (0.125 m), was added in three portions over a 15 minute period to a solution of 33.9 g. (0.1 m) of 5-(2-chlorophenyl)-7-nitro-2-methylamino-3H-1,4-benzodiazepine in 200 ml. of glacial acetic acid. After addition stirring was continued for 1½ hours at room temperature and the product was precipitated by addition of water. The yellow solids were collected, washed with water, sucked dry and recrystallized from ethanol to yield yellow crystals with m.p. 164°–166°. The analytical sample was recrystallized from methylene chloride/ethanol, m.p. 167°–169°.

EXAMPLE 5

7-Chloro-1,3-dihydro-2-nitromethylene-5-phenyl-2H-1,4-benzodiazepine 4-oxide

A solution of 33 g. (0.1 m) of 7-chloro-2-(N-nitrosomethylamino)-5-phenyl-3H-1,4-benzodiazepine 4-oxide in 100 ml. of dimethylformamide was added to a mixture of 50 ml. of nitromethane, 12.5 g. (0.11 m) of potassium t-butoxide and 100 ml. of dimethylformamide. The reaction mixture was stirred under a stream of nitrogen for 1 hour. Afer addition of 10 ml. of glacial acetic acid, the product was crystallized by gradual addition of 250 ml. of water. The precipitated yellow material was collected, washed with water, methanol and ether to leave material with m.p. 253°–255° dec. The analytical sample was recrystallized from methylene chloride and showed the same m.p.

EXAMPLE 6

7-chloro-1,3-dihydro-2-nitromethylene-5-phenyl-2H-1,4-benzodiazepine

A mixture of 3.3 g. (0.01 m) of 7-chloro-1,3-dihydro-2-nitromethylene-5-phenyl-2H-1,4-benzodiazepine 4-oxide, 3.3 ml. of phosphorus trichloride and 300 ml. of methylene chloride was stirred at room temperature for 4 hours. The solution was washed with 10% aqueous sodium carbonate solution, was dried over sodium sulfate and evaporated. The crude product was purified by chromatography over 100 g. of silica gel using 10% (v/v) ethyl acetate in methylene chloride. The combined clean fractions were crystallized from methylene chloride/hexane to yield light yellow crystals with m.p. 184°–186°.

EXAMPLE 7

7-Chloro-5(2-chlorophenyl)-1,3-dihydro-2-nitromethylene-2H-1,4-benzodiazepine

Sodium nitrite, 10 g. (0.145 m), was added in portions over 45 minutes to a solution of 22.4 g. (0.07 m) of 7-chloro-5-(2-chlorophenyl)-2-methylamine-3H-1,4-benzodiazepin in 150 ml. of glacial acetic acid. After addition stirring was continued for 20 minutes under nitrogen. The product was precipitated by addition of ice-water, collected and dissolved in toluene. The solution was washed with saturated aqueous sodium bicarbonate, dried and evaporated under reduced pressure. The yellow viscous oil (24 g.) consisted according to thin layer chromatogram mainly of the desired nitrosoamidine. This material was dissolved in 100 ml. of dimethylformamide and was added to a mixture of 30 ml. of nitromethane, 100 ml. of dimethylformamide and 10 g. of potassium t-butoxide. The reaction mixture was slowly heated up to 85° with stirring under a nitrogen stream. After 5 minutes, the reaction mixture was cooled, acidified by addition of 10 ml. of glacial acetic acid. The product was crystallized by gradual addition of water with seeding (seeds were obtained by chromatography over silica gel using 10% ethyl acetate in methylene chloride). The separated crystals were collected, washed with water and recrystallized from methylene chloride/ethanol to yield product with m.p. 182°–185°.

EXAMPLE 8

7-Chloro-1,3-dihydro-5-(2-fluorophenyl)-2-nitromethylene-2H-1,4-benzodiazepine

Sodium nitrite, 8.63 g. (0.125 m), was added in three portions over a 15 minute period to a solution of 30.15 g. (0.1 m) of 7-chloro-5-(2-fluorophenyl)-2-methylamino-3H-1,4-benzodiazepine in 150 ml. of glacial acetic acid. After stirring for 1 hour at room temperature the reaction mixture was diluted with water and extracted with methylene chloride. The extracts were washed with saturated sodium bicarbonate solution, were dried over sodium sulfate and evaporated, at the end azeotropically with toluene to yield 29 g. of crude 7-chloro-5-(2-fluorophenyl)-2-(N-nitrosomethylamino)-3H-1,4-benzodiazepine as a yellow oil.

This material was dissolved in 100 ml. of dimethylformamide and added to a mixture of 200 ml. of dimethylformamide, 50 ml. of nitromethane and 11.1 g. (0.1 m) of potassium t-butoxide which had been stirred under nitrogen for 15 minutes.

After stirring for 1 hour at room temperature, the reaction mixture was acidified by addition of glacial acetic acid, was diluted with water and extracted with methylene chloride. The extracts were washed with water, dried over sodium sulfate and evaporated.

Crystallization of the residue from ether yielded product with m.p. 170°–172°. The analytical sample was recrystallized from methylene chloride/ethanol, m.p. 174°–176°.

EXAMPLE 9

7-Bromo-1,3-dihydro-2-nitromethylene-5-(2-pyridyl)-2H-1,4-benzodiazepine

A mixture of 3.6 g. (0.01 m) of 7-bromo-2-(N-nitrosomethylamino)-5-(2-pyridyl)-3H-1,4-benzodiazepine, 30 ml. of dimethylformamide, 5 ml. of nitromethane and 2 g. (0.018 m) of potassium t-butoxide was stirred at room temperature for 15 minutes and then heated up slowly. When the temperature reached 100° the mixture was cooled and neutralized by addition of glacial acetic acid. The product was precipitated by addition of saturated aqueous sodium bicarbonate and was coolected, washed with water and dissolved in methylene chloride. The solution was dried over sodium sulfate and evaporated. Crystallization of the residue from methylene chloride/ethanol yielded a light yellow product with m.p. 232°–235° dec. For analysis it was recrystallized from tetrahydrofuran/ethanol, m.p. 240°–245° dec.

EXAMPLE 10

5-(2-Chlorophenyl)1,3-dihydro-7-nitro-2-nitromethylene-2H-1,4-benzodiazepine

A mixture of 3.58 g. (0.01 m) of 5-(2-chlorophenyl)-7-nitro-2-(N-nitrosomethylamino)-3H-1,4-benzodiazepine, 20 ml. of dimethylformamide, 5 ml. of nitromethane and 1.3 g. (0.0115 m) of potassium t-butoxide was stirred at room temperature for 15 minutes under nitrogen. After addition of 2 ml of glacial acetic acid the reaction mixture was partitioned between methylene chloride and water. The organic phase was washed with water, dried over sodium sulfate and evaporated. The residue was chromatographed over 80 g. of silica gel using 10% (v/v) ethyl acetate in methylene chloride. Crystallization of the clean fractions from methylene chloride/ethanol yielded straw colored crystals with m.p. 240°–243° dec.

EXAMPLE 11

8-Chloro-3a,4-dihydro-1-methyl-6-phenyl-3H-imidazo[1,5-a][1,4]benzodiazepine

Raney nickel (5 teaspoons) was added to a solution of 16.5 g. (0.05 m) of 7-chloro-1,3-dihydro-2-nitromethylene-5-phenyl-2H-1,4-benzodiazepine 4-oxide, in 500 ml. of tetrahydrofuran and 250 ml. of methanol. The mixture was hydrogenated for 5 hours at atmospheric pressure. The catalyst was removed by filtration and the filtrate was evaporated. The residue was dissolved in 2-propanol and the solution was made strongly acidic with ethanolic hydrogen chloride. The dihydrochloride of the product crystallized upon evaporation of part of the solvent. The orange crystals were collected to leave 2-aminomethyl-7-chloro-2,3-dihydro-5-phenyl-1H-1,4-benzodiazepine dihydrochloride with m.p. 230°–240°.

Acetic anhydride, 10 ml. was added to a solution of 10 g. of the above hydrochloride in 50 ml. of water and 50 ml. of methanol. A 10% aqueous solution of sodium carbonate, 100 ml., was added with stirring over a period of 5 minutes. After addition the mixture was stirred for an additional ten minutes and was then extracted with methylene chloride. The extracts were washed with sodium carbonate solution, dried over sodium sulfate and evaporated, at the end azeotropically with toluene. 2-Acetaminomethyl-7-chloro-2,3-dihydro-5-phenyl-1H-1,4-benzodiazepine was obtained as a yellow resin.

The above material was heated in 50 g. of polyphosphoric acid to 135°–140° for 10 minutes. The initially orange color of the reaction mixture faded to a light yellow. The cooled reaction mixture was dissolved in water, made alkaline with concentrated ammonia and ice and extracted with methylene chloride. The extracts were dried and evaporated. The yellow resin was dissolved in 2-propanol and treated with ethanolic hydrogen chloride whereupon the colorless dihydrochloride of the product crystallized. Melting point was 240°–245°.

This hydrochloride was partitioned between methylene chloride and aqueous ammonia. The organic phase was dried and evaporated. Crystallization of the residue from ether yielded a colorless product with m.p. 116°–118°.

EXAMPLE 12

8-Chloro-3a,4-dihydro-1-ethyl-6-(2-fluorophenyl)-3H-imidazo[1,5-a][1,4]benzodiazepine A solution of 16.5 g. (0.05 m) of 7-chloro-1,3-dihydro-5-(2-fluorophenyl)-2-nitromethylene-2H-1,4-benzodiazepine in 500 ml. of tetrahydrofuran and 250 ml. of methanol was hydrogenated with 5 teaspoons of Raney nickel for 2½ hours at atmospheric pressure. Separation of the catalyst and evaporation left 14 g. of crude 2-aminomethyl-7-chloro-2,3-dihydro-5-(2-fluorophenyl)-1H-1,4-benzodiazepine.

Propionic anhydride, 20 ml., was added to a solution of 12 g. of this material in 300 ml. of methylene chloride. The solution was layered with 300 ml. of 10% aqueous sodium carbonate solution and the two phase mixture was stirred at room temperature for 30 minutes. The organic layer was separated, washed with sodium carbonate solution and dried over sodium sulfate. Evaporation yielded crude 7-chloro-2,3-dihydro-5-(2-fluorophenyl)-2-propionylaminomethyl-1H-1,4-benzodiazepine.

This material was heated in 50 g. of polyphosphoric acid at 150°-170° for 10 minutes. The reaction mixture was cooled, dissolved in water and made alkaline with concentrated ammonia and ice. The base was extracted with methylene chloride and the extracts were dried over sodium sulfate and evaporated. The residue was chromatographed over 300 g. of silica gel using 20% methanol in methylene chloride. The clean fractions were combined, evaporated and the residue was crystallized from ether to yield a product with m.p. 131°-133°.

EXAMPLE 13

8-Chloro-1-methyl-6-phenyl-4H-imidazo[1,5-a][1,4]benzodiazepine

A mixture of 3.1 g. (0.01 m) of 8-chloro-3a,4-dihydro-1-methyl-6-phenyl-3H-imidazo[1,5-a][1,4]benzodiazepine, 20 g. of activated manganese dioxide and 150 ml. of toluene was refluxed for 1 hour. The manganese dioxide was removed by filtration over celite and was washed well with methylene chloride. The filtrate was evaporated and the residue was crystallized from ether to yield colorless crystals with m.p. 187°-188°.

EXAMPLE 14

8-Chloro-6-(2-fluorophenyl)-1-methyl-4H-imidazo[1,5-a][1,4]benzodiazepine

Acetic anhydride, 7 ml., was added to a solution of 6.16 g. of crude 2-aminomethyl-7-chloro-2,3-dihydro-5-(2-fluorophenyl)-1H-1,4-benzodiazepine in 200 ml. of methylene chloride. The solution was layered with 200 ml. of saturated aqueous sodium bicarbonate and the mixture was stirred for 20 minutes. The organic layer was separated, washed with sodium bicarbonate, dried over sodium sulfate and evaporated to leave 6.2 g. resinous 2-acetaminomethyl-7-chloro-2,3-dihydro-5-(2-fluorophenyl)-1H-1,4-benzodiazepine. This material was heated with 40 g. of polyphosphoric acid at 150° for 10 minutes. The cooled reaction mixture was dissolved in water, made alkaline with ammonia and ice and extracted with methylene chloride. The extracts were dried and evaporated and the residue (5.7 g.) was chromatographed over 120 g. of silica gel using 20% methanol in methylene chloride. The clean fractions were combined and evaporated to yield resinous 8-chloro-3a,4-dihydro-6-(2-fluorophenyl)-1-methyl-4H-imidazo[1,5-a][1,4]benzodiazepine. A mixture of this material with 500 ml. of toluene and 30 g. of manganese dioxide was heated to reflux for 1½ hours. The manganese dioxide was separated by filtration over celite. The filtrate was evaporated and the residue was crystallized from ether to yield a product with m.p. 152°-154°. The analytical sample was recrystallized from methylene chloride/hexane.

EXAMPLE 15

8-Chloro-6-(2-chlorophenyl)-1-methyl-4H-imidazo[1,5-a][1,4]benzodiazepine

Hydrogenation of 7 g. of 7-chloro-5-(2-chlorophenyl)-1,3-dihydro-2-nitromethylene-2H-1,4-benzodiazepine in 300 ml. of tetrahydrofuran and 150 ml. of methanol in the presence of Raney nickel (5 teaspoonsful) for 1 hour yielded crude 2-aminomethyl-7-chloro-5-(2-chlorophenyl)-2,3-dihydro-1H-1,4-benzodiazepine. This material was acetylated in the usual fashion to leave oily 2-acetaminomethyl-7-chloro-5-(2-chlorophenyl)-2,3-dihydro-1H-1,4-benzodiazepine which was heated in 15 g. of polyphosphoric acid for 10 minutes at 140°-150°. The usual workup afforded a yellow resin which was chromatographed over 250 g. of silica gel using 20% methanol in methylene chloride.

The clean fractions left 1.3 g. of resinous 8-chloro-6-(2-chlorophenyl)-3a,4-dihydro-1-methyl-4H-imidazo[1,5-a][1,4]benzodiazepine. This material was oxidized with 10 g. of manganese dioxide in 200 ml. of toluene. After heating to reflux for 1½ hour, the manganese dioxide was separated and the filtrate was evaporated. Crystallization of the residue from ether yielded a product with m.p. 140°-144°. For analysis it was recrystallized from methylene chloride/hexane, m.p. 142°-144°.

EXAMPLE 16

8-Chloro-1-ethyl-6-(2-fluorophenyl)-4H-imidazo[1,5-a][1,4]benzodiazepine

A mixture of 3.4 g. of 8-chloro-3a,4-dihydro-1-ethyl-6-(2-fluorophenyl)-4H-imidazo[1,5-a][1,4]benzodiazepine, 400 ml. toluene and 30 g. activated manganese dioxide was refluxed with separation of water in a Dean-Stark trap for 2 hours. The manganese dioxide was separated by filtration over celite and the filtrate was evaporated. Crystallization of the residue from ether yielded a product with m.p. 140°-143°. For analysis it was recrystallized from ether, m.p. 143°-145°.

EXAMPLE 17

7-Chloro-1,3-dihydro-5-(2-fluorophenyl)-2-(1-nitroethylene)-2H-1,4-benzodiazepine A mixture of 11.2 g (0.1 m) of potassium tert. butoxide, 50 ml of nitroethane and 200 ml of dimethylformamide was stirred at room temperature for 15 min. A solution of 29 g (0.088 m) of crude 7-chloro-5-(2-fluorophenyl)-2-(N-nitrosomethylamino)-3H-1,4-benzodiazepine in 100 ml of dimethylformamide was then added and stirring under nitrogen was continued for 6 hrs. The reaction mixture was neutralized by addition of glacial acetic acid and diluted with water. The product was extracted with ether. The extracts were washed with saturated aqueous sodiumbicarbonate solution, dried over sodium sulfate and evaporated. Crystallization from ether yielded a final product as yellow crystals with mp 136°-142°.

EXAMPLE 18

8-Chloro-1,3-dimethyl-6-(2-fluorophenyl)-4H-imidazo[1,5-a][1,4]benzodiazepine and
8-Chloro-1,4-dimethyl-6-(2-fluorophenyl)-4H-imidazo[1,5-a][1,4]benzodiazepine Raney nickel, 5 teaspoonsful, was added to a solution of 17.3 g (0.05 m) of 7-chloro-1,3-dihydro-5-(2-fluorophenyl)-2-(1-nitroethylene)-2H-1,4-benzodiazepine in 750 ml of tetrahydrofuran. The mixture was hydrogenated at atmospheric pressure for 4 hrs. The catalyst was removed by filtration over celite and was washed well with methanol. The filtrate was evaporated to leave crude 2-(1-aminoethyl)-7-chloro-2,3-dihydro-5-(2-fluorophenyl)-1H-1,4-benzodiazepine as a reddish oil. This material was dissolved in 300 ml of methylene chloride. Following the addition of 14 ml of acetic anhydride, 300 ml of saturated aqueous sodium bicarbonate solution was added and the two-phase mixture was stirred at room temperature for 1 hr. The methylene chloride layer was separated, washed with bicarbonate, dried over sodium sulfate and evaporated. The residue, 13.5 g, was heated with 40 g of polyphosphoric acid for 10 minutes at 160°–170°. The cool reaction mixture was diluted with water, made alkaline with ammonia and extracted with methylene chloride. The extracts were washed with water, dried and evaporated to leave 11 g of a brown residue which was chromatographed on 250 g of silica gel using 20% (v/v) methanol in methylene chloride. The thin layer chromatographically homogeneous fractions were combined to yield a resin which was subjected to the following oxidation.

A mixture of the above material, 20 g of activated manganese dioxide and 300 ml of toluene was heated to reflux for 3 hrs using a Dean-Stark trap to remove the water. The manganese dioxide was separated by filtration over celite and was washed well with methylene chloride. The filtrate was evaporated and the residue, 4.2 g, was chromatographed with pressure over 150 g of silica gel H using 3% ethanol in methylene chloride. The first eluted major component was 8-chloro-1,4-dimethyl-6-(2-fluorophenyl)-4H-imidazo[1,5-a][1,4]benzodiazepine.

It was converted to a crystalline dihydrochloride by treatment with ethanolic hydrogen chloride in ether. Mp 247°–250° dec.

The more polar component could be crystallized from methylene chloride/ether/hexane to yield 8-chloro-1,3-dimethyl-6-(2-fluorophenyl)-4H-imidazo[1,5-a][1,4]benzodiazepine with mp. 178°–180°.

EXAMPLE 19

8-Chloro-1-methyl-6-phenyl-4H-imidazo[1,5-a][1,4]benzodiazepine 5-oxide

A mixture of 3.1 g (0.01 m) of 8-chloro-1-methyl-6-phenyl-4H-imidazo[1,5-a][1,4]benzodiazepine, 2.15 g (0.0125 m) of m-chloroperbenzoic acid and 100 ml of methylene chloride was stirred for 48 hrs. at room temperature. It was then washed with 10% aqueous sodium carbonate solution and water. The methylene chloride layer was dried over sodium sulfate and evaporated. The residue was chromatographed over 80 g of silica gel using 10% (v/v) of ethanol in methylene chloride. The Tlc-homogeneous fractions were combined and evaporated. Crystallization of the residue from methylene chloride/ether yielded a final product with mp 260°–261°.

EXAMPLE 20

4-Acetoxy-8-chloro-1-methyl-6-phenyl-4H-imidazo[1,5-a][1,4]benzodiazepine

A solution of 1 g of 8-chloro-1-methyl-6-phenyl-4H-imidazo[1,5-a][1,4]benzodiazepine 5-oxide in 20 ml of acetic anhydride was heated on the steam bath for 24 hrs. The reagent was evaporated under reduced pressure and the residue was crystallized from ether to yield a final product with mp 200°–201°.

EXAMPLE 21

8-Chloro-4-hydroxy-1-methyl-6-phenyl-4H-imidazo[1,5-a][1,4]benzodiazepine

Sodium methoxide, 0.54 g, was added to a solution of 0.73 g (2 mmol) of 4-acetoxy-8-chloro-1-methyl-6-phenyl-4H-imidazo[1,5-a][1,4]benzodiazepine in 20 ml of methanol. After sitting at room temperature for 30 min, the solvent was evaporated under reduced pressure after neutralization with acetic acid. The residue was partitioned between methylene chloride and sodium bicarbonate solution. The organic layer was dried over sodium sulfate and evaporated. Crystallization of the residue from ether yielded a final product with mp 173°–174°.

EXAMPLE 22

8-Choro-6-(2-fluorophenyl)-1-methyl-4H-imidazo[1,5-a][1,4]benzodiazepine maleate A warm solution of 6.5 g (0.02 m) of 8-chloro-6-(2-fluorophenyl)-1-methyl-4H-imidazo[1,5-a][1,4]benzodiazepine in 30 ml of ethanol was combined with a warm solution of 2.6 g (0.022 m) of maleic acid in 20 ml of ethanol. The mixture was diluted with 150 ml of ether and heated on the steam bath for 3 min. After cooling, the crystals were collected, washed with ether and dried in vacuo to yield a final product with mp 148°–151°.

EXAMPLE 23

A mixture of 17.4 g (0.05 m) of 7-chloro-1,3-dihydro-5-(2-fluorophenyl)-2-(1-nitromethylene)-2H-1,4-benzodiazepine 4-oxide, 500 ml of tetrahydrofuran, 200 ml of methanol and 5 teaspoonful of Raney nickel was hydrogenated at atmospheric pressure for 5 hrs. The catalyst was removed by filtration and the filtrate was evaporated at the end azeotropically with xylene to leave crude 2-aminomethyl-7-chloro-5-(2-fluorophenyl)-2,3-dihydro-1H-1,4-benzodiazepine.

This material was dissolved in 200 ml of ethanol and the solution was heated to reflux for 2 hrs. after addition of 14 ml of triethylorthoacetate and 2.8 g of p-toluenesulfonic acid. The solvent was evaporated under reduced pressure and the residue was partitioned between methylene chloride and 10% aqueous sodium carbonate solution. The organic layer was dried and evaporated to yield oily 8-chloro-3a,4-dihydro-6-(2-fluorophenyl)-1-methyl-3H-imidazo[1,5-a][1,4]benzodiazepine. This crude product was dissolved in 500 ml of xylene. After addition of 50 g of activated manganese dioxide, the mixture was stirred and heated to reflux for 1½ hrs with separation of water in a Dean-Stark trap. The inorganic material was removed by filtration and the filtrate was evaporated to leave 10 g of brown oil.

A warm solution of 4.65 g (0.04 m) of maleic acid in 50 ml of ethanol was added to this residue. After the solution was complete, the product was crystallized by addition of ether. It was collected and washed with ether to leave the maleate of Example 22 with mp 112°–115°. Heating under vacuum at 90° to 100° converts this product to the higher melting form, i.e. M.P.=148°–151°.

EXAMPLE 24

8-Chloro-6-(2-fluorophenyl)-1-methyl-4H-imidazo[1,5-a][1,4]benzodiazepine dihydrochloride A solution of 0.32 g (1 mmol) of 8-chloro-6-(2-fluorophenyl)-1-methyl-4H-imidazo[1,5-a][1,4]benzodiazepine in 5 ml of ethanol was treated with excess ethanolic hydrogen chloride. The salt was crystallized by addition of 2-propanol and ether. The colorless crystals were collected, washed with ether and dried to leave a final product with mp 290°–295°.

EXAMPLE 25

8-Chloro-6-(2-fluorophenyl)-1-methyl-4H-imidazo[1,5-a][1,4]benzodiazepine hydrochloride A solution of 0.325 g (1 mmol) of 8-chloro-6-(2-fluorophenyl)-1-methyl-4H-imidazo[1,5-a][1,4]benzodiazepine in 3 ml of ethanol was combined with a suspension of 0.4 g (1 mmol) of the dihydrochloride of this compound in 5 ml of ethanol. After filtration, the solution was treated with ether and heated on the steambath for 5 min to crystallize. The crystals were collected, washed with ether and dried to leave the monohydrochloride with mp 295°–297°.

EXAMPLE 26

1,3-Dihydro-2-nitromethylene-5-phenyl-2H-1,4-benzodiazepine

To a cooled (10°), stirred solution of 10.0 g (0.04 m) of 2-methylamino-5-phenyl-3H-1,4-benzodiazepine in 100 ml of pyridine was added 100 ml of a saturated solution of nitrosyl chloride in acetic anhydride. The solution was stirred for 3.5 hr. during which time it was allowed to warm to ambient temperature. The solution was poured into 300 ml of ice-water, and the aqueous solution was extracted with five 150-ml portions of methylene chloride. The combined organic extracts were washed with water and brine, dried (CaSO$_4$), and the solvent removed under reduced pressure affording 11.7 g of a dark semi-solid. Chromatography on 500 g of silica gel (chloroform elution) afforded the 2-(N-nitrosomethylamino)-5-phenyl-3H-1,4-benzodiazepine, mp 192°–199° dec. This material was used in the following step:

The conjugate base of nitromethane was prepared by treatment of 50 ml of nitromethane in 200 ml of DMF with 5.7 g (0.05 m) of potassium tert-butoxide. The resultant stirred yellow suspension was treated with 10.9 g of crude 2-(N-nitrosomethylamino)-5-phenyl-3H-1,4-benzodiazepine in 100 ml of DMF. The dark mixture thus obtained was stirred for 2 hrs. at 25° and for 1 hr at 85° and then cooled to 25° and poured onto 1 l. of water. After acidification with acetic acid, the aqueous solution was extracted with four 250-ml portions of methylene chloride, and the combined organic extracts were then washed with water and brine, dried (CaSO$_4$), and concentrated in vacuo to give a dark oil which was purified by chromatography over 1 kg. of silica gel (CHCl$_3$ elution) to afford crude product, mp 131°–142°.

An analytical sample, mp 141°–142°, was prepared by recrystallization from ethanol.

EXAMPLE 27

1-Methyl-6-phenyl-4H-imidazo[1,5-a][1,4]benzodiazepine

A mixture of 8.4 g (0.03 m) of 1,3-dihydro-2-nitromethylene-5-phenyl-2H-1,4-benzodiazepine, 75 ml of tetrahydrofuran, 75 ml of methanol and 2 teaspoonsful of Raney nickel was hydrogenated at atmospheric pressure for 6 hrs. The catalyst was removed by filtration and the filtrate was evaporated to leave crude 2-aminomethyl-2,3-dihydro-5-phenyl-1H-1,4-benzodiazepine.

This material was dissolved in 50 ml of methylene chloride and was treated with 6 ml of acetic anhydride and 200 ml of saturated aqueous sodium bicarbonate solution for 15 min. with stirring. The methylene chloride layer was separated, washed with bicarbonate solution, dried and evaporated. The residue was treated with 25 g of polyphosphoric acid to 130°–150° for 15 min. The cooled reaction mixture was partitioned between water and ether. The aqueous phase was made alkaline with ammonia and was extracted with methylene chloride. The extracts were dried and evaporated. Chromatography of the residue over 70 g of silica gel with 20% (v/v) ethanol in methylene chloride yielded 3a, 4-dihydro-1-methyl-6-phenyl-3H-imidazo[1,5-a][1,4]benzodiazepine as a light yellow resin.

This material was heated in 50 ml of toluene with 7 g of activated manganese dioxide to reflux for 1½ hrs. The inorganic material was filtered off and the filtrate was evaporated. The residue was purified by chromatography over 30 g of silica gel using 10% ethanol in methylene chloride. The clean fractions were combined and evaporated. Crystallization of the residue from ether yielded a final product with mp 180°–182°.

EXAMPLE 28

2-Aminomethyl-7-chloro-2,3-dihydro-5-(2-fluorophenyl)-1H-1,4-benzodiazepine dimaleate A suspension of 17 g (0.05 m) of 7-chloro-1,3-dihydro-5-(2-fluorophenyl)-2-nitromethylene-2H-1,4-benzodiazepine-4-oxide in 200 ml of tetrahydrofuran and 100 ml of methanol was hydrogenated in presence of 17 g of Raney nickel at an initial pressure of 155 psi for 24 hrs. The catalyst was removed by filtration and the filtrate was evaporated. The residue was dissolved in 50 ml of 2-propanol and warmed on the steambath. A warm solution of 17 g of maleic acid in 60 ml of ethanol was added and the salt was allowed to crystallize by cooling in the ice bath. The final product consisted of yellow crystals with mp 196°–198°.

EXAMPLE 29

7-Chloro-2-di-(morpholino)-phosphinyloxy-5-(2-fluorophenyl)-3-methyl-3H-1,4-benzodiazepine To a stirred solution of 6 g. (0.02 m) of 7-chloro-1,3-dihydro-5-(2-fluorophenyl)-3-methyl-2H-1,4-benzodiazepin-2-one in 100 ml of dry tetrahydrofuran was added 1.05 g, (0.25 m) of 57% sodium hydride dispersion in mineral oil. The mixture was placed under argon and refluxed for 1 hr. After cooling to room temperature, the mixture was treated with 7.4 g (0.03 m) of dimorpholinophosphinic chloride and stirring under argon was continued at room temperature for 2 hrs. The mixture was filtered and evaporated at reduced pressure to give a gummy residue. Stirring the gum with 100 ml of anhydrous ether gave white crystals which were collected by filtration, washed with a little ether and air dried. The final product had a m.p. of 90°–95°.

EXAMPLE 30

7-Chloro-1,3-dihydro-5-(2-fluorophenyl)-3-methyl-2-nitro methylene-2H-1,4-benzodiazepine A stirred solution of 2.4 g (0.04 m) of nitromethane in 50 ml of dry dimethylformamide was treated with 1 g (0.024 m) of 57% sodium hydride dispersion in mineral oil at room temperature under argon. After stirring for 1 hr. at room temperature, the mixture was treated with 5.2 g (0.01 m) of 7-chloro-2-di(-morpholino)-phosphinyloxy-5-(2-fluorophenyl)-3-methyl-3H-1,4-benzodiazepine in one portion and stirring under argon was continued at room temperature for 24 hrs. The dark mixture was poured over a mixture of ice and glacial acetic acid with stirring to give a yellow solid. Stirring was continued until the ice had melted. The solid was filtered, washed with water and air dried on the funnel to yield a product having mp of 215° dec. Recrystallization of a sample from 1:1 methanolmethylene chloride solution gave yellow needles, mp 219°–221° dec.

EXAMPLE 31

8-Chloro-1,4-dimethyl-6-(2-fluorophenyl)-4H-imidazo[1,5-a][1,4]benzodiazepine Dihydrochloride A solution of 5.2 g (0.015 m) of 7-chloro-1,3-dihydro-5-(2-fluorophenyl)-3-methyl-2-nitromethylene-2H-1,4-benzodiazepine in 450 ml of 2:1 tetrahydrofuran-methanol was hydrogenated for 3 hrs. using a Parr apparatus, Raney nickel catalyst (3 teaspoonsful) and an initial pressure of 18 psi. The mixture was filtered and evaporated at reduced pressure to give crude 2-aminomethyl-7-chloro-2,3-dihydro-5-(2-fluorophenyl)-3-methyl-1H-1,4-benzodiazepine as a yellow oil.

The crude aminomethyl compound was mixed with 5 ml of triethyl orthoacetate, and 0.5 g of p-toluenesulfonic acid monohydrate in 100 ml of ethanol. After heating under reflux for 2 hrs, the solution was evaporated at reduced pressure. The residue was cooled to room temperature, treated with a mixture of ice and concentrated ammonium hydroxide and extracted with methylenechloride. Evaporation of the dried extracts in vacuo gave crude 8-chloro-3a,4-dihydro-1,4-dimethyl-6-(2-fluorophenyl)-3H-imidazo[1,5-a][1,4]benzodiazepine as a gum.

The crude dihydroimidazobenzodiazepine was mixed with 20 g of activated manganese dioxide and 200 ml of toluene and heated under reflux for 2 hrs. The mixture was filtered and the manganese dioxide was washed with methylene chloride. Evaporation of the combined filtrate and washings at reduced pressure gave a brown gum. The dihydrochloride of the product was obtained as a white powder by stirring the gum with ethanolic hydrogen chloride for a few minutes. The salt melted at 247°–250°.

EXAMPLE 32

8-Chloro-5,6-dihydro-6-(2-fluorophenyl)-1-methyl-4H-imidazo[1,5-a][1,4]benzodiazepine Zinc dust, 3 g, was added to a solution of 2.8 g of 8-chloro-6-(2-fluorophenyl)-1-methyl-4H-imidazo[1,5-a][1,4]benzodiazepine in 75 ml of methylene chloride and 75 ml of glacial acetic acid. After stirring at room temperature for 2 hrs, the inorganic material was filtered off and washed with methylene chloride and water.

The filtrate was diluted with 100 ml of methylene chloride and 200 ml of water and was made alkaline with ammonia. The methylene chloride layer was separated, dried and evaporated. Crystallization of the residue from ether/hexane yielded a final product with mp 200°–203°.

EXAMPLE 33

6-Chloro-2-(1,1-dichloroethyl)-1,2-dihydro-4-(2-fluorophenyl)quinazoline 3-oxide A mixture of 49.9 (0.2 moles) of 2-amino-5-chloro-2'-fluorobenzophenone, 38.0 g (0.3 moles) of 2,2-dichloro propanal; 18.0 g (0.11 moles) of hydroxylamine sulfate and 500 ml of 2B ethanol was stirred at room temperature for 2 days.

The mixture was diluted with 200 ml of 10% aqueous Na2CO3 solution with vigorous agitation. A gummy material precipitated from solution and the solution was diluted with 1.0 l of ice-water. The solution was extracted with 3×300 ml. of dichloromethane. The extracts were combined, dried over Na2SO4; filtered and concentrated to dryness in vacuo. The residue was crystallized from dichloro methane and petroleum ether giving 6-chloro-2-(1,1-dichloroethyl)-1,2-dihydro-4-(2-fluorophenyl) quinazoline 3-oxide as yellow prisms, m.p. 195°–198° dec.

EXAMPLE 34

7-Chloro-1,3-dihydro-5-(2-fluorophenyl)-3-methyl-2-nitromethylene-2H-1,4-benzodiazepine 4-oxide 3.8 ml of Nitromethane was added to 50.0 ml of dimethylformamide with stirring and under an atmosphere of nitrogen. The solution was chilled to 0° and 1.3 g (0.012 mols) of potassium tertiary butoxide was added in portions. The temperature was maintained at 0° to 10° by means of an ice-H2O bath. The mixture was stirred at room temperature for 1 hour.

The mixture was chilled to 5° with stirring and 2.2 g (0.006 moles) of the quinazoline of Example 33 was added at 5° to 9° in portions. After the addition had been completed, the mixture was stirred at room temperature for 17 hours.

The reaction mixture was poured into ice-H2O and dichloromethane neutralizing with glacial acetic acid. The dichloromethane was washed with water; brine and dried over Na2SO4. After filtration and concentration an amber residue was obtained which was crystallized with EtOAc. The crystals were collected and dried giving orange 7-chloro-1,3-dihydro-5-(2-fluorophenyl)-3-methyl-2-nitromethylene-2H-1,4-benzodiazepine 4-oxide as prisms, m.p. 198°–200°. Recrystallization from CH2Cl2-EtOAc gave pure material m.p. 216°–218° dec.

EXAMPLE 35

7-Chloro-1,3-dihydro-2-nitromethylene-5-phenyl-2H-1,4-benzodiazepine 4-oxide 9.5 ml of Nitromethane was dissolved in 100 ml of dimethylformamide under nitrogen and with stirring. 5.0 g (0.045 moles) of potassium tertiary butoxide was added at 0°–10° and the mixture was stirred at room temperature for 1 hour. The mixture was then chilled on ice and 5.1 g (0.015 moles) of 6-chloro-2-dichloromethyl-1,2-dihydro-4-phenylquinazoline 3-oxide was added slowly at a temperature <9°. The reaction mixture was stirred at room temperature for 17 hours.

The mixture was poured onto ice-H2O and dichloromethane and made slightly acid with glacial acetic acid. The aqueous phase was re-extracted three times with dichloromethane. The organics were combined; washed consecutively with water and brine, dried over Na2SO4; filtered and concentrated to dryness in vacuo giving an amber residue. Crystallization from boiling ethanol afforded yellow prisms, mp 245°–248° dec. Admixture with authentic material gave no depression in melting point.

EXAMPLE 36

7-Chloro-1,3-dihydro-5-(2-fluorophenyl)-3-methyl-2-nitromethylene-2H-1,4-benzodiazepine 4-oxide Potassium tert. butoxide, 3.37 g (0.03 m), was added to a stirred suspension of 3.5 g (0.01 m) of 7-chloro-1,3-dihydro-5-(2-fluorophenyl)-2-nitromethylene-2H-1,4-benzodiazepine 4-oxide in 100 ml of dimethylformamide cooled at −20°. After stirring under nitrogen for 10 min at this temperature 2.13 g (0.015 m) of methyliodide was added and stirring was continued for 10 min. The reaction mixture was neutralized by addition of glacial acetic acid and was partitioned between water and methylene chloride. The organic phase was separated, dried over sodium sulfate and evaporated. The residue was crystallized from methylene chloride/ethyl acetate to yield yellow crystals with mp 215°–218°. The analytical sample was recrystallized from the same solvents, mp 216°–218°.

EXAMPLE 37

2-Aminomethyl-7-chloro-2,3-dihydro-5-(2-fluorophenyl)-1H-1,4-benzodiazepine dimaleate A mixture of 7-chloro-1,3-dihydro-5-(2-fluorophenyl)-2H-1,4-benzodiazepine-2-carboxamide (64 mg., 0.2 mmole) and lithium aluminum hydride (15 mg., 0.4 mmole) in dry THF (3 ml) was boiled for 15 min. The cooled reaction mixture was quenched by addition of saturated aqueous sodium sulfate solution. The analysis of the resulting solution showed the presence of starting material as the major, more mobile component and the free base 2-aminomethyl-7-chloro-2,3-dihydro-5-(2-fluorophenyl)-1H-1,4-benzodiazepine as the minor component. The solution was transferred directly to a 20×20 cm$^2$ preparative tlc plate (silica gel) and the plate was developed with ethanol. The lower yellow band was removed and extracted twice with methanol/methylene chloride (2:1). Evaporation of the filtered extract left a clear, colorless oil. This was taken up in ethanol (1 ml), treated with excess maleic acid (50 mg), scratched and stored overnight in the freezer. The yellow crystals were collected, washed with ether and air-dried. The product was identified as 2-aminomethyl-7-chloro-2,3-dihydro-5-(2-fluorophenyl)-1H-1,4-benzodiazepine dimaleate by comparison of its infrared spectrum in Nujol, and of its melting point 185°–186.5° with those of an authentic sample (mp 188°). The mixture melting point was 184°–187°.

EXAMPLE 38

2-Aminomethyl-2,3-dihydro-5-(2-fluorophenyl)-1H-1,4-benzodiazepine dimaleate hemihydrate A solution of 2.9 g. (0.00927 M) of 2,3-dihydro-5-(2-fluorophenyl)-2-nitromethylene-1H-1,4-benzodiazepine 4-oxide in a mixture of 1 teaspoon of Raney nickel, 90 ml. of tetrahydrofuran and 45 ml. of methanol was hydrogenated at atmospheric pressure and at room temperature for 2.3 hr. The mixture was filtered, and the nickel was washed with dichloromethane. The combined filtrates were evaporated and the resulting oil was dissolved in 50 ml. of dichloromethane which was washed with 50 ml. of dilute ammonium hydroxide, dried over anhydrous sodium sulfate and evaporated to dryness. A solution of 2.2 g. (0.019 M) of maleic acid in 15 ml. of ethanol was added to the oil and after ether was added the product crystallized. Recrystallization from a mixture of methanol and ether gave a product as yellow rods, m.p. 147°–150°.

EXAMPLE 39

3a,4-Dihydro-6-(2-fluorophenyl)-1-methyl-3H-imidazo[1,5a][1,4]benzodiazepine

A solution of 4.0 g. (0.0149 M) of the base of 2-aminomethyl-2,3-dihydro-5-(2-fluorophenyl)-1H-1,4-benzodiazepine dimaleate hemihydrate in 125 ml. of absolute ethanol was treated with 4 g. (0.0247 M) of triethylorthoacetate and 0.5 g. (0.00263 M) of p-toluene sulfonic acid. After refluxing the mixture for 2 hr. the reaction was evaporated to dryness. The resulting oil was dissolved in 50 ml. of dichloromethane, which was washed with 50 ml. of dilute ammonium hydroxide, dried over anhydrous sodium sulfate and evaporated to dryness to yield the crude product as an oil.

EXAMPLE 40

6-(2-Fluorophenyl)-1-methyl-4H-imidazo-[1,5a][1,4]benzodiazepine

The crude product from the previous example was dissolved in 100 ml. of toluene, treated with 18 g. of activated manganese dioxide and the mixture was stirred and refluxed for 3.5 hr. using a Dean Stark trap. The reaction mixture as filtered through Celite and the precipitate was washed with 100 ml. of tetrahydrofuran and then 100 ml. of dichloromethane. The combined filtrates were evaporated and the residue was dissolved in 25 ml. of dichloromethane. This solution was chromatographed through a Florisil column with dichloromethane, and then eluted with ether. Elution with ethyl acetate and then a 10% (v/v) solution of methanol in ethyl acetate gave the crude product, which was crystallized from ether and then recrystallized from ethyl acetate to give the product as white prisms, m.p. 164°–168°.

EXAMPLE 41

A solution of 1.2 g. (0.0041 M) of 3a,4-dihydro-6-(2-fluorophenyl)-1-methyl-3H-imidazo[1,5-a][1,4]benzodiazepine in 50 ml. of mesitylene and 0.5 g. of 10% palladium on charcoal was stirred and refluxed for 28 hr., and then it was filtered and evaporated to dryness. Crystallization from ethyl acetate gave the product of Example 40 as white prisms, m.p. 162°–167°, and a mixed m.p. with authentic product melted at 162°–168°.

EXAMPLE 42

6-(2-Fluoro-5-nitrophenyl)-1-methyl-4H-imidazo[1,5a][1,4]benzediazepine

A solution of 0.3 g. (0.00103 M) of 6-(2-fluorophenyl)-1-methyl-4H-imidazo[1,5-a][1,4]benzodiazepine in 2 ml. of concentrated sulfuric acid was cooled to 0°, and a solution of 0.11 g. (0.0011 M) of potassium nitrate in 1.5 ml. of concentrated sulfuric acid was added dropwise. After 18 hr. at room temperature an additional 20 mg. (0.0002 M) of potassium nitrate was added and the reaction was stirred for 5 hr. and then poured into a beaker containing ice. The mixture was made basic with ammonium hydroxide, and extracted with 50 ml. of dichloromethane which was separated, dried over anhydrous sodium sulfate, and evaporated to dryness. The oil was dissolved in 3 ml. of dichloromethane and applied to a silica gel thick layer plate which was developed in a mixture of ethyl acetate and ethanol (3:1). The product was scraped off the plate and stirred with a 1:1 (v/v) mixture of methanol and dichloromethane and filtered. The filtrates were evaporated and the residue was crytallized from methanol. Recrystallization of the product from a mixture of dichloromethane and petroleum ether gave the nitrated product a white prisms, m.p. 199°–203°.

EXAMPLE 43

2-Chloromethyl-4-(2-fluorophenyl)-6-nitro-1,2-dihydroquinazoline 3-oxide

A mixture of 100 g. (0.8 m) of chloroacetaldehyde dimethylacetal and 100 ml. of 1.5 N hydrochloric acid was heated under reflux for 15 min. and then cooled and added to a solution of 130 g. (0.5 m) of 2-amino-2'-fluoro-5-nitrobenzophenone and 46 g. (0.28 m) of hydroxylamine sulfate and 1 l. of ethanol. The mixturewas stirred at room temperature for 2 hr. and then heated to reflux for 1.5 hr. The mixture was cooled and the product obtained by filtration. Recrystallization from a mixture of chloroform and methanol gave the pure product as yellow prisms, m.p. 220°–224°.

EXAMPLE 44

2-Chloromethyl-4-(2-fluorophenyl)-6-nitroquinazoline 3-oxide

A solution of 142 g. (0.423 m) of 2-chloromethyl-4-(2-fluorophenyl)-6-nitro-1,2-dihydroquinazoline 3-oxide in 2.3 l. of dichloromethane was treated with 400 g. of manganese dioxide, and after stirring for 18 hr. the solution was filtered. The manganese dioxide was washed with 600 ml. of tetrahydrofuran and 600 ml. of dichloromethane. The combined filtrates were concentrated to 400 ml. and 1 l. of ether was added. This was cooled and filtered to give a final product. A sample ws recrystallized from a mixture of dichloromethane and methanol to give the pure product as pale yellow prisms, m.p. 127°–130°.

EXAMPLE 45

1,3-Dihydro-5-(2-fluorophenyl)-7-nitro-2-nitromethylene-2H-1,4-benzodiazepine 4-oxide To 500 ml. of dimethylsulfoxide and 75 ml. (1.4 m) of nitromethane was added with stirring under nitrogen 15.6 g. (0.678m) of lithium amide. After 30 minutes the solution was cooled to 5° C. and 104 g. (0.31 m) of 2-chloromethyl-4-(2-fluorophenyl)-6-nitroquinazoline 3-oxide was added slowly, keeping the temperature below 8° C. After 68 hr. at room temperature the reaction was poured into a mixture of 2.5 l. of ice and water and 25 ml. of acetic acid, and the solution was filtered. The gummy precipitate was dissolved in 1 l. of dichloromethane which was washed with dilute ammonium hydroxide, dried over anhydrous sodium sulfate and evaporated. The residue was crystallized from ethyl acetate to give a final product, and the filtrates were evaporated, dissolved in dichloromethane and filtered through a sintered glass funnel containing 200 g. of Florisil. The Florisil was eluted with dichloromethane (600 ml.), ether (600 ml.) and ethyl acetate (1.2 l.). The ether and ethyl acetate fractions were combined and concentrated to give additional final product. A sample was recrystallized from a mixture of tetrahydrofuran and hexane to give the pure product as yellow prisms, m.p. 216°–220°.

EXAMPLE 46

8-Amino-6-(2-fluorophenyl)-1-methyl-4H-imidazo-[1,5-a][1,4]benzodiazepine isopropanolate A suspension of 25 g. (0.0698 m) of 1,3-dihydro-5-(2-fluorophenyl)-7-nitro-2-nitromethylene-2H-1,4-benzodiazepine 4-oxide in 1.3 l. of absolute ethanol was treated with 10 teaspoons of Raney nickel and hydrogenated at atmospheric pressure and room temperature for 9 hr. The mixture was filtered through Celite and the filtrate was evaporated to dryness. A sample of the oil was crystallized from tetrahydrofuran to give the intermediate 7-amino-2-aminomethyl-1,3-dihydro-5-(2-fluorophenyl)-2H-1,4-benzodiazepine as yellow prisms which melted with decomposition at 185°–192°.

Without further purification, the oil obtained from the reduction was heated under reflux for 2 hr. in a solution of 300 ml. of absolute ethanol, containing 4.5 ml. (0.0257 m) of ethanolic hydrogen chloride and 50 g. (0.309 m) of triethylorthoacetate. The mixture was then evaporated to dryness and the residue was dissolved in 150 ml. of dichloromethane which was wshed with 100 ml. of dilute ammonium hydroxide, dried over anhydrous sodium sulfate and evaporated to dryness.

The residual oil, which was crude 8-acetylamino-3a,4-dihydro-6-(2-fluorophenyl)-1-methyl-3H-imidazo[1,5-a][1,4]benzodiazeine, was dissolved in 500 ml. of benzene and treated with 100 g. of activated manganese diode. The mixture was refluxed and stirred for 9 hr. using a Dean Stark trap. An additional 25 g. of activated manganese dioxide was added and after 4 hr. of refluxing the manganese dioxide was removed by filtration and was washed with 500 ml. of tetrahydrofuran. The filtrates were combined and evaporated to dryness. The residual oil, which was 8-acetylamino-6-(2-fluorophenyl)-1-methyl-4H-imidazo-[1,5-a][1,4]benzodiazepine, was dissolved in 75 ml. of methanol and an excess of ethanolic hydrogen chloride was added. After 10 min. 100 ml. of water was added, and after an additional 20 min, during which time the 8-acetyl group was hydrolyzed, a mixture of ice and dilute ammonium hydroxide was added until the solution was basic. The reaction was filtered and the precipitate and filtrates were extracted separately with dichloromethane. The extracts were dried, and evaporated. The extract from the filtrates were crystallized from isopropanol to give a final product, and the extract from the precipitate was chromatographed through Florisil, first with dichloromethane and then with ether and ethyl acetate containing 10% (v/v) of methanol gave, after evaporation and crystallization from isopropranol, additional product. Recrystallization of the combined products from isopropanol gave the isopropanolate as white rods, m.p. 135°–145°.

EXAMPLE 47

(+)-8-Chloro-1,4-dimethyl-6-(7-fluorophenyl)-4H-imidazo[1,5-a][1,4]-benzodiazepine 1-tartrate A mixture of 17 g. (0.05 m) of racemic 8-chloro-1,4-dimethyl-6-(2-fluorophenyl)-4H-imidazo[1,5-a][1,4]

benzodiazepine which had been liberated from its dihydrochloride by partitionining between methylene chloride and aqueous ammonia, 18.8 g. (0.05 m) of O,O'-dibenzoyl-d-tartaric acid hydrate and 170 ml. of ethanol was boiled until solution was complete. For crystallization the solution was allowed to sit overnight. The separated crystals were collected, washed with ethanol and ether to yield product with m.p. 140°–142°. Recrystallization from ethanol/ether yielded product with m.p. 141°–142° and $[\alpha]_D^{25}$ −43.39 (c=1% in methanol).

A solution of 1.6 g. (0.0106 m) of 1-tartaric acid in 11 ml. of ethanol was added to a solution of 3.5 g. of the levorotatory base liberated from the above O,O'-dibenzoyl-d-tartrate in 11 ml. of ethanol. The crystals obtained were collected and washed with ethanol and ether to yield product with m.p. 178°–180°. Recrystallization from ethanol gave product with m.p. 183°–185° and $[\alpha]_D^{25}$ +25.69° (c=1.012% in methanol). The amorpous base liberated from this salt showed a rotation of $[\alpha]_D^{25}$ −36.74° (c=0.939% in methylene chloride).

EXAMPLE 48

(−)-8-Chloro-1,4-dimethyl-6-(1-fluorophenyl)-4H-imidazo[1,5-a][1,4]benzodiazepine d-tartrate The mother liquor left after separation of the crystalline salt with O,O'-dibenzoyl-d-tartaric acid described in the preceding example was evaporated and recovered to the base by partitioning between aqueous ammonia and methylene chloride. The methylene chloride solution was dried over sodium sulfate and evaporated to yield 12 g. of partly resolved base.

A solution of 9.7 g. (0.029 m) of this material in 15 ml. of ethanol was treated with a solution of 4.4 g. of d-tartaric acid in 14 ml. of ethanol. The crystals which separated after several hours were collected to yield product with m.p. 176°–178°. Recrystallization from ethanol gave product with m.p. 182°–184° and $[\alpha]_D^{25}$ −24.96° (0.9616% in methanol). The amorphous base liberated from this salt showed a rotation of $[\alpha]_D^{25}$ +37.6° (c=1.0% in methylene chloride).

EXAMPLE 49

8-Chloro-6-(2-fluorophenyl)-1-methyl-6H-imidazo[1,5-a][1,4]benzodiazepine

Potassium t-butoxide, 0.625 g. (5.5 mmol), was added to a solution of 1.625 g. (5 mmol) of 8-chloro-6-(2-fluorophenyl)-1-methyl-4H-imidazo[1,5-a][1,4]benzodiazepine in 20 ml. of dimethylformamide cooled to −30°. After stirring under nitrogen for 10 min. at −30° the dark mixture was acidified with 1 ml. of glacial acetic acid and was then partitioned between aqueous bicarbonate and toluene/methylene chloride (3:1 v/v). The organic layer was separated, dried and evaporated. The residue was chromatographed over 60 g. of silica gel using 25% (v/v) methylene chloride in ethyl acetate. The less polar product was eluted first and was crystallized from ethylacetate/hexane to yield product with m.p. 180°–181°.

EXAMPLE 50

8-Chloro-6-(2-fluorophenyl)-1-methyl-4H-imidazo[1,5-a][1,4]benzodiazepine

Potassium t-butoxide, 0.125 g. (1.1 mmol) ws added to a solution of 0.325 g. (1 mmol) of 8-chloro-6-(2-fluorophenyl)-1-methyl-6H-imidazo[1,5-a][1,4]benzodiazepine in 20 ml. of dimethylformamide cooled to −30°. After stirring at −30° to −20° for 15 min., the reaction mixture was acidified by addition of 0.2 ml. of glacial acetic acid and was partitioned between aqueous sodium bicarbonate and methylene chloride toluene (1:3). The organic phase was washed with water, dried and evaporated. The residue was chromatographed over 20 g. of silica gel using ethyl acetate for elution. After elution of starting material, product was collected and crystallized from ether/hexane, m.p. 156°–158°.

EXAMPLE 51

7-(2-Methyl-1,3-dioxolan-2-yl-2[bis(morpholino)phosphinyloxy]5-phenyl-3H-1,4-benzodiazepine A solution of 19.3 g. (0.06 m) of 1,3-dihydro-7-(2-methyl-1,3-dioxolan-2-yl)-5-phenyl-2H-1,4-benzodiazepin-2-one in 300 ml. of dry tetrahydrofuran was treated under an atmosphere of argon with 3.1 g. (0.075 m) of a 57% suspension of sodium hydride in mineral oil. The mixture was heated under reflux for 1 hr., cooled to room temperature when 22.2 g. (0.087 m) of dimorpholinophosphinis chloride was added. The mixture was allowed to stir at room temperature for 2 hr. and then stand overnight. Sodium chloride was removed by filtration and the crude product was obtained by removal of the solvent and crystallization of the residue from ether.

EXAMPLE 52

2,3-Dihydro-7-(2-methyl-1,3-dioxolan-2-yl)-2-nitromethylene-5-phenyl-1H-1,4-benzodiazepine A mixture of 100 ml. of dry N,N-dimethylformamide and 6.8 g. of nitromethane was treated under an atmosphere of argon with 2.8 g. (0.066 m) of a 57% suspension of sodium hydride in mineral oil. The mixture was stirred for 1 hr. at room temperature when a solution of 18 g. (0.033 m) of crude 7-(2-methyl-1,3-dioxolan-2-yl)-2[bis(morpholino)phosphinyloxy] 5-phenyl-3H-1,4-benzodiazepine in 50 ml. of dry N,N-dimethylformamide was added. The reaction mixture was allowed to stand at room temperature for 15 hrs. when the dark viscous liquid was poured over a mixture of ice and dilute acetic acid. The bright yellow precipitate was removed by filtration, dissolved in dichloromethane which was washed with dilute ammonium hydroxyide and water, dried over anhydrous sodium sulfate and evaporated. The original filtrate was extracted with dichoromethane which was washed, dried and evaporated as above. The two crude residues were combined and chromatographed over Florisil. Using dichloromethane, 10% (v/v) ether as the eluent and monitoring the fractions by tlc, several fractions containing the product were collected and evaporated. Crystallization and recrystallization from a mixture of dichloromethane and hexane gave the pure product as pale yellow prisms, m.p. 158°–161°.

EXAMPLE 53

1,3-Dihydro-7-ethyl-5-(2-fluorophenyl)-2-nitromethylene-2H-1,4-benzodiazepine

Sodium nitrite 8.6 g., (0.125 m) was added in three portions over a ½ hour period to a solution of 29.5 g. (0.1 m) of 7-ethyl-5-(2-fluorophenyl)-2-methylamino-3H-1,4-benzodiazepine in 100 ml. of glacial acetic acid. After stirring for another ½ hour at room temperaure, the mixture was diluted with ice-water and extracted with methylene chloride. The extracts were washed with water and aqueous bicarbonate, dried over sodium sulfate and evaporated to leave 21.7 g. of crude 7-ethyl-5-(2-fluorophenyl)-2-(N-nitrosomethylamino)-3H-1,4-benzodiazepine as a yellow oil.

This material was dissolved in 100 ml. of dimethylformamide and the solution was added to a mixture of 100 m. of dimethylformamide, 35 ml. of nitromethane and 9.9 g. of potassium t-butoxide which had been stirred for ½ hour at room temperature. After completed addition, the reaction mixture was stirred for 1 hour at room temperature and for 30 minutes on the steam bath. The cooled solution was acidified with glacial acetic acid, diluted with water and extracted with methylene chloride. The extracts were washed with water, dried and evaporated. The residue was dissolved in 50 ml. of ethanol and was allowed to crystallize in the refrigerator overnight after seeding. The yellow crystals were collected and recrystallized from ethanol, m.p. 138°–140°. Seed crystals were obtained by chromatography of the crude product over 40-fold amount of silica gel using 5% (v/v) of ethylacetate in methylene chloride. The analytical sample was recrystallized from ether/hexane, m.p. 138°–141°.

EXAMPLE 54

8-Ethyl-6-(2-fluorophenyl)-1-methyl-4H-imidazo [1,5-*a*] [1,4] benzodiazepine 1,3 - Dihydro - 7 - ethyl-5 - (2 - fluorophenyl) - 2 - nitromethylene-2H-1,4-benzodiazepine, 2.6 g., was hydrogenated for 4 hours with Raney nickel (1 teaspoonful) in 30 ml. of ethanol. The catalyst was separated by filtration and the filtrate was evaporated. The residue was dissolved in ether and the amine was extracted with 10% aqueous acetic acid. The extracts were washed with ether and made alkaline with ammonia. The precipitated amine was extracted with methylene chloride. The extracts were dried and evaporated to leave 1.5 g. of crude 2-aminomethyl-2,3-dihydro-7-ethyl-5-(2-fluorophenyl)-1H-1,4-benzodiazepine. This material was dissolved in 50 ml. of xylene. The solution was then heated to reflux for 2 hours after addition of 3 ml. of triethylorthoacetate. The residue obtained after evaporation under reduced pressure was chromatographed over 50 g. of silica get using 20% methanol in methylene chloride. The homogeneous fractions were combined and evaporated to yield 3a,4-dihydro-8-ethyl-6-(2-fluorophenyl)-1-methyl-3H-imidazo[1,5-a][1,4]benzodiazepine. This material was dissolved in 50 ml. of toluene and the solution was heated to reflux for 1 hour after addition of 5 g. of activated manganese dioxide. The inorganic material was separated by filtration and the filtrate was evaporated. The residue was dissolved in ether and treated with ethanolic hydrogen chloride and acetone. The crystalline dihydrochloride (m.p. 248°–255°) was collected and reconverted to the base by partitioning between methylene chloride and aqueous ammonia. The methylene chloride layer was dried and evaporated. Crystallization of the residue from ether/hexane yielded a product with m.p. 152°–154°.

EXAMPLE 55

Parenteral Formulation

| Each 1 cc ampul contains | Per cc |
|---|---|
| 8-Chloro-1-methyl-6-(2-fluorophenyl)-4H-imidazo [1,5-a][1,4]benzodiazepine maleate | 1.0 mg. |
| Benzyl Alcohol | 0.15 cc |
| Tartaric Acid Adjusted with Sodium hydroxide 100% solution | 3.0–4.0 |
| Water for Injection, U.S.P.    q.s. ad | 1 cc |

Procedure (For 10,000 cc):
1. In a clean glass or glass-lined vessel, 8,000 cc of Water for Injection were heated to 90° C. It was then cooled to 50°–60° C., and benzyl alcohol was added and dissolved with stirring. The solution was then allowed to cool to room temperature.
2. The 10.0 grams of 8-chloro-1-methyl-6-(2-fluorophenyl)-4H-imidazo [1,5-a] [1,4]benzodiazepine maleate were added under and atmosphere of nitrogen and stirred unitl completely dissolved.
3. The pH was now adjusted to 3.0±1.0, preferably 3.0±0.5 with a combination of tartaric acid buffer and sodium hydroxide solution.
4. Sufficient Water for Injection was then added to make a total volume of 10,000 cc.
5. This solution was then filtered through an 02 Selas Candle, filled into suitable size ampuls, gassed with nitrogen and sealed.

EXAMPLE 56

Tablet Formulation

|  | Per Tablet |
|---|---|
| 8-Chloro-1-methyl-6(2-fluorophenyl)-4H-imidazo[1,5-a][1,4]-benzodiazepine maleate | 10.0 mg. |
| Lactose | 113.5 mg. |
| Corn Starch | 70.5 mg. |
| Pregelatinized Corn Starch | 8.0 mg. |
| Calcium Stearate | 3.0 mg. |
| Total Weight | 205.0 mg. |

Procedure:
1. 8-Chloro-1-methyl-6(2-fluorophenyl)-4H-imidazo[1,5-a][1,4]benzodiazepine maleate was mixed with the lactose, corn starch and pregalatinized corn starch in a suitable size mixer.
2. The mix was passed through a Fitzpatrick Comminuting machine fitted with #1A screen and with knives forward.
3. The mix was returned to the mixer and moistened with water to a thick paste. The moist mass was passed through a #12 screen and the moist granules were dried on paper lined trays at 110° F.

4. The dried granules were returned to the mixer, calcium stearate was added and mixed well.
5. The granules were compressed at a tablet weight of 200 mg. using standard concave punches having a diameter of 5/16".

EXAMPLE 57

Tablet Formulation

|  | Per Tablet |
| --- | --- |
| 8-Chloro-1-methyl-6-(2-fluorophenyl)-4H-imidazo[1,5-a][1,4]benzodiazepine maleate | 25.00 mg. |
| Lactose, U.S.P. | 64.50 mg. |
| Corn Starch | 10.00 mg. |
| Magnesium Stearate | 0.50 mg. |

Procedure:
1. 8-Chloro-1-methyl-6-(2-fluorophenyl)-4H-imidazo[1,5-a][1,4]benzodiazepine maleate was mixed with the lactose, corn starch and magnesium stearate in a suitable mixer.
2. The mixture was further blended by passing through a Fitzpatrick Comminuting Machine fitted with a #1A screen with knives forward.
3. The mixed powders were slugged on a tablet compressing machine.
4. The slugs were comminuted to a suitable mesh size (#16 screen) and mixed well.
5. The tablets were compressed at a tablet weight of 100 mg. using tablet punches having a diameter of approximately ¼". (Tablets may be either flat or biconvex and may be scored if desired.)

EXAMPLE 58

Capsule Formulation

|  | Per Capsule |
| --- | --- |
| 8-Chloro-1-methyl-6-(2-fluorophenyl)-4H-imidazo[1,5-a][1,4]benzodiazepine maleate | 25 mg. |
| Lactose | 158 mg. |
| Corn Starch | 37 mg. |
| Talc | 5 mg. |
| Total Weight | 225 mg. |

Procedure:
1. 8-Chloro-1-methyl-6-(2-fluorophenyl)-4H-imidazo[1,5-a][1,4]benzodiazepine maleate was mixed with the lactose and corn starch in a suitable mixer.
2. The mixture was further blended by passing through a Fitzpatrick Comminuting Machine with a #1A screen with knives forward.
3. The blended powder was returned to the mixer, the talc added and blended thoroughly. The mixture was then filled into #4 hard shell gelatin capsules on a Parke Davis capsulating machine. (Any similar type machine may be used.)

EXAMPLE 59

Capsule Formulation

|  | Per Capsule |
| --- | --- |
| 8-Chloro-1-methyl-6-(2-fluorophenyl)-4H-imidazo[1,5-a][1,4]benzodiazepine maleate | 50 mg. |
| Lactose, U.S.P. | 125 mg. |
| Corn Starch, U.S.P. | 30 mg. |
| Talc, U.S.P. | 5 mg. |
| Total Weight | 210 mg. |

Procedure:
1. 8-Chloro-1-methyl-6-(2-fluorophenyl)-4H-imidazo[1,5-a][1,4]benzodiazepine maleate was mixed with lactose and corn starch in a suitable mixer.
2. The mixture was further blended by passing through a Fitzpatrick Comminuting Machine with a #1A screen with knives forward.
3. The blended powder was returned to the mixer, the talc added and blended thoroughly.
4. The mixture was filled into #4 hard shell gelatin capsules on a Park Davis capsulating machine.

EXAMPLE 60

Capsule Formulation

|  | Per Capsule |
| --- | --- |
| 8-Chloro-1,4-dimethyl-6-(2-fluorophenyl)-4H-imidazo[1,5-a][1,4]benzodiazepine maleate | 50 mg. |
| Lactose, U.S.P. | 125 mg. |
| Corn Starch, U.S.P. | 30 mg. |
| Talc, U.S.P. | 5 mg. |
| Total Weight | 210 mg. |

Procedure:
1. 8-Chloro-1,4-dimethyl-6-(2-fluorophenyl)-4H-imidazo[1,5-a][1,4]benzodiazepine maleate was mixed with lactose and corn starch in a suitable mixer.
2. The mixture was further blended by passing through a Fitzpatrick Comminuting Machine with a #1A screen with knives forward.
3. The blended powder was returned to the mixer, the talc added and blended thoroughly.
4. The mixture was filled into #4 hard shell gelatin capsules on a Parke Davis capsulating machine.

EXAMPLE 61

Capsule Formulation

|  | Per Capsule |
| --- | --- |
| 8-Chloro-1,4-dimethyl-6-(2-fluorophenyl)-4H-imidazo[1,5-a][1,4]benzodiazepine maleate | 25 mg. |
| Lactose | 258 mg. |
| Corn Starch | 37 mg. |
| Talc | 5 mg. |
| Total Weight | 225 mg. |

Procedure:
1. 8Chlor-1,4-dimethyl-6-(2-fluorophenyl)-4H-imidazo[1,5-a][1,4] benzodiazepine maleate was mixed with the lactose and corn starch in a suitable mixer.
2. The mixture was further blended by passing through a Fitzpatrick Comminuting Machine with a #1A screen with knives forward.
3. The blended powder was returned to the mixer, the talc added and blended thoroughly. The mixture was then filled into #4 hard shell gelatin capsules on a Park Davis capsulating machine. (Any similar type machine may be used.)

EXAMPLE 62

Tablet Formulation

|  | Per Tablet |
| --- | --- |
| 8-Chloro-1,4-dimethyl-6-(2-fluorophenyl)-4H-imidazo[1,5-a][1,4]benzodiazepine maleate | 25.00 mg. |
| Lactose, U.S.P. | 64.50 mg. |
| Corn Starch | 10.00 mg. |
| Magnesium Stearate | 0.50 mg. |

Procedure:
1. 8-Chloro-1,4-dimethyl-6-(2-fluorophenyl)-4H-imidazo[1,5-a][1,4]benzodiazepine maleate was mixed with the lactose, corn starch and magnesium stearate in a suitable mixer.
2. The mixture was further blended by passing through a Fitzpatrick Comminuting Machine fitted with a #1A screen with knives forward.
3. The mixed powders were slugged on a tablet compressing machine.
4. The slugs were comminuted to a suitable mesh size (#26 screen) and mixed well.
5. The tablets were compressed at a tablet weight of 100 mg. using tablet punches having a diameter of approximately ¼". (Tablets may be either flat or biconvex and may be scored if desired.)

EXAMPLE 63

Tablet Formulation

|  | Per Tablet |
| --- | --- |
| 8-Chloro-1,4-dimethyl-6(2-fluorophenyl)-4H-imidazo[1,5-a][1,4]benzodiazepine maleate | 10.0 mg. |
| Lactose | 113.5 mg. |
| Corn Starch | 70.5 mg. |
| Pregelatinized Corn Starch | 8.0 mg. |
| Calcium Stearate | 3.0 mg. |
| Total Weight | 205.0 mg. |

Procedure:
1. 8-Chloro-1,4-dimethyl-6-(2-fluorophenyl)-4H-imidazo[1,5-a][1,4]benzodiazepine mealeate was mixed with the lactose, corn starch and pregelatinized corn starch in a suitable size mixer.
2. The mix was passed through a Fitzpatrick Comminuting machine fitted with #1A screen and with knives forward.
3. The mix was returned to the mixer and moistened with water to a thick paste. The moist mass was passed through a #12 screen and moist granules were dried on paper lined trays at 110° F.
4. The dried granules were returned to the mixer, the calcium stearate was added and mixed well.
5. The granules were compressed at a tablet weight of 200 mg. using standard concave punches having a diameter of 5/16".

EXAMPLE 64

Parenteral Formulation

| Each 1 cc ampul contains: | Per cc |
| --- | --- |
| 8-Chloro-1,4-dimethyl-6-(2-fluorophenyl)-4H-imidazo[1,5-a][1,4]benzodiazepine maleate | 1.0 mg. |
| Benzyl Alcohol | 0.15 cc. |
| Tartaric Acid adjusted with Sodium Hydroxide 100% solution | 3.0–4.0 |
| Water for Injection, U.S.P.     q.s. ad | 1 cc. |

Procedure (For 10,000 cc):
1. In a clean glass or glass-lined vessel, 8,000 cc of Water for Injection were heated to 90° C. It was then cooled to 50°–60° C., and benzyl alcohol was added and dissolved with stirring. The solution was then allowed to cool to room temperature.
2. The 10.0 grams of 8-Chloro-1,4-dimethyl-6-(2-fluorophenyl)-4H-imidazo[1,5-a][1,4]benzodiazepine maleate were added under an atmosphere of nitrogen and stirred until completely dissolved.
3. The pH was now adjusted to 3.0±1.0, preferably 3.0±0.5 with a combination of tartaric acid buffer and sodium hydroxide solution.
4. Sufficient WATER FOR Injection was then added to make a total volume of 10,000 cc.
5. This solution was then filtered through an 02 Sedas candle, filled into suitable size ampuls, gassed with nitrogen and sealed.

EXAMPLE 65

1-Acetyl-2-acetylaminomethyl-7-chloro-2,3-dihydro-5-(2-fluorophenyl)-1H-1,4-benzodiazepine 2-Aminomethyl-7-chloro-2,3-dihydro-5-(2-fluorophenyl)-1H-1,4-benzodiazepine dimaleate, 8.0 g (0.015 m) was partitioned between methylene chloride and aqueous ammonia. The methylene chloride solution was washed with water, dried over sodium sulfate and evaporated. The residue was dissolved in 50 ml of pyridine. After addition of 10 ml of acetic anhydride the mixture was heated on the steam bath for 4 hours. The reagents were evaporated under reduced pressure and the residue was partitioned between methylene chloride and aqueous sodium bicarbonate solution. The organic layer was dried and evaporated. Crystallization of the residue from methylene chloride/ether with seeding yielded a final product with mp. 213°–215°. Seeds were obtaned by chromatography over silica gel (40 fold amount) using 10% (v/v) ethanol in methylene chloride for elu-

EXAMPLE 66

8-Chloro-3a,4-dihydro-6-(2-fluorophenyl)-1-methyl-3H-imidazo[1,5-a][1,4]benzodiazepine A mixture of 0.5 g of 1-acetyl-2-acetylaminomethyl-7-chlor-2,3-dihydro-5-(2-fluorophenyl)-1H-1,4-benzodiazepine and 10 g of polyphosphoric acid was heated to 150°–170° for 10 min. The cool reaction mixture was dissolved in ice-water and the solution was made alkaline with ammonia. The precipitated base was extracted with methylene chloride. The extracts were washed with water, dried over sodium sulfate and evaporated. The residue was chromatographed over 10 g of silica gel using 20% methanol in methylene chloride. The clean fractions were combined and evaporated. The residue was crystallized from ether to yield a final product with mp. 142°–144°.

EXAMPLE 67

8-Chloro-1,4-dimethyl-6-(2-fluorophenyl)-4H-imidazo[1,5-a]benzodiazepine maleate 41.3 g. of 8-chloro-1,4-dimethyl-6-(2-fluorophenyl)-4H-imidazo[1,5-a][1,4]benzodiazepine dihydrochloride was partitioned between methylene chloride and aqueous ammonia. The methylene chloride solution was washed with water, dried over sodium sulfate and evaporated to leave 34 g. of free base. This material was dissolved in 50 ml of 2-propanol and the solution was treated with a solution of 12 g. of maleic acid in 40 ml of 2-propanol. The solution was gradually diluted with 300 ml of ether. The precipitated crystals were collected and dried to leave the maleate salt with m.p. 130°–132° after recrystallization from ethanol/ether.

EXAMPLE 68

7-Chloro-1,3-dihydro-2-(dimethoxymalonylidene)-5-phenyl-2H-1,4-benzodiazepine*

A mixture of 40.8 g. (0.1 m) of 7-chloro-1,3-dihydro-2-(dimethoxymalonylidene)-5-phenyl-2H-1,4-benzodiazepine 4-oxide, 250 ml. of methanol, 250 ml. of tetrahydrofuran and 1 tablespoonful of Raney nickel was hydrogenated at atmospheric pressure for 5 hours. The catalyst was removed by filtration and the filtrate was evaporated. Crystallization of the residue from methylene chloride/2-propanol yielded colorless crystals with m.p. 160°–163°. For analysis it was recrystallized from 2-propanol, m.p. 165°–166°.
*J. Org. Chem. 40, 153 (1975)

A second modification of crystals with m.p. 138°–140° was obtained in some instances.

EXAMPLE 69

7-Chloro-1,3-dihydro-2-(dimethoxymalonylidene)-5-phenyl-2H-1,4-benzodiazepine*

Phosphorus trichloride, 4 ml., was Added to a solution of 4 g. (0.01 m) of 7-chloro-1,3-dihydro-2-(2-dimethoxymalonylidene)-5-phenyl-2H-1,4-benzodiazepine 4-oxide in 100 ml. of methylene chloride. After sitting at room temperature overnight, the solution was washed with 10% aqueous sodium carbonate solution. The methylene chloride layer was dried and evaporated. Crystallization of the residue from 2-propanol and recrystallization from methylene chloride/2-propanol yielded product with m.p. 165°–166°.
*J. Org. Chem. 40, 153 (1975)

EXAMPLE 70

7-Chloro-1,3-dihydro-2-(dimethoxymalonylidene)-5-(2-fluorophenyl-2H-1,4-benzodiazepine Sodium nitrite 27.6 g. (0.4 m) was added in portions over a period of 30 minutes to a solution of 90.45 g. (0.3 m) of 7-chloro-5-(2-fluorophenyl)-2-methylamino-3H-1,4-benzodiazepine in 400 ml. of glacial acetic acid. Following completed addition, the mixture was stirred at room temperature for 1 hour and was diluted with 1 l. of water and extracted with methylene chloride. The extracts were washed twice with water and then with 10% aqueous sodium carbonate solution. The solution was drid and evaporated to yield crude 7-chloro-5-(2-fluorophenyl)-2-(N-nitrosomethylamino)-3H-1,4-benzodiazepine as a yellow oil.

This material was dissolved in 300 ml. of dimethylformamide and was added to a mixture of 150 ml. of dimethyl malonate, 40.4 g. of potassium t-butoxide and 500 ml. of dimethylformamide which had been stirred at room temperature for 10 minutes. The reaction mixture was stirred under nitrogen overnight at room temperature, was acidified by addition of 50 ml. of glacial acetic acid, diluted with water and extracted with methylene chloride. The extracts were washed with water and aqueous sodium carbonate solution, were dried over sodium sulfate and evaporated. Crystallization of the residue from ethanol yielded colorless crystals with m.p. 170°–172°. For analysis the product was recrystallized from methylene chloride/ethanol, m.p. unchanged.

EXAMPLE 71

7-Chloro-1,3-dihydro-2-(dimethoxymalonylidene)-5-phenyl-2H-1,4-benzodiazepine 4-oxide*

Potassium t-butoxide, 26 g. (0.232 m) was added to a mixture of 300 ml. of dimethylformamide and 50 ml. (0.44 m) of dimethyl malonate. After stirring under nitrogen for 10 minutes a solution of 66 g. )0.209 m) of 7-chloro-2-(N-nitrosomethylamino)-5-phenyl-3H-1,4-benzodiazepine 4-oxide in 100 ml. of dimethyl formamide was added over a 10 minute period. The mixture was then slowly heated on the steam bath and kept for 10 minutes at 65°. After cooling to room temperature 40 ml. of glacial acetic acid was added followed by 1 l. of water over a period of 30 minutes with occasional scratching. The precipitated crystals were collected, washed with water and dissolved in methylene chloride. The solution was dried over sodium sulfate and concentrated to a small volume. The product was crystallized by addition of hexane to yield product with m.p. 188°–190°. The analytical sample was recrystallized from methylene chloride/hexane, m.p. 194°–195°.
*J. Org. Chem. 40, 153 (1975)

EXAMPLE 72

7-Chloro-1,3-dihydro-2-(methoxycarbonylmethylene)-5-phenyl-2H-1,4-benzodiazepine A mixture of 115 g. (0.3 m) of 7-chloro-1,3-dihydro-2-(dimethoxymalonylidene)-5-phenyl-2H-1,4-benzodiazepine, 1.5 l. of methanol and 14.4 g. (0.36 m) of sodium hydroxide was heated to reflux for 5 hours under an atmosphere of nitrogen. The cool reaction mixture was gradually diluted with 2.5 l. of water with ice cooling. The precipitated crystals were collected, washed with water and dried in vacuum at 60° to yield an off-white tion. The analytical sample was recrystallized from ethylacetate/hexane and had mp. 215°–217°.

product with m.p. 167°–170°. The analytical sample was recrystallized from ether, m.p. 171°–173°.

EXAMPLE 73

7-Chloro-1,3-dihydro-5-(2-fluorophenyl)-2-(methoxycarbonylmethylene)-2H-1,4-benzodiazepine A mixture of 20 g. (0.05 m) of 7-chloro-1,3-dihydro-2-(dimethoxymalonylidene)-5-(2-fluorophenyl)-2H-1,4:benzodiazepine, 400 ml. of methanol and 3.3 g. (0.059 m) of potassium hydroxide was heated to reflux under nitrogen for 5 hours. After evaporation of the bulk of the solvent, the residue was gradually diluted with water and the precipitated crystals were collected, washed with water and dried to leave product with m.p. 158°–160°.

For analysis it was recrystallized from methylene chloride/hexane, m.p. 161–162°.

EXAMPLE 74

7-Chloro-1,3-dihydro-2-(methoxycarbonylmethylene)-5-phenyl-2H-1,4-benzodiazepine 4-oxide A mixture of 31 g. (0.075 m) of 7-chloro-1,3-dihydro-2-(dimethoxymalonylidene)-5-phenyl-2H-1,4-benzodiazepine 4-oxide, 4 g. (0.095 m) of sodium hydroxide, 300 ml. of methanol and 5 ml. of water was heated to reflux for 3 hours. After cooling, the mixture was diluted with water. The precipitated crystals are collected and recrystallized from methanol to yield product with m.p. 215–216°.

EXAMPLE 75

7-Chloro-alpha-hydroxyimino-5-phenyl-3H-1,4-benzodiazepine-2-acetic acid, methyl ester Sodium nitrite, 2.8 g. (0.04 m) was added to a solution of 8 g. (0.025 m) of 7-chloro-1,3-dihydro-2-(methoxycarbonylmethylene)-5-phenyl-2H-1,4-benzodiazepine in 100 ml. of glacial acetic acid. The mixture was stirred under nitrogen for 10 minutes. The product started to crystallize out after a few minutes. After dilution with 100 ml. of water, the precipitated product was collected, washed with water, dried and recrystallized from tetrahydrofuran/methanol to yield yellow crystals with m.p. 235–237° dec.

EXAMPLE 76

7-Chloro-5-(2-fluorophenyl)-alpha-hydroxyimino-3H-1,4-benzodiazepine-2-acetic acid, methyl ester Sodium nitrite, 8.8 g. (0.125 m), was added to a solution of 28 g. (0.08 m) of 7-chloro-1,3-dihydro-5-(2-fluorophenyl)-2-(methoxycarbonylmethylene)-2H-1,4-benzodiazepine in 250 ml. glacial acetic acid. The mixture was stirred at room temperature for 10 minutes and then diluted with 250 ml. of water. The crystalline product was filtered off, washed with water, methanol and ether and dried to leave yellow crystals with m.p. 238°–241°. dec.

EXAMPLE 77

7-Chloro-alpha-hydroxyimino-5-phenyl-3H-1,4-benzodiazepine-2-acetic acid, methyl ester 4-oxide Sodium nitrite, 1.4 g. (0.02 m), was added to a solution of 6.8 g. (0.02 m) of 7-chloro-1,3-dihydro-2-(methoxycarbonylmethylene)-5-phenyl-2H-1,4-benzodiazepine 4-oxide in 100 ml. of glacial acetic acid. After stirring for 15 minutes at room temperature the reaction mixture was diluted with 100 ml. of water. The crystals were collected, washed with water and dried to leave a yellow product with m.p. 237°–239° dec. The analytical sample was recrystallized from dimethylformamide/methanol and had the same m.p.

EXAMPLE 78

Methyl 8-chloro-1-methyl-6-phenyl-4H-imidazo[1,5-a]benzodiazepine 3-carboxylate

7-Chloro-alpha-hydroxyimino-5-phenyl-3H-1,4-benzodiazepine-2-acetic acid, methyl ester, 3.6 g. (0.01 m), was dissolved in a mixture of 200 ml. of tetrahydrofuran and 100 ml. of methanol by warming. Raney nickel (1 teaspoonful) was added and the mixture was hydrogenated at atmospheric pressure until hydrogen uptake flattened (1 hour and 10 minutes). The catalyst was removed by filtration and the filtrate was evaporated at the end azeotropically with toluene. The residue was dissolved in 20 ml. of methanol. Following the addition of 3 ml. of triethyl ortho-acetate and 0.3 ml. ethanolic hydrogen chloride (5%), the solution was heated to reflux for 5 minutes. The residue left after evaporation was partitioned between methylene chloride and saturated aqueous sodium bicarbonate solution. The organic phase was separated, dried and evaporated. Crystallization of the residue from ether yielded a product, which after recrystallization from methylene chloride/ether/hexane had m.p. 254°–256°.

EXAMPLE 79

Methyl 8-chloro-6-(2-fluorophenyl)-1-methyl-4H-imidazo[1,5-a][1,4]benzodiazepine-3-carboxylate 7-Chloro-5-(2-fluorophenyl)-alpha-hydroxyimino-3H-1,4-benzodiazepine-2-acetic acid methyl ester, 11.25 g. (0.03 m) was hydrogenated as described in the previous example with Raney nickel in a mixture of 750 ml. of tetrahydrofuran and 500 ml. of methanol. The nickel was filtered off and the filtrate was evaporated. The residue was dissolved in 100 ml. of methanol and 11 ml. of triethyl orthoacetate and 5 ml. of ethanolic hydrogen chloride (5%) was added. The mixture was heated to reflux for 10 minutes, was evaporated and the residue was partitioned between methylene chloride and aqueous sodium bicarbonate solution. The methylene chloride solution was dried and evaporated and the residue was chromatographed over 300 g. of silica gel using methylene chloride/ethyl acetate 1:3 (v/v). The clean fractions were combined and evaporated and crystallized from ether to yield a product with m.p. 162°–164°. The analytical sample was recrystallized from ethyl acetate/hexane.

EXAMPLE 80

Methyl 8-chloro-6-(2-fluorophenyl)-4H-imidazo[1,5-a][1,4]benzodiazepine 3-carboxylate 7-Chloro-5-(2-fluorophenyl)-alpha-hydroxyimino-3H-1,4-benzodiazepine-2-acetic acid, methyl ester, 11.25 g. (0.03 m), was dissolved in a mixture of 750 ml. of tetrahydrofuran and 500 ml. of methanol by warming. Raney nickel, 20 g., was added and the mixture was hydrogenated at atmospheric pressure for 4 hours. The catalyst was removed by filtration and the filtrate was evaporated at the end azeotropically with toluene. The residue was dissolved in 100 ml. of methanol. After addition of 10 ml. of triethyl orthoformate and 5 ml. of ethanolic hydrogen chloride (5%), the mixture was heated to reflux for 10 minutes. It was then evaporated and the residue was partitioned between methylene chloride and saturated aqueous sodium bicarbonate solution. The methylene chloride layer was separated, dried and evaporated and the residue was crystallized from ether to yield a product which was recrystallized from methylene chloride/ether/hexane, m.p. 179°–181°.

EXAMPLE 81

8-Chloro-1-methyl-6-phenyl-4H-imidazo[1,5-a][1,4]benzodiazepine 3-carboxylic acid A mixture of 7.3 g. (0.2 m) of methyl 8-chloro-1-methyl-6-phenyl-4H-imidazo[1,5-a][1,4]benzodiazepine 3-carboxylate, 2.24 g. (0.04 m) of potassium hydroxide, 200 ml. of methanol and 6 ml. of water was heated to reflux for 4 hours. The methanol was partially removed under reduced pressure and the residue was acidified with glacial acetic acid and crystallized by addition of water. The crystals were collected, washed with water and dried to yield an off-white product. For analysis it was recrystallized from ethyl acetate, m.p. 270°–273° dec.

EXAMPLE 82

8-Chloro-6-(2-fluorophenyl)-1-methyl-4H-imidazo[1,5-a][1,4]benzodiazepine 3-carboxylic acid A mixture of 7.7 g. (0.02 m) of methyl 8-chloro-6-(2-fluorophenyl)-1-methyl-4H-imidazo[1,5-a][1,4]benzodiazepine 3-carboxylate, 2.24 g. (0.04 m) of potassium hydroxide, 200 ml. of methanol and 6 ml. of water was heated to reflux for 3½ hours. The solvent was partially evaporated and the residue was acidified with glacial acetic acid and diluted with water while hot. The precipitated crystals were collected after cooling in ice/water and were dried to yield the final product. For analysis it was recrystallized from methylene chloride/methanol/ethyl acetate, m.p. 271°–274° dec.

EXAMPLE 83

Potassium 8-chloro-6-(2-fluorophenyl)-1-methyl-4H-imidazo[1,5-a][1,4]benzodiazepine 3-carboxylate hydrate A suspension of 1.85 g. (5 mmol) of 8-chloro-6-(2-fluorophenyl)-1-methyl-4H-imidazo[1,5-a][1,4]benzodiazepine 3-carboxylic acid in 25 ml. of 2-propanol was heated on the steam bath and treated with 2.2 ml. 5N potassium hydroxide solution. After complete solution, the potassium salt was crystallized by cooling in ice/water. It was collected, washed with 2-propanol and ether and dried in high vacuum at 90° to yield colorless crystals with m.p. 245°–255°.

EXAMPLE 84

8-Chloro-6-(2-fluorophenyl)-4H-imidazo[1,5-a][1,4]benzodiazepine 3-carboxylic acid A mixture of 1.48 g. (0.004 m) of methyl 8-chloro-6-(2-fluorophenyl)-4H-imidazo[1,5-a][1,4]benzodiazepine 3-carboxylate, 0.5 g. (0.009 m) of potassium hydroxide, 50 ml. of methanol and 2 ml. of water was heated to reflux for 3 hours under an atmosphere of nitrogen. The methanol was partially evaporated and the residue was acidified with glacial acetic acid and diluted with water while the solution was still hot. The crystals were collected after cooling in ice/water and were dried in vacuum to yield a product with m.p. 245°–247° dec.

EXAMPLE 85

8-Chloro-3-hydroxymethyl-1-methyl-6-phenyl-4H-imidazo[1,5-a][1,4]benzodiazepine

A solution of 0.73 g. (2 mmol) of methyl 8-chloro-1-methyl-6-phenyl-4H-imidazo[1,5-a][1,4]benzodiazepine 3-carboxylate in 50 ml. of tetrahydrofuran was added to a suspension of 0.3 g. (7.5 mmol) of lithium aluminum hydride in 20 ml. of tetrahydrofuran cooled to −10°.

Following addition the mixture was stirred for 30 minutes without cooling and was hydrolyzed by addition of 2 ml. of water. The inorganic material was filtered off and the filtrate was dried and evaporated. Crystallization of the residue from methylene chloride/ether/hexane yielded colorless crystals with m.p. 252–255°.

EXAMPLE 86

8-Chloro-6-(2-fluorophenyl)-3-hydroxymethyl-1-methyl-4H-imidazo[1,5-a][1,4]benzodiazepine A solution of 7.7 g. (0.02 m) of methyl 8-chloro-6-(2-fluorophenyl)-1-methyl-4H-imidazo[1,5-a][1,4]benzodiazepine 3-carboxylate in 100 ml. of tetrahydrofuran was added at 0°–5° to a suspension of 2 g. (0.05 m) of lithium aluminum hydride in 100 ml. of ether. After addition the mixture was stirred for 15 minutes without cooling and then hydrolyzed by addition of 15 ml. of water. The inorganic material was separated by filtration and washed with methylene chloride. The filtrate was dried and evaporated. Crystallization of the residue from methylene chloride/ether/hexane yielded a product which was recrystallized from ethyl acetate/methanol for analysis, m.p. 233°–235°.

EXAMPLE 87

8-Chloro-6-(2-fluorophenyl)-4H-imidazo[1,5-a][1,4]benzodiazepine and 8-chloro-6-(2-fluorophenyl)-6H-imidazo[1,5-a][1,4]benzodiazepine A suspension of 1.5 g. of 8-chloro-6-(2-fluorophenyl)-4H-imidazo[1,5-a][1,4]benzodiazepine 3-carboxylic acid in 10 ml. of mineral oil was heated up to 230° for 5 minutes. The reaction mixture was partitioned between 1N hydrochloric acid and ether. The aqueous phase was made alkaline with ammonia and was extracted with methylene chloride. The extracts were dried and evaporated and the residue was chromatographed over 60 g. of silica gel using 25% (v/v) methylene chloride in ethyl acetate. The less polar 6H-imidazo[1,5-a][1,4]benzodiazepine was crystallized from ethyl acetate to yield colorless crystals with m.p. 195°–196°.

The more polar component was crystallized from ether to yield 4H-imidazo [1,5-a][1,4]benzodiazepine with m.p. 150°–151°.

EXAMPLE 88

8-Chloro-1-methyl-6-phenyl-4H-imidazo[1,5-a][1,4]benzodiazepine 3-carboxaldehyde A mixture of 3 g. of 8-chloro-3-hydroxymethyl-1-methyl-6-phenyl-4H-imidazo[1,5-a][1,4]benzodiazepine, 300 ml. of methylene chloride and 15 g. of activated manganese dioxide was stirred at room temperature for 1 hours. The manganese dioxide was filtered off and washed with methylene chloride. The filtrate was evaporated and the residue was crystallized from methylene chloride/ether/hexane to yield a product with m.p. 218°–220°.

EXAMPLE 89

8-Chloro-6-(2-fluorophenyl)-1-methyl-4H-imidazo[1,5-a][1,4]benzodiazepine 3-carboxaldehyde A mixture of 4 g. of 8-chloro-6-(2-fluorophenyl)-3-hydroxymethyl-1-methyl-4H-imidazo[1,5-a][1,4]benzodiazepine, 200 ml. of methylene chloride and 20 g. of activated manganese dioxide was stirred at room temperature for 1 hour. The MnO$_2$ was removed by filtration and washed well with methylene chloride. The filtrate was evaporated and the residue was crystallized from methylene chloride/ether/hexane to yield a product with m.p. 190°–192° after recrystallization from methylene chloride/ethyl acetate/hexane.

EXAMPLE 90

3-Acetoxymethyl-8-chloro-6-(2-fluorophenyl)-1-methyl-4H-imidazo[1,5-a][1,4]benzodiazepine A solution of 0.71 g. (2 mmol) of 8-chloro-6-(2-fluorophenyl)-3-hydroxymethyl-1-methyl-4H-imidazo[1,5-a][1,4]benzodiazepine in 20 ml. of pyridine was treated with 2 ml. of acetic anhydride. After standing at room temperature overnight, the solvent was evaporated under reduced pressure and the residue was partitioned between methylene chloride and sodium bicarbonate solution. The organic phase was dried and evaporated. The residue did not crystallize and was purified by chromatography over 30 g. of silica gel using methylene chloride/ethyl acetate 1:3. The homogeneous fractions were combined and evaporated. The residue did not crystallize and was characterized spectroscopically.

EXAMPLE 91

8-Chloro-1-methyl-6-phenyl-4H-imidazo[1,5-a][1,4]benzodiazepine 3-carboxamide

Methyl 8-chloro-1-methyl-6-phenyl-4H-imidazo[1,5-a][1,4]benzodiazepine 3-carboxylate, 0.74 g. (2 mmol), was heated in 30 ml. methanolic ammonia at 120° for 18 hours in a sealed vessel. The solvent was evaporated and the residue was recrystallized from methylene chloride/ethanol to yield colorless crystals with m.p. 335°–340°.

EXAMPLE 92

8-Chloro-1,N-dimethyl-6-phenyl-4H-imidazo[1,5-a][1,4]benzodiazepine 3-carboxamide A mixture of 0.74 g. (2 mmol) of methyl 8-chloro-1-methyl-6-phenyl-4H-imidazo[1,5-a][1,4]benzodiazepine 3-carboxylate and 20 ml. of ethanol containing 25% of methylamine was heated at 120° for 18 hours in a sealed vessel. The solvent was evaporated and the residue was crystallized from methylene chloride/ethanol to yield a product with m.p. 260°–263°. The analytical sample was recrystallized from tetrahydrofuran/ethanol.

EXAMPLE 93

Methyl 8-chloro-5,6-dihydro-1-methyl-6-phenyl-4H-imidazo[1,5-a][1,4]benzodiazepine 3-carboxylate Zinc dust, 2 g., was added to a solution of 1.83 g. (5 mmol) of methyl 8-chloro-1-methyl-6-phenyl-4H-imidazo[1,5-a][1,4]benzodiazepine 3-carboxylate in 50 ml. of methylene chloride and 10 ml. of glacial acetic acid. The mixture was stirred for 2 hours at room temperature. The inorganic material was filtered off and the filtrate was washed with dilute aqueous ammonia. The methylene chloride solution was dried and evaporated. Crystallization of the residue from methylene chloride/ethyl acetate/ether yielded colorless crystals with m.p. 233°–235°. The analytical sample was recrystallized from ethyl acetate/methylene chloride/methanol, m.p. 234°–236°.

EXAMPLE 94

8-Chloro-6-(2-fluorophenyl)-1-methyl-4H-imidazo[1,5-a][1,4]benzodiazepine 3-carboxylic acid hydrazide A mixture of 7.7 g. of methyl 8-chloro-6-(2-fluorophenyl)-1-methyl-4H-imidazo[1,5-a][1,4]benzodiazepine 3-carboxylate, 100 ml. of isobutanol and 20 ml. of hydrazine was heated to reflux for 1 hour. The crude product obtained after evaporation was chromatographed over 250 g. of silica gel using 5% ethanol in methylene chloride. The clean fractions were combined and evaporated. Crystallization of the residue from methylene chloride/ether yielded colorless crystals with m.p. 235°–237°.

EXAMPLE 95

8-Chloro-5,6-dihydro-1-methyl-6-phenyl-4H-imidazo[1,5-a][1,4]benzodiazepine 3-carboxylic acid hydrazide A mixture of 7.4 g. of methyl 8-chloro-5,6-dihydro-1-methyl-6-phenyl-4H-imidazo[1,5-a][1,4]benzodiazepine 3-carboxylate, 20 ml. of hydrazine and 200 ml. of isobutanol was heated to reflux for 3 hours. After evaporation under reduced pressure, the residue was crystallized from ethanol/ether to yield a product with m.p. 225°–230°. The analytical sample was recrystallized from ethyl acetate/methanol, m.p. 228°–230°.

EXAMPLE 96

Methyl 8-chloro-1,4-dimethyl-6-phenyl-4H-imidazo[1,5-a][1,4]benzodiazepine 3-carboxylate A solution of 0.73 g. (2 mmol) of methyl 8-chloro-1-methyl-6-phenyl-4H-imidazo[1,5-a][1,4]benzodiazepine 3-carboxylate in 20 ml. of dry dimethylformamide was cooled to −30° with stirring under nitrogen. Potassium t-butoxide, 0.25 g. (2.2 mmol) was added and after stirring for 5 minutes 0.3 g. (2.1 mmol) of methyliodide was added. The mixture was allowed to reach room temperature within 1 hour and was then partitioned between saturated aqueous bicarbonate and methylene chloride. The methylene chloride layer was washed with water, dried and evaporated. Crystallization of the residue from ether yielded colorless crystals with m.p. 217°–221°. The analytical sample was recrystallized from ethyl acetate/hexane, m.p. 220°–222°.

EXAMPLE 97

Methyl 8-chloro-6-(2-fluorophenyl)-4-methyl-4H-imidazo[1,5-a][1,4]benzodiazepine 3-carboxylate Potassium t-butoxide, 0.25 g. (2.2 mmol), was added to a solution of 0.74 g. (2 mmol) of methyl 8-chloro-6-(2-fluorophenyl)-4H-imidazo[1,5-a][1,4]benzodiazepine 3-carboxylate in 20 ml. of dimethylformamide cooled to −30°. After stirring for 5 minutes under nitrogen 0.32 g.

(2.26 mmol) of methyliodide was added and the reaction mixture was allowed to warm to room temperature within 30 minutes. It was then partitioned between aqueous bicarbonate and methylene chloride. The organic layer was washed with water, dried and evaporated. The residue was crystallized from ether to yield a product, which after recrystallization from ethyl acetate/hexane, had m.p. 190°–191°.

EXAMPLE 98

8-chloro-1-methyl-6-phenyl-4H-imidazo[1,5-a][1,4]benzodiazepine-3-carboxaldoxime 8Chloro-1-methyl-6-phenyl-4H-imidazo[1,5-a][1,4]benzodiazepine-3-carboxaldehyde, 3.4 g. (0.01 m), was partially dissolved by heating in 200 ml. of ethanol. Hydroxyamine hydrochloride, 1.05 g. (0.015 m) and 4 ml. of triethylamine was added and the mixture was heated on the streambath until solution was complete. The solvent was partially evaporated and the product was crystallized by dilution with water. The crystals were collected, washed with ethanol and ether and dried to yield final product with m.p. 280°–282° C. dec. The analytical sample was recrystallized from ethanol/tetrahydrofuran.

EXAMPLE 99

3-Aminomethyl-8-chloro-1-methyl-6-phenyl-4H-imidazo[1,5-a][1,4]benzodiazepine

8-Chloro-1-methyl-6-phenyl-4H-imidazo[1,5-a][1,4]benzodiazepine-3-carboxaldoxime, 2.1 g., was dissolved by warming in 100 ml. of ethanol and 100 ml. of tetrahydrofuran. The solution was hydrogenated at atmospheric pressure in presence of Raney nickel (1 teaspoonful) for 3 hours. The catalyst was filtered off and the filtrate was evaporated. Crystallization of the residue from 2-propanol/ether yielded final product. For analysis it was recrystallized from ethanol/ether, m.p. 217°–219° C.

EXAMPLE 100

8-Chloro-3-chloromethyl-6-(2-chlorophenyl)-1-methyl-4H-imidazo [1,5-a][1,4]benzodiazepine 8-Chloro-6-(2-chlorophenyl)3-hydroxymethyl-1-methyl-4H-imidazo[1,5-a][1,4]benzodiazepine, 3.7 g. (0.01 m) was added with stirring to 20 ml. of thionylchloride. After stirring for 30 minutes at room temperature, the hydrochloride of the product was crystallized by dilution with 30 ml. of ethyl acetate and 100 ml. of ether. The crystals were collected, washed with ether and partitioned between methylene chloride and saturated aqueous sodium bicarbonate solution. The methylene chloride layer was dried and evaporated and the residue was crystallized from ether to yield colorless crystals which did not melt on slow heating but on immersion of the capillary at 200°–210° C. The analytical sample was recrystallized from ethyl acetate/hexane.

EXAMPLE 101

8-Chloro-6-(2-chlorophenyl)-3-dimethylaminomethyl-1-methyl-4-H-imidazo[1,5-a][1,4]benzodiazepine dihydrochloride ethanolate A mixture of 2 g. of 8-chloro-3-chloromethyl-6-(2-chlorophenyl)-1-methyl-4H-imidazo[1,5-a][1,4]benzodiazepine, 10 ml. of dimethylamine and 10 ml. of tetrahydrofuran was heated in a sealed tube at 100° C. for 2 hours. The solvents were evaporated and the residue was partitioned between methylene chloride and 10% aqueous sodium carbonate solution. The organic phase was dried and evaporated and the residue was crystallized from ether to give the base with m.p. 136°–138° C.

This material was dissolved in 10 ml. of ethanol and treated with two equivalents of ethanolic hydrogen chloride. Crystallization by dilution with ether yielded colorless crystals which were recrystallized from ethanol/ether for analysis, m.p. 275°–277° C.

EXAMPLE 102

8-Acetamido-6-(2-fluorophenyl)-1-methyl-4H-imidazo[1,5-a][1,4]benzodiazepine

To 5 ml. of acetic anhydride was added 0.3 g. (0.00082 M) of 8-amino-6-(2-fluorophenyl)-1-methyl-4H-imidazo[1,5-a][1,4]benzodiazepine isopropanolate and the reaction was heated on the steam bath for 1 hour, and then evaporated to dryness. The residue was dissolved in 25 ml. of dichloromethane which was washed with 15 ml. of 5% potassium carbonate solution, dried over anhydrous sodium sulfate and evaporated to dryness. The product was recrystallized twice from a mixture of methanol and ethyl acetate to give product as white. rods, m.p. 326°–331°.

EXAMPLE 103

6-(2-Fluorophenyl)-1-methyl-8-(N-methylacetamido)-4H-imidazo[1,5-a][1,4]benzodiazepine A solution of 0.8 g. (0.0024 g.) of 8-acetamido-6-(2-fluorophenyl)-1-methyl-4H-imidazo[1,5-a][1,4]benzodiazepine in 10 ml. of dry N,N-dimethylformamide under nitrogen was treated with 0.13 g. (0.003 m) of 55% sodium hydride in mineral oil and after 30 minutes the reaction mixture was cooled in an ice bath. To the stirred reaction 0.43 g. (0.003 m) of methyl iodide was added and after 18 hours at room temperature the reaction mixture was poured into water. Filtration afforded the crude product which was recrystallized from a mixture of ethyl acetate and ether to give product as off white prisms, m.p. 217°–223°.

EXAMPLE 104

6-(2-Fluorophenyl)-1-methyl-8-methylamino-4H-imidazo[1,5-a][1,4]benzodiazepine

A solution of 0.3 g. (0.000828 m) of 6-(2-fluorophenyl)-1-methyl-8-(N-methylacetamido)-4H-imidazo[1,5-a][1,4]benzodiazepine in 10 ml. of methanol was treated with 3 ml. of concentrated hydrochloric acid and refluxed for 1 hour. The solution was made basic with ammonium hydroxide and then partitioned between 50 ml. of dichloromethane and 50 ml. of water. The organic phase was dried over anhydrous sodium sulfate and evaporated to dryness. The residual oil was dissolved in 10 ml. of dichloromethane and filtered through Florisil. It was eluted with ether, ethyl acetate and finally ethyl acetate containing 5% methanol. This last mixture was evaporated, and crystallized from a mixture of ethyl acetate and ether to give product as off white prisms, m.p. 255°–259°.

EXAMPLE 105

(2-Fluorophenyl)-[2-(5-hydroxymethyl-2-methyl-1-imidazolyl)-5-nitrophenyl]methanone A solution of 0.3 g. (0.00082 m) of 8-amino-6-(2-fluorophenyl)-1-methyl-4H-imidazo[1,5-a][1,4]benzodiazepine isopropanolate in 0.5 ml. of sulfuric acid was treated with 4 g. of ice followed by 0.2 g. (0.0029 m) of sodium nitrite. After 5 minutes this was added to a fresh solution prepared by adding 1 g. (0.00625 m) of copper sulfate in 10 ml. of water to 1 g. (0.00794 m) of sodium sulfite in 5ml. of water and then adding this to 8 g. (0.116 m) of sodium nitrite in 40 ml. of water. After 15 minutes the reaction was warmed to 35° for 5 minutes, made basic with 10% potassium carbonate solution and extracted with 100 ml. of dichloromethane. The organic layers were combined, dried over anhydrous sodium sulfate, concentrated and applied to a silica gel thick layer plate. This was developed in a mixture of ethyl acetate and ethanol (10/1), and the spot having an Rf of 0.5 was scraped off. Crystallization from methanol and recrystallization from a mixture of dichloromethane and ether gave product as off white prisms, m.p. 188°-192°.

EXAMPLE 106

A.
(2-Fluorophenyl)[2-(2-methyl-5-dimethylaminomethyl-1-imidazolyl)-5-dimethylaminophenyl]methanone dipicrate.

A solution of 0.5 g. (0.00137 m) of 8-amino-6-(2-fluorophenyl)-1-methyl-4H-imidazo[1,5-a][1,4] benzodiazepine isopropanolate in 20 ml. of formic acid and 5 ml. (0.062 m) of 37% formaldehyde was heated on the steam bath for 3 hours, and then evaporated to dryness. The residue was dissolved in 50 ml. of dichloromethane, which was washed with 15 ml. of 10% potassium carbonate solution, dried over anhydrous sodium sulfate and concentrated. The residual oil was applied to and developed on 2 silica gel thick layer plates in a mixture of ethyl acetate and ethanol (7/1). The material having an Rf of 0.4 was scraped off, washed with methanol, filtered and evaporated. The oil was dissolved in ether and 5 ml. of a 10% ethanolic solution of picric acid was added. The precipitate was filtered and recrystallized from a mixture of tetrahydrofuran and isopropanol to give the product as yellow prisms, m.p. 228°-230°.

B. From 8-amino-6-(2-fluorophenyl)-1-methyl-4H-imidazo[1,5-a][1,4]benzodiazepine isopropanolate To a mixture of 0.1 g. (0.000273 m) and 5 ml. of water was added 1 ml. of concentrated hydrochloric acid. The reaction was cooled in an ice bath and 0.15 g. (0.00217 m) of sodium nitrite was added slowly with stirring. After 1 hour the reaction mixture was poured into a solution of 0.2 g. (0.00202 m) of cuprous chloride in 50 ml. of water which had been heated to 70°. After 18 hours the reaction was made basic with sodium hydroxide, extracted with dichloromethane (2×50 ml.), dried over anhydrous sodium sulfate and evaporated to dryness. The residue was developed on a silica gel thick layer plate in a mixture of ethyl acetate and methanol (10/1). The product which had an Rf of 0.7 as scraped off the plate, stirred with methanol and filtered. Evaporation and crystallization of the crude product from a mixture of ethyl acetate and ether gave product as white prisms, m.p. and mmp with an authentic sample 159°-166°.

EXAMPLE 107

(2-Fluorophenyl)-[2-(5-hydroxymethyl-2-methyl-1-imidazolyl)-5-chlorophenyl]methanone

A. From 8-chloro-6-(2-fluorophenyl)-1-methyl-4H-imidazo[1,5-a][1,4]benzodiazepine A solution of 3 g. (0.00920 m) of 8-chloro-6-(2-fluorophenyl)-1-methyl-4H-imidazo[1,5-a][1,4]benzodiazepine in 50 ml. of water and 0.5 ml. (0.4092 m) of concentrated sulfuric acid was treated with 1.5 g. (0.0217 m) of sodium nitrite. After 18 hours an additional 0.5 ml. of sulfuric acid and 1.5 g. of sodium nitrite was added, and after 10 minutes the reaction was made basic with 10 N sodium hydroxide. The reaction mixture was extracted with 75 ml. of dichloromethane, which was dried over anhydrous sodium sulfate and evaporated to dryness. Crystallization of the residue from a mixture of ethyl acetate and ether gave the product as white prisms, m.p. 165°-168°.

B. From 5-aminomethyl-1-[4-chloro-2-(2-fluorobenzoyl)phenyl]-2-methylimidazole dihydrochloride A solution of 1 g. (0.00240 m) of 5-aminomethyl-1-[4-chloro-2-(2-fluorobenzoyl)phenyl]-2-methylimidazole dihydrochloride was dissolved in 20 ml of water and 1 g. (0.0145 m) of sodium nitrite was added slowly with stirring in an ice bath. After 3 hours the reaction was made basic with 10 N sodium hydroxide and extracted with 50 ml. of dichloromethane. The organic phase was dried over anhydrous sodium sulfate and evaporated to dryness. Crystallization from ethyl acetate gave product as white prisms, m.p. and mmp with a sample prepared as above 163°-166°.

EXAMPLE 108

8-Chloro-6-(2-fluorophenyl)-1-methyl-4H-imidazo[1,5-a][1,4]benzodiazepine

A solution of 0.5 g. (0.00145 m) of (2-fluorophenyl)-[2-(5-hydroxymethyl-2-methyl-1-imidazolyl)-5-chlorophenyl]methanone in 25 ml. of dichloromethane was treated with 0.15 ml. (0.00155 m) of phosphorous tribromide in an ice bath and after 1 hour at room temperature was poured into 50 ml. of liquid ammonia. After the ammonia had evaporated the reaction was partitioned between 50 ml. of dichloromethane and water. The organic phase was separated and dried over anhydrous sodium sulfate. The solution was concentrated and the residue was applied to 2 silica gel thick layer plates which were developed in a mixture of ethyl acetate/10% methanol.

The compound which had an Rf of 0.6 was scraped off, stirred with methanol and filtered. The solution was treated with 0.1 g. (0.000962 m) of maleic acid and evaporated. The residual salt was crystallized from a mixture of isopropanol and ether to give the maleate of the above product as white prisms, m.p. and mmp with an authentic sample 112°-115°. * The base was obtained by partitioning the salt between dichloromethane and water, adjusting the pH, separating the layers and evaporating the organic phase. Crystallization of the product from ether gave white prisms, m.p. and mmp with an authentic sample 154°-157°.

*mp of solvated product

EXAMPLE 109

8-Chloro-3-methoxymethyl-1-methyl-6-phenyl-4H-imidazo[1,5-a][1,4]benzodiazepine

A solution of 1.7 g. (0.005 m) of 8-chloro-3-hydroxymethyl-1-methyl-6-phenyl-4H-imidazo[1,5-a][1,4]benzodiazepine in 5 ml. of thionyl chloride was stirred at room temperature for 30 minutes. The hydrochloride of 8-chloro-3-chloromethyl-1-methyl-6-phenyl-4H-imidazo[1,5-a][1,4]benzodiazepine was crystallized by addition of ethylacetate and ether. The collected crystals were partitioned betweeen methylene chloride and saturated aqueous sodium bicarbonate solution. The organic phase was dried and evaporated. Crystallization of the residue from methylene chloride/ether yielded 8-chloro-3-chloromethyl-1-methyl-6-phenyl-4H-imidazo[1,5-a][1,4]benzodiazepine which was heated to reflux for 10 minutes in 50 ml. of methanol containing 0.5 g. of sodium methoxide. The methanol was evaporated and the residue was partitioned between methylene chloride and saturated sodium bicarbonate solution. The organic phase was dried and evaporated.

Chromatography of this crude material over 30 g. of silica gel using methylene chloride/ethyl acetate 1:3 (v/v) yielded colorless crystals with m.p. 163°–165° C., crystallized from ethylacetate/hexane.

EXAMPLE 110

8-Chloro-6-(2-chlorophenyl)-3-cyanomethyl-1-methyl-4H-imidazo [1,5-a][1,4]benzodiazepine A mixture of 1 g. of 8-chloro-3-chloromethyl-6-(2-chlorophenyl)-1-methyl-4H-imidazo[1,5-a][1,4]benzodiazepine, 250 mg. of potassium cyanide and 20 ml. of dimethylformamide was heated on the steambath with stirring for 3 hours. After dilution with water, the mixture was extracted with methylene chloride. The extracts were washed with water, dried and evaporated. Chromatography of the residue on 30 g. of silica gel using methylene chloride/ethyl acetate 1:2 and crystallization of the clean fractions from ether yielded final product with m.p. 212°–214° C. The analytical sample was recrystallized from ethyl acetate/hexane, m.p. 215°–217° C.

EXAMPLE 111

8-Chloro-3-(N-methoxyiminomethyl)-1-methyl-6-phenyl-4H-imidazo[1,5-a][1,4]benzodiazepine Triethylamine, 2 ml., and 0.5 g. of methoxyamine hydrochloride was added to a warm solution of 0.67 g. (0.002 m) of 8-chloro-1-methyl-6-phenyl-4H-imidazo[1,5-a][1,4]benzodiazepine-3-carboxaldehyde in 40 ml. of ethanol. The mixture was allowed to sit for 30 minutes. The solvent was partially evaporated and the product was crystallized by diluting with water. The crystals were collected and dried to leave final product. The analytical sample was recrystallized from ether, m.p. 193°–195° C.

EXAMPLE 112

8-Chloro-6-(2-chlorophenyl)-1-methyl-4H-imidazo[1,5-a][1,4]benzodiazepine-3-carboxaldehyde dimethylhydrazone hemiethanolate A mixture of 370 mg. (1 mmol) of 8-chloro-6-(2-chlorophenyl)-1-methyl-4H-imidazo[1,5-a][1,4]benzodiazepine-3-carboxaldehyde, 10 ml. of ethanol and 0.5 ml. of 1,1-dimethylhydriazine was heated to reflux for 15 minutes. The solvent was evaporated and the residue was crystallized from ethanol/water to yield light yellow crystals. The analytical sample was recrystallized from ethanol, m.p. 238°–242° C. The crystals contained according to nmr-spectrum and analysis 0.5 equivalent of ethanol.

EXAMPLE 113

6-(2-Chlorophenyl)-1-methyl-8-nitro-4H-imidazo[1,5-a][1,4]benzodiazepine-3-carboxamide Phosphorus pentachloride, 1.1 g. (5.2 mmol), was added to a suspension of 1.6 g. (4 mmol) of 6-(2-chlorophenyl)-1-methyl-8-nitro-4H-imidazo[1,5-a][1,4]benzodiazepine 3-carboxylic acid in 100 ml. of methylene chloride cooled in ice-water. After stirring for 30 minutes in ice-water, a stream of ammonia was introduced until the mixture was alkaline and stirring was continued for one hour at room temperature. Water was added and the organic layer was separated, dried and evaporated. Crystallization of the residue from methanol/ethyl acetate yielded yellowish crystals with mp>300°. The analytical sample was recrystallized from the same solvents.

EXAMPLE 114

2-[(Benzoylamino)methoxycarbonylmethylene]-7-chloro-5-(2-fluorophenyl)-1,3-dihydro-2H-1,4-benzodiazepine A solution of 3.75 g. (0.01 m) of 7-chloro-5-(2-fluorohenyl)-alphahydroxyimino-3H-1,4-benzodiazepine-2-acetic acid methyl ester in 300 ml. of tetrahydrofuran and 200 ml. of methanol was hydrogenated at atmospheric pressure for 1½ hour in presence of one teaspoonful of Raney nickel. The catalyst was separated by filtration over celite and the filtrate was evaporated under reduced pressure, at the end azeotropically with toluene. The residue was dissolved in 20 ml. of pyridine and treated with 4 ml. of benzoylchloride. After sitting at room temperature for 15 minutes, the reaction mixture was partitioned between methylene chloride and 1 N sodium hydroxide solution. The organic layer was dried and evaporated, at the end azeotropically with toluene. Crystallization of the residue from ether yielded final product with m.p. 210°–213° C. The analytical sample was recrystallized from ethyl acetate/hexane, m.p. 217°–219° C. with softening at 150°–160° C.

EXAMPLE 115

1-Methyl-8-(2-methyl-1,3-dioxolan-2-yl)-6-phenyl-4H-imidazo[1,5-a][1,4]benzodiazepine maleate hemimethanolate Hydrogenation of 5 g. (0.0137 m) of 2,3-dihydro-7-(1-methyl-1,3-dioxolan-2-yl)-2-nitromethylene-5-phenyl-1H-1,4-benzodiazepine in 250 ml. of absolute ethanol in the presence of 1 teaspoon of Raney nickel for 3.5 hours yielded crude 2-aminomethyl-2,3-dihydro-7-(1-methyl-1,3-dioxolan-2-yl)-5-phenyl-1H-1,4-benzodiazepine. To a solution of 4 g. (0.0119 m) of this compound in 75 ml. of absolute ethanol was added 0.7 g. (0.0037 m) of p-toluene sulfonic acid and 6 g. (0.037 m) of triethyl orthoacetate. The mixture was refluxed for 2 hours, evaporated to dryness and the residue was dissolved in 50 ml. of dichloromethane. This was washed with 25 ml. of dilute ammonium hydroxide, dried over anydrous sodium sulfate and evaporated to give crude 3a,4-dihydro- 1-methyl-8-(1-methyl-1,3-dioxolan-2-yl)-6-phenyl-3H-imidazo[1,5-a][1,4]benzodiazepine as an oil.

A solution containing 3.8 g. (0.0105 m) of this crude oil, and 18 g. of activated manganese dioxide in 100 ml. of toluene was refluxed and stirred for 2 hours using a Dean Stark trap. It was filtered and washed with a mixture of 250 ml. of dichloromethane and 250 ml. of tetrahydrofuran. The filtrates were evaporated and dissolved in a small amount of isopropanol and treated with 1.4 g. (0.0121 m) of maleic acid in ethanol. Ether was added and the precipitate was filtered and recrystallized from a mixture of methanol and ether to give the above product as off white prisms, m.p. 179°–182°.

EXAMPLE 116

8-Acetyl-1-methyl-6-phenyl-4H-imidazo[1,5-a][1,4]benzodiazepine dipicrate

A solution of 0.3 g. (0.1000607 m) of 1-methyl-8-(2-methyl-1,3-dioxolan-2-yl)-6-phenyl-4H-imidazo[1,5-a][1,4]benzodiazepine maleate hemimethanolate in 10 ml. (0.01 m) of 1 N hydrochloric acid was allowed to stand for 18 hours. A small amount of charcoal was added and the reaction mixture was filtered. The solution was made basic with ammonium hydroxide, extracted with 25 ml. of dichloromethane, dried over anhydrous sodium sulfate and evaporated to dryness. The residue was dissolved in isopropanol and 0.35 g. (0.10015 m) of picric acid in 5 ml. of ethanol was added. The solution was evaporated and the residue was crystallized from methanol. Recrystallization from a mixture of tetrahydrofuran and isopropanol gave the product as yellow prisms, m.p. 225°–230°.

EXAMPLE 117

8-(1-Hydroxyethyl)-1-methyl-6-phenyl-4H-imidazo[1,5-a][1,4]benzodiazepine dipicrate A solution of 1 g. (0.00317 m) of 8-acetyl-1-methyl-6-phenyl-4H-imidazo[1,5-a][1,4]benzodiazepine dipicrate in 75 ml. of absolute ethanol was treated with 0.78 g. (0.0205 m) of sodium borohydrode and after 18 hours the solution was evaporated to dryness. The residue was acidified with dilute acetic acid, made basic with ammonium hydroxide and the mixture was extracted with 75 ml. of dichloromethane. The organic layers were combined, dried over anhydrous sodium sulfate and evaporated to dryness. The oil thus obtained was dissolved in isopropanol and 1.6 g. (0.007 m) of picric acid in 20 ml. of ethanol was added. The precipitated salt was filtered and recrystallized twice from methanol to give the above product as yellow rods, m.p. 223°–225°.

EXAMPLE 118

8-(1-Hydroxyethyl)-1-methyl-6-phenyl-5,6-dihydro-4H-imidazo[1,5-a][1,4]benzodiazepine dipicrate The filtrates from the reaction of Example 117 were concentrated and crude product was filtered off. Recrystallization twice from a mixture of tetrahydrofuran and methanol gave pure product as yellow rods, m.p. 143°–145°.

EXAMPLE 119

7-Cyano-5-(2-fluorophenyl)-2-bis-(morpholino)phosphinyloxy-3H-1,4-benzodiazepine A solution of 10 g. (0.0358 m) of 7-cyano-2,3-dihydro-5-(2-fluorophenyl)-1H-1,4-benzodiazepin-2-one in 150 ml. of dry tetrahydrofuran under argon was treated with 2.4 g. (0.0537 m) of 54% sodium hydride and the reaction was stirred and refluxed for 1 hour. This was cooled to 0° and 13.7 g. (0.0537 m) of phosphorodimorpholidic chloride was added. After 18 hours the reaction mixture was filtered, concentrated to a small volume and ether was added. The precipitate was filtered and recrystallized from a mixture of dichloromethane and ether to give product as white rods, m.p. 194°–197°.

EXAMPLE 120

Ethyl 8-cyano-6-(2-fluorophenyl)-1-methyl-4H-imidazo[1,5-a][1,4]benzodiazepine-3-carboxylate; and (Acetylamino)[7-cyano-5-(2-fluorophenyl)-3H-1,4-benzodiazepine-2-yl]malonic acid diethyl ester To 100 ml. of dry N,N-dimethylformamide under nitrogen was added 1.6 g. (0.036 m) of 54% sodium hydride, and 8.3 g. (0.038 m) of acetamidodiethyl malonate was added with stirring. After 30 minutes 10 g. (0.02 m) of 7-Cyano-5-(2-fluorophenyl)-2-bis(morpholino)phosphinyloxy-3H-1,4-benzodiazepine was added and after 64 hours the reaction was poured into ice water containing 4 ml. of acetic acid. This was filtered and the solid was dissolved in 100 ml of dichloromethane, which was washed with 50 ml. of water, dried over anhydrous sodium sulfate and concentrated to a small volume. This solution was chromatographed over a column of Florisil and eluted with 2 l. of dichloromethane which was discarded. It was then eluted with 1 l. of a mixture of dichloromethane and ether (10/1) and then with 2 l. of ether. The ether fraction was recrystallized twice from a mixture of dichloromethane and ether to give (acetylamino)[7-cyano-5-(2-fluorophenyl)-3H-1,4-benzodiazepine-2-yl]malonic acid diethyl ester as white prisms, m.p. 138°–140°.

The column was eluted with 1.5 l. of a mixture of ethyl acetate and methanol (10/1). The eluent was concentrated and the residue was crystallized from ether. Recrystallization from a mixture of dichloromethane and ether gave ethyl 8-cyano-6-(2-fluorophenyl)-1-methyl-4H-imidazo[1,5-a][1,4]benzodiazepine-3-carboxylate as off white prisms, m.p. 272°–274°.

EXAMPLE 121

8-Cyano-6-(2-fluorophenyl)-1-methyl-4H-imidazo[1,5-a][1,4]benzodiazepine

A solution of 0.5 g. (0.00129 m) of ethyl 8-cyano-6-(2-fluorophenyl)-1-methyl-4H-imidazo[1,5-a][1,4]benzodiazepine-3-carboxylate in 100 ml. of ethanol and 10 ml. of water was treated with 0.14 g. (0.0026 m) of potassium hydroxide. After refluxing for 30 minutes the reaction was evaporated and 10 ml. of water was added. This was acidified with acetic acid, filtered and extracted with 20 ml. of dichloromethane, which was separated, dried and evaporated. About 0.2 g. of the hydrolyzed product was obtained from the filtration, and the same amount was obtained from the extraction. This material was added to 3 ml. of dry hexamethylphosphoramide and kept at 200°–205° for 30 minutes under argon. It was cooled and 50 ml. of ice water and 1 ml. of ammonium hydroxide were added. The solution was filtered and the filtrates were extracted with 25 ml. of dichloromethane and evaporated to dryness. Water was added and the solution was filtered and the combined precipitates were dissolved in dichloromethane and developed on 2 silica gel thick layer plates in a solution of ethyl acetate containing 15% methanol. The silica gel containing the product was scraped off (Rf 4–5), stirred with methanol and filtered. This was crystallized from a mixture of isopropanol and ether to give the desired product as off white prisms, m.p. 198°–203°.

EXAMPLE 122

7-Aminomethyl-1,3-dihydro-5-(2-fluorophenyl)-2H-1,4-benzodiazepin-2-one picrate

A solution of 1 g. (0.00358 m) of 7-cyano-2,3-dihydro-5-(2-fluorophenyl)-1H-1,4-benzodiazepin-2-one was hydrogenated in the presence of 0.5 teaspoon of Raney nickel for a period of 5 hours and was then allowed to stand for 18 hours more without stirring. The reaction mixture was filtered through Celite and concentrated to a small volume. A solution of 0.9 g. (0.004 m) of picric acid in 10 ml. of ethanol was added. The precipitated salt was filtered and recrystallized twice from a mixture of tetrahydrofuran and methanol to give product as yellow prisms, m.p. 194°–198°.

EXAMPLE 123

8-Chloro-6-(2-fluorophenyl)-5,6-dihydro-1-methyl-5-(4-methylphenylsulfonyl)-4H-imidazo[1,5-a][1,4]benzodiazepine To a solution of 1.6 g. (5 mmoles) of 8-chloro-5,6-dihydro-6-(2-fluorophenyl)-1-methyl-4H-imidazo[1,5-a][1,4]benzodiazepine in 10 ml. of pyridine was added 1.2 g. (6 mmoles) of p-toluenesulfonyl chloride. After standing at room temperature for 19 hours, the reaction mixture was diluted with water and extracted with methylene chloride. The organic extract was dried and concentrated in vacuo to dryness. The residue was crystallized from a mixture of methylene chloride, ether and gave product melting at 252°–253°. After recrystallizatin from tetrahydrofuran the pure product formed yellow prisms with the same melting point.

EXAMPLE 124

5-Acetyl-8-chloro-6-(2-fluorophenyl)-5,6-dihydro-1-methyl-4H-imidazo[1,5-a][1,4]benzodiazepine A solution of 1.5 g. of 8-chloro-5,6-dihydro-6-(2-fluorophenyl)-1-methyl-4H-imidazo[1,5-a][1,4]benzodiazepine in a mixture of 10 ml. pyridine and 5 ml. of acetic anhydride was left at room temperature for 18 hours. The reaction mixture was concentrated in vacuo to dryness. The residue was dissolved in methylene chloride and washed with dilute potassium hydroxide. The organic layer was separated, dried and concentrated in vacuo to dryness. The residue was crystallized from a mixture of methylene chloride, ether, petroleum ether and gave product melting at 185°–186°. After recrystallization from methylene chloride the pure product formed colorless prisms melting at 186°–187°.

EXAMPLE 125

8-Chloro-6-(2-fluorophenyl)-5,6-dihydro-5-nitroso-1-methyl-4H-imidazo[1,5-a][1,4]benzodiazepine To a stirred solution of 1.6 g. of 8-chloro-5,6-dihydro-6-(2-fluorophenyl)-1-methyl-4H-imidazo[1,5-a][1,4]benzodiazepine in 10 ml. acetic acid was added slowly 0.4 g. of sodium nitrite. After stirring for 1.5 hours the reaction mixture was poured into ice water, made alkaline with 50% potassium hydroxide and extracted with methylene chloride. The organic extract was separated, dried and concentrated in vacuo to dryness. The residue was crystallized from a mixture of methylene chloride, ether and gave product melting at 238°–240°. After recrystallization from the same solvent mixture the pure product formed colorless prisms with unchanged melting point.

EXAMPLE 126

8-Chloro-6-(2-fluorophenyl)-5,6-dihydro-1,5-dimethyl-4H-imidazo[1,5-a][1,4]benzodiazepine To a solution of 1.6 g. (5 mmoles) of 8-chloro-5,6-dihydro-6-(2-fluorophenyl)-1-methyl-4H-imidazo[1,5-a][1,4]benzodiazepine in 5 ml. of formic acid was added 2.4 ml. of 37% formaldehyde. The reaction mixture was heated on the steambath for 5 hours, then poured into ice water, made alkaline with 50% potassium hydroxide and extracted with methylene chloride. The organic extract was separated, dried and concentrated in vacuo to dryness. The residue was crystallized from ether and gave product melting at 156°–158°. After recrystallization from ether the pure product formed colorless prisms melting at 158°–159°.

EXAMPLE 127

5-Allyl-8-chloro-6-(2-fluorophenyl)-5,6-dihydro-1-methyl-4H-imidazo[1,5-a][1,4]benzodiazepine To a stirred solution of 0.98 g. (3 mmoles) of 8-chloro-5,6-dihydro-6-(2-fluorophenyl)-1-methyl-4H-imidazo[1,5-a][1,4]benzodiazepine in 25 ml. of dry dimethylformamide was added 0.2 g. (4.3 mmoles) of 57% sodium hydride. After 15 minutes 0.4 ml. (4.3 mmoles) of allylbromide was added and the stirring continued for 6 hours. The reaction mixture was poured into ice water and extracted with a mixture of ether and petroleum ether. The organic layer was separated, dried and concentrated in vacuo to dryness. The residue was crystallized from a mixture of ether/petroleum ether and gave product melting at 140°–145°. After recrystallization from ether the pure product formed colorless prisms, melting at 153°–154°.

EXAMPLE 128

8-Chloro-6-(2-fluorophenyl)-5,6-dihydro-5-hydroxy-1-methyl-4H-imidazo[1,5-a][1,4]benzodiazepine To a stirred solution of 1.2 g. (3.5 mmoles) of 8-chloro-6-(2-fluorophenyl-1-methyl-4H-imidazo[1,5-a][1,4]benzodiazepine 5-oxide in 120 ml. of ethanol was added slowly 1.2 g. (31 mmoles) of sodium borohydride. After stirring for 4.5 hours at room temperature the reaction mixture was diluted with about 175 ml. of water and produced melting at 246°–248° was separated by filtration. After recrystallization from a mixture of methylene chloride/ether, the pure product formed colorless needles melting at 251°–252°.

EXAMPLE 129

8-Chloro-6-(2-fluorophenyl)-1-methyl-4H-imidazo[1,5-a][1,4]benzodiazepine

A. From 8-chloro-6-(2-fluorophenyl)-5,6-dihydro-1-methyl-5-(4-methylphenylsulfonyl)-4H-imidazo[1,5-a][1,4]benzodiazepine To a stirred solution of 2.4 g. (5 mmoles) of 8-chloro-6-(2-fluorophenyl)-5,6-dihydro-1-methyl-5-(4-methylphenylsulfonyl)-4H-imidazo[1,5-a][1,4]benzodiazepine in 120 ml. of dry tetrahydrofuran was added 1.1 g. of potassium tert-butoxide. After stirring at room temperature for 2 hours the reaction mixture was poured into ice water and extracted with a 50% mixture of ether and petroleum ether. The organic extract was dried and concentrated in vacuo to dryness. The residue was crystallized from a mixture of ether, petroleum ether and gave product melting at 152°–153°. The mixed melting point with an authentic sample gave no depession.

B. From 8-chloro-6-(2-fluorophenyl)-5,6-dihydro-5-nitroso-1-methyl-4H-imidazo[1,5-a][1,4]benzodiazepine To a stirred solution of 1.7 g. (4.7 mmoles) of 8-chloro-6-(2-fluorophenyl)5,6-dihydro-5-nitroso-1-methyl-4H-imidazo[1,5-a][1,4]benzodiazepine in 25 ml. of dry dimethylformamide was added 0.6 g. (5 mmoles) of potassium t-butoxide. After 5 minutes the reaction mixture was poured into ice water and extracted with methylene chloride. The organic layer was separated, dried and concentrated in vacuo to dryness. The residue dissolved in methylene chloride was filtered over 12 g. Woelm I alumina and the filter bed washed with the same solvent. The filtrate (ca. 120 ml.) was concentrated in vacuo to dryness. The residue was crystallized from ether and gave product melting at 139°–145°. After recrystallization from ether the product melted at 153°–155° and a mixed melting point with an authentic sample gave no depression.

C. From 8-chloro-6-(2-fluorophenyl)-5,6-dihydro-5-hydroxy-1-methyl-4H-imidzo[1,5-a][1,4]benzodiazepine A solution of 0.3 g. of 8-chloro-6(2-fluorophenyl)-5,6-dihydro-5-hydroxy-1-methyl-4H-imidazo[1,5-a][1,4]benzodiazepine in a mixture of 10 ml. of pyridine and 2 ml. of acetic anhydride was left at room temperature for 19 hours. The reaction mixture was concentrated in vacuo to dryness. The residue was dissolved in 20 ml. of methanol and 0.2 g. of sodium methoxide added. After standing at room temperature for 45 minutes, the reaction mixture was concentrated in vacuo to dryness. The residue was partitioned between methylene chloride and water. The organic layer was separated, dried and concentrated in vacuo to dryness. The residue was crystallized from a methylene chloride/ether mixture and gave starting material melting at 255°–256°. Concentration of the filtrate and crystallization of the residue from ether gave the desired product melting at 158°–160°. The mixed melting point with an authentic sample gave no depression.

EXAMPLE 130

2-Aminomethyl-7-chloro-2,3,4,5-tetrahydro-5-(2-fluorophenyl)-1H-1,4-benzodiazepine To a stirred solution of 27.8 g. (92 mmoles) of DL-2-aminomethyl-7-chloro-2,3-dihydro-5-(2-fluorophenyl)-1H-1,4-benzodiazepine in a mixture of 450 ml. of methylene chloride and 300 ml. of acetic acid was added slowly 27.8 g. of zinc dust. After stirring at room temperature for 4 hours the reaction mixture was filtered over Celite. The filtrate was diluted with ice water, made alkaline with 50% potassium hydroxide solution and extracted with methylene chloride. The organic extract was separated, dried and concentrated in vacuo to dryness. The residue was crystallized from ether and gave product melting at 119°–120°. After recrystallization from ether the pure product formed slightly yellow prisms melting at 127°–128°.

The hydrochloride was prepared by treating a solution of the base in isopropanol with an excess of concentrated hydrochloric acid. After recrystallization of the salt from a mixture of water and isopropanol the pure product formed slightly yellow needles melting at 268°–271°.

EXAMPLE 131

8-Chloro-6-(2-fluorophenyl)-3a,4,5,6-tetrahydro-1-methyl-3H-imidazo[1,5-a][1,4]benzodiazepine (Isomer A)

Method A. From rac. 2-aminomethyl-7-chloro-2,3,4,5-tetrahydro-1-methyl-3H-imidazo[1,5-a][1,4]benzodiazepine A solution of 3 g. (10 mmoles) of 2-aminomethyl-7-chloro-2,3,4,5-tetrahydro-1-methyl-3H-imidazo[1,5-a][1,4]benzodiazepine in a mixture of 30 ml. of xylene and 10 ml. of triethylorthoacetate (97%) was refluxed for 4 hours. The reaction mixture was diluted with ether and extracted with dilute ice cold hydrochloric acid. The acid extract was made alkaline with dilute potassium hydroxide and extracted with methylene chloride. The organic layer was separated, dried and concentrated in vacuo to dryness. The residue was crystallized from ether and gave product melting at 187°–189°. After recrystallization from a mixture of methylene chloride and ether the pure product formed slightly yellow prisms melting at 189°–190°.

Method B. From 8-chloro-3a,4-dihydro-6-(6-fluorophenyl)-1-methyl-3H-imidazo[1,5-a][1,4]-benzodiazepine To a stirred solution of 2.5 g. of 8-chloro-3a,4-dihydro-6-(2-fluorophenyl)-1-methyl-3H-imidazo[1,5a][1,4-]benzodiazepine in a mixture of 100 ml. methylene chloride and 25 ml. of acetic acid was added slowly 2.5 g. of zinc dust. After stirring at room temperature for 4 hours, the reaction mixture was filtered over Celite. The filtrate was diluted with ice water, made alkaline with 50% potassium hydroxide and extracted with methylene chloride. The organic extract was separated, dried and concentrated in vacuo to dryness. The residue was crystallized from ether and gave product which was identical with the product prepared above, m.p. and mmp 189°–190°.

EXAMPLE 132

8-Chloro-6-(2-fluorophenyl)-3a,4,5,6-tetrahydro-1-methyl-3H-imidazo[1,5-a][1,4]benzodiazepine (Isomer B)

A solution of 3.2 g. (10 mmoles) of 8-chloro-3a,4-dihydro-6-(2-fluorophenyl)-1-methyl-3H-imidazo[1,5-a][1,4]benzodiazepine in 50 ml. acetic acid and 10 ml. of water was hydrogenated at room temperature and atmospheric pressure in the presence of 0.4 g. of prehydrogenated platinum oxide. After 15 minutes, 10 mmoles of hydrogen was absorbed. The catalyst was separated by filtration and the filtrate concentrated in vacuo to dryness. The residue was dissolved in methylene chloride and washed with an excess of ice cold dilute sodium carbonate. The organic layer was separated, dried and concentrated in vacuo to dryness. The residue was crystallized from a mixture of ether/petroleum ether and gave product melting at 108°–110°.

After recrystallization from ether the pure product formed colorless prisms melting at 110°–112°.

EXAMPLE 133

8-chloro-6-(2-fluorophenyl)-1-methyl-4H-imidazo[1,5-a][1,4]benzodiazepine

A mixture of 2.9 g. of 8-chloro-6-(2-fluorophenyl)-3a,4,5,6-tetrahydro-1-methyl-3H-imidazo[1,5-a][1,4]benzodiazepine, 90 ml. of toluene and 15 g. of activated manganese dioxide was stirred and refluxed for 2 hours. The reaction was filtered over Hyflo and the filtrate concentrated in vacuo to dryness. The residue was crystallized from ether and gave product which gave no melting point depression with an authentic sample.

EXAMPLE 134

2-Chloro-13a-(2-fluorophenyl)-12,13a-dihydro-6-methyl-9H,11H-imidazo[1,5-a]oxazolo[3,2-d][1,4]benzodiazepine, and maleate A solution of 5 g. (0.00153 m) of 8-chloro-6-(2-fluorophenyl)-1-methyl-4H-imidazo[1,5-a][1,4]benzodiazepine in 75 ml. of dry ethylene dichloride was cooled in an ice bath and 5 g. (0.0352 m) of boron trifluoride etherate was added. After 10 minutes a solution of 4 g. (0.092 m) of ethylene oxide in 5 ml. of ethylene dichloride was added with stirring. After 1 hour at room temperature the mixture was made basic with a solution of potassium carbonate in water. The organic layer was separated, dried over anhydrous sodium sulfate, and evaporated. The residue was dissolved in 50 ml. of dichloromethane and filtered through 150 g. of Florisil. The Florisil was eluted with 750 ml. of dichloromethane and then with 750 ml. of ether.

The dichloromethane solution was evaporated and partitioned between 100 ml. of ether and 100 ml. of 0.5 N hydrochloric acid. The acid layer was separated, made basic with ammonium hydroxide and extracted with 100 ml. of dichloromethane which was dried and evaporated. The oil was dissolved in 15 ml. of isopropanol and 0.8 g. (0.0069 m) of maleic acid was added. The solution was warmed on the steam bath for 5 minutes, cooled and ether was added. The precipitate was filtered, and recrystallized from a mixture of methanol and ether to give the maleate of the above product as white prisms, m.p. 195°–200°.

The ether solution from the Florisil was concentrated, filtered and recrystallized from ether to give the base as white prisms, m.p. 178°–180°.

EXAMPLE 135

7-Chloro-2,3-dihydro-5-(2-fluorophenyl)-2-trifluoroacetaminomethyl-1H-1,4-benzodiazepine A solution of 2.8 g. (0.00932 m) of DL-2-aminomethyl-7-chloro-2,3-dihydro-5-(2-fluorophenyl)-1H-1,4-benzodiazepine in 40 ml. of dichloromethane was treated with 2.5 g. (0.0119 m) of trifluoroacetic acid anhydride and after 5 minutes it was washed with 15 ml. of a 10% potassium carbonate solution, dried over anhydrous sodium sulfate and evaporated to dryness. The residue was crystallized from dichloromethane and was recrystallized from a mixture of dichloromethane and hexane to give the above product as pale yellow prisms, m.p. 140°–143°.

EXAMPLE 136

5-(2-Fluorophenyl)-7-iodo-2-bis-(morpholino)-phosphinyloxy-3H-1,4-benzodiazepine To a solution of 10 g. (0.0264 m) of 5-(2-fluorophenyl)-1,3-dihydro-7-iodo-2H-1,4-benzodiazepin-2-one in 140 ml. of dry tetrahydrofuran was added 1.8 g. (0.039 m) of 54% sodium hydride under argon with stirring. The reaction was refluxed for 1 hour, cooled to 0°, and 10.8 g. (0.0422 m) of phosphorodimorpholidic chloride was added. After 18 hours the solution was filtered, concentrated to a small volume and ether was added. The product was filtered and recrystallized from a mixture of dichloromethane and ether to give product as white plates, m.p. 104°–112°.

EXAMPLE 137

2,3-Dihydro-5-(2-fluorophenyl)-7-iodo-2-nitromethylene-1H-1,4-benzodiazepine

A solution of 27 g. (0.443 m) of nitromethane in 450 ml. of dry dimethyl sulfoxide was cooled to 0° under argon and then 5.4 g. (0.119 m) of 54% sodium hydride was added with stirring. After 2 hours at room temperature the mixture was cooled to 0° and 39.5 g. (0.066 m) of 5-(2-fluorophenyl)-7-iodo-2-bis(morpholino)-phosphinyloxy-3H-1,4-benzodiazepine was added all at once. The reaction was stirred for 18 hours and then poured into 3 l. of ice and water, which contained 15 ml. of acetic acid. This was filtered, the precipitate was dissolved in 700 ml. of dichloromethane which was then washed with 300 ml. of water, dried over anhydrous sodium sulfate and evaporated to dryness. The residue was crystallized and recrystallized from a mixture of dichloromethane and ether to give product as yellow prisms, m.p. 214°–216°.

EXAMPLE 138

7-Chloro-5-(2-chlorophenyl)-2-dimethoxymalonylidene-1,3-dihydro-2H-1,4-benzodiazepine 7-Chloro-5-(2-chlorophenyl)-2-[bis(morpholino)-phosphinyloxy]3H-1,4-benzodiazepine, 5.3 g. (0.01 m) was added to a mixture of 10 ml. of dimethyl malonate, 20 ml. of dimethylformamide and 2.2 g. (0.02 m) of potassium t-butoxide which had been stirred at room temperature for 5 minutes under nitrogen. The reaction mixture was then stirred and heated on the steam bath for 15 minutes. After addition of 1.5 ml. of glacial acetic acid the product was crystallized by gradually diluting with water. The precipitated crystals were collected, washed with water and dried in vacuo to yield product which was recrystallized for analysis from ethyl acetate, m.p. 205°–207°.

EXAMPLE 139

7-Chloro-5-(2-chlorophenyl)-2,3-dihydro-2-[(methoxycarbonyl)methylene]-1H-1,4-benzodiazepine A mixture of 12.6 g. (0.03 m) of 7-chloro-5-(2-chlorophenyl)-2-dimethoxymalonylidene-1,3-dihydro-2H-1,4-benzodiazepine, 300 ml. of methanol and 2.1 g. (0.0375 m) of potassium hydroxide was heated to reflux under nitrogen for 4½ hours, 200 ml. of methanol were distilled off and the residue was diluted with water. The separated crystals were collected, washed with water and dried to yield product with m.p. 154°–158°. For analysis it was recrystallized from methylene chloride/methanol, m.p. 158°–159°.

EXAMPLE 140

7-Chloro-5-(2-chlorophenyl)-alpha-hydroxyimino-3H-1,4-benzodiazepine-2-acetic acid, methyl ester Sodium nitrite, 2.2 g. (0.031 m) was added in portions over 5 minutes to a stirred solution of 7.2 g. (0.02 m) of 7-chloro-5-(2-chlorophenyl)-1,3-dihydro-2-[methoxycarbonyl)methylene]-1H-1,4-benzodiazepine in 75 ml. of glacial acetic acid. After stirring for additional 15 minutes, the mixture was diluted with 100 ml. of water and the precipitated crystals were collected, washed with water, methanol and ether to leave crude product which was recrystallized from tetrahydrofuran/methanol to yield light yellow crystals with m.p. 223°–225° dec.

EXAMPLE 141

Methyl 8-chloro-6-(2-chlorophenyl)-1-methyl-4H-imidazo[1,5-a][1,4]benzodiazepine-3-carboxylate A solution of 3.9 g. (0.01 m) of 7-chloro-5-(2-chlorophenyl)-alpha-hydroxyimino-3H-1,4-benzodiazepine-2-acetic acid, methyl ester in 100 ml. of tetrahydrofuran and 50 ml. of methanol was hydrogenated in the presence of 2 teaspoonsful of Raney nickel for 1½ hours at atmospheric pressure. The catalyst was removed by fltration and the filtrate was evaporated, and the end azeotropically with toluene. The residue was dissolved in 20 ml. of ethanol. Triethylorthoacetate, 3 ml., and 0.2 ml. of ethanolic hydrogen chloride (10%) was added and the mixture was heated to reflux for 15 minutes, and then evaporated to dryness. The residue was partitioned between methylene chloride and saturated aqueous bicarbonate solution. The organic layer was separated, drid over sodium sulfate and evaporated. Crystallizatin of the residue from methylene chloride/ether yielded crystals with m.p. 225°–227°. The analytic sample was recrystallized from 2-propanol and ethyl acetate, m.p. 228°–230°.

EXAMPLE 142

5-(2-Fluorophenyl)-2-[bis(morpholino)phosphinyloxy]-7-nitro-3H-1,4-benzodiazepine A stirred solution of 29.9 g. (0.1 m) of 1,3-dihydro-5-(2-fluorophenyl)-7-nitro-2H-1,4-benzodiazepin-2-one in 500 ml. of dry tetrahydrofuran was treated under argon portionwise with 5.5 g. (0.125 m) of a 54% mineral oil dispersion of sodium hydride and stirring was continued for 1 hour longer. Dimorpholinophosphinic chloride (38 g., 0.15 m) was added to the dark solution in one portion and stirring under argon was continued for 8 hours. The resultant dark mixture was filtered over filter aid and concentrated in vacuo at 50° to give a dark gum. When the dark gum was stirred at room temperature in 75 ml. of ethyl acetate, crystallization occurred to give a paste. After cooling in an ice bath for 30 minutes the mixture was filtered and the light tan solid was washed 3 times with 35 ml. portions of 2:1 ether/ethyl acetate and finally with ether. Air drying on the funnel yielded nearly pure product. Recrystallization from 15 fold amount of ethyl acetate gave off-white needles, m.p. 169°–172°.

EXAMPLE 143

7-Bromo-2-[bis(morpholino)phosphinyloxy]-5-(2-pyridyl)-3H-1,4-benzodiazepine Fifty-four percent sodium hydride in mineral oil dispersion (11 g., 0.25 m) was added in portions to a stirred solution of 63.2 g. (0.2 m) of 7-bromo-1,3-dihydro-5-(2-pyridyl)-2H-1,4-benzodiazepin-2-one in 1 l. of tetrahydrofuran under argon. After refluxing on a steam bath for 1 hour, the solution was cooled to room temperature and treated with 76.2 g. (0.3 m) of dimorpholinophosphinic chloride portionwise. Stirring at room temperature was continued for 5 hours. The dark mixture was filtered through Celite. Concentration of the filtrate in vacuo and boiling the dark residue with ether gave tan crystals. A sample was recrystallized by dissolving it in 2 ml. of methylene chloride, filtering, diluting with 10 ml. of ethyl acetate and cooling in an ice bath to give light tan plates. m.p. 180°–182° (dec.).

EXAMPLE 144

Acetylamino[7-chloro-5-(2-fluorophenyl)-3H-1,4-benzodiazepin-2-yl]malonic acid, diethyl ester A stirred suspension of 7.8 g. (0.174 m) of a 54% mineral oil dispersion of sodium hydride in 480 ml. of dimethylformamide was treated portionwise under argon with 30 g. (0.18 m) of diethyl acetamidomalonate. When the reaction had abated (ca. 30 minutes), 48 g. (0.096 m) of 7-chloro-5-(2-fluorophenyl)-2-[bis(morpholino)phosphinyloxy]-3H-1,4-benzodiazepine was added in one portion. Stirring was continued at room temperature for 5 hours, under argon. The dark mixture was poured, with stirring, into a mixture of ice and glacial acetic acid to give a light tan solid which was filtered, washed with water and partially air dried on the funnel. The damp solid was dissolved in methylene chloride. After separating the water layer the solution was dried over sodium sulfate, filtered and evaporated under reduced pressure to give a tan foam. The foam was dissolved in isopropanol (4 ml/g.) with stirring and kept at room temperature for 1 hour with occasional scratching to give off-white crystals. An equal volume of petroleum ether (30°–60°) was added and the mixture was kept at room temperature an additional 30 minutes before filtration. Washing with petroleum ether and air drying on the funnel yielded product, m.p. 150°–180°. Recrystallization of a sample from ethanol (10 ml/g.) raised the melting point to 185°–195° with previous softening.

EXAMPLE 145

Acetylamino[7-chloro-5-(2-chlorophenyl)-3H-1,4-benzodiazepin-2-yl]malonic acid, diethyl ester A stirred suspension of 4 g. (0.09 m) of a 54% mineral oil dispersion of sodium hydride in 315 ml. of dimethylformamide under argon was treafed with 21 g. (0.096 m) diethyl acetamidomalonate in several portions. Stirring at room temperature was continued for 30 minutes and then 31.4 g. (0.06 m) of 7-chloro-5-(2-chlorophenyl)-2-[bis(morpholino)phosphinyloxy]-3H-1,4-benzodiazepine was added in one portion. After stirring an additional 7 hours at room temperature the dark mixture was poured over ice and acetic acid with stirring and diluted with water (ca. 2 l.) to give a cream colored solid. The solid was filtered, washed with water and air dried on the funnel to give product. The dried solid was stirred with a small amount of 2-propanol while warming on a steam bath until solution occurred. Cooling to room temperature gave an off-white solid. Recrystallization of a sample from 8-fold amount of ethanol gave off-white microneedles, m.p. 153°–155°.

EXAMPLE 146

Acetylamino [7-bromo-5-(2-pyridyl)-3H-1,4-benzodiazepin-2-yl]malonic acid, diethyl ester A stirred suspension of 54% sodium hydride in mineral oil dispersion (3.35 g., 0.075 m) in 267 ml. of dimethylformamide was treated under argon with 17.5 g. (0.08 m) of diethyl acetamidomalonate in several portions. The mixture was stirred at room temperature 30 minutes longer and then treated with 26.7 g. (0.05 m) of 7-bromo-2-[bis(morpholino)phosphinyloxy]-5-(2-pyridyl)-3H-1,4-benzodiazepine in one portion. Stirring under argon at room temperature was continued for 7 hours. The dark mixture was poured over ice-acetic acid and diluted with water to give a greenish yellow solid. The solid was filtered, washed with water and air dried on the funnel to yield product. About 7 g of the solid was chromatographed over silica gel and eluted with ethyl acetate to give amorphous solid which showed one spot on tlc (ethyl acetate); Rf 0.5. When stirred with a small amount of isopropanol, the solid crystallized. Recrystallation of a sample from isopropanol gave light tan plates, m.p. 178°–180°.

EXAMPLE 147

2-[(Acetylamino)ethoxycarbonylmethylene]-7-chloro-1,3-dihydro-5-(2-fluorophenyl)-2H-1,4-benzodiazepine maleate A stirred solution of sodium ethoxide (prepared from 0.2 g., 0.01 g. atm. of sodium metal in 25 ml. of absolute ethanol) was treated with 2.4 g. (0.005 m) of acetylamino [7-chloro-5-(2-fluorophenyl)-3H-1,4-benzodiazepin-2-yl]malonic acid, diethyl ester, protected by a drying tube and stirred 5 hours longer at room temperature. The precipitated yellow solid was collected by filtration, washed successively with ethanol and ether and air dried to give product. The solid was partitioned between water and methylene chloride, acidified with acetic acid and extracted again with methylene chloride. After washing with dilute ammonium hydroxide solution the methylene chloride extract was dried over sodium sulfate and evaporated in vacuo to give a tan foam. A solution of 1. g. (0.0024 m) of the base in 25 ml. of ether was mixed with a solution of 0.56 g. (0.0048 m) of maleic acid in 25 ml. of ether and kept at room temperature. Orange crystals were obtained after several minutes with occasional scratching. The crystals were collected by filtration, washed with ether and air dried to yield product, m.p. ca. 150°. Recrystallization from 30 ml. of ethyl acetate after concentrating to ½ volume and seeding gave orange prisms, m.p. 149°–151°.

EXAMPLE 148

2-[(Acetylamino)ethoxycarbonylmethylene]-7-chloro-5-(2-chlorophenyl)-1,3-dihydro-2H-1,4-benzodiazepine maleate A solution of sodium ethylate was prepared by dissolving 0.8 g. (0.04 g. atm.) of sodium metal in 50 ml. of absolute ethanol and protected by a drying tube. Acetylamino[7-chloro-5-(2-chlorophenyl)-3H-1,4-benzodiazepin-2-yl]malonic acid, diethyl ester (10.1 g., 0.02 m) was added in one portion to the stirred solution and stirring in a dry atmosphere was continued at room temperature for 5 hours. The resulting mixture was acidified with acetic acid and concentrated in vacuo. The residue was partitioned between dilute ammonium hydroxide and methylene chloride. After separating the layers, the organic layer was dried over sodium sulfate and evaporated at reduced pressure to give a tan, amorphous solid. The solid was dissolved in 75 ml. of anhydrous ether and added to a warm solution of 4 g. of maleic acid in 200 ml. of ether. After decanting from a small amount of brown gum, the solution was concentrated on a steam bath to about 100 ml. Cooling at room temperature with occasional scratching gave crystallization after about 30 minutes. When crystallization was complete, the orange crystals were filtered, washed with ether and air dried on the funnel to give product. Recrystallization of a small sample from ethyl acetate (5 ml/g) gave yellow microneedles, m.p. 139°–142° (dec.).

EXAMPLE 149

Ethyl 6-(2-fluorophenyl)-1-methyl-8-nitro-4H-imidazo[1,5-a][1,4]benzodiazepine 3-carboxylate A stirred suspension of 0.85 g. (0.018 m) of a 54% mineral oil dispersion of sodium hydride in 55 ml. of dry dimethylformamide was treated with 3.5 g. (0.016 m) of diethyl acetamidomalonate in several portions under argon. After stirring for 30 minutes, 5.2 g. (0.01 m) of 5-(2-fluorophenyl)-2-[bis(morpholino) phosphinyloxy]-7-nitro-3H-1,4-benzodiazepine was added in one portion and stirring under argon was continued for 7 hours longer. The dark mixture was poured into a stirred mixture of ice and acetic acid and diluted with water to give a brownish yellow solid. The solid was washed with water and air dried on the funnel to give product. Tlc (ethyl acetate) showed 3 yellow spots with Rf 0.8, 0.5 and 0.25. Chromatography over silica gel using ethyl acetate as eluent gave the desired product with Rf of 0.25 as a brownish yellow solid. Recrystallization of the sample from ethyl acetate (5 ml/g) by dissolving in hot ethyl acetate and cooling in an ice bath gave yellow prisms, m.p. 231°–233°.

EXAMPLE 150

Ethyl 8-chloro-5-(2-fluorophenyl)-1-methyl-4H-imidazo[1,5-a][1,4]benzodiazepine 3-carboxylate Crude 2-[(acetylamino)ethoxycarbonylmethylene]-7-chloro-1,3-dihydro-5-(2-fluorophenyl)-2H-1,4-benzodiazepine (6.3 g., 0.015 m) which was prepared from the maleate by basifying with ammonia, extracting with methylene chloride and evaporating in vacuo, was dissolved in 35 ml. of hexamethylphosphoramide (HMPA) and heated, with stirring at 200°–210° for 5 minutes. The dark solution was cooled and poured into ice water to give a tan solid. The solid was filtered, washed with water and partially air dried on the funnel. The damp solid was dissolved in methylene chloride, dried over sodium sulfate and evaporated at reduced pressure to give product as tan foam. Recrystallization of 1 g. of the foam from 5 ml. of ethyl acetate and 5 ml. of petroleum ether (30°–60° C.) gave the product as light tan prisms, which melted at 176°–179°, slowly resolidified and melted again at 195°–198°.

EXAMPLE 151

Ethyl
8-chloro-6-(2-chlorophenyl)-1-methyl-4H-imidazo[1,5-a][1,4]benzodiazepine-3-carboxylate A solution of 3.2 g. (0.0073 m) of 2-[(acetylamino)ethoxycarbonylmethylene]-7-chloro-5-(2-chlorophenyl)-1,3-dihydro-2H-1,4-benzodiazepine in 15 ml. of hexamethylphosphoramide was stirred under nitrogen and heated at 200°–210° for 10 minutes. After cooling to room temperature the solution was poured into ice water and diluted with more water until precipitation was complete. The tan solid was filtered, washed with water and air dried on the funnel to give product. When stirred with ethyl acetate (2 ml/g) the solid dissolved and immediately rercrystallized. The tan solid was filtered, washed with 1:1 ethyl acetate-petroleum ether and air dried to give the above named product. Recrystallization of a sample from methylene chloride-ethyl acetate solution by removal of the methylene chloride by boiling gave off-white needles, m.p. 214°–215°.

EXAMPLE 152

Ethyl
8-bromo-1-methyl-6-(2-pyridyl)-4H-imidazo[1,5-a][1,4]benzodiazepine 3-carboxylate Diethyl acetamidomalonate, 43 g. (0.2 m) was added to a suspension of 10 g. (0.2 m) of a dispersion (50%) of sodium hydride in mineral oil in 500 ml. of dry dimethylformamide. This mixture was stirred under argon for 1 hour at room temperature and for 20 minutes with heating on the steam bath. 7-Bromo-2[bis(morpholino)-phosphinyloxy]-5-(2-pyridyl)-3H-1,4-benzodiazepine, 53.4 g. (0.1 m) was then added to the reaction mixture brought back to room temperature. After stirring for 1 hour at room temperature, it was again heated on the steam bath for 2 hours. The cooled solution was partitioned between water and methylene chloride/ether. The organic phase was separated, washed with water, dried and evaporated. The residue was crystallized with seeding from ethyl acetate/ether to give product as off-white crystals with m.p. 240°–243°. Seeds were obtained by chromatographic purification over 30 fold amount of silica gel using 5% (v/v) methanol in ethyl acetate. The analytical sample was recrystallized from ethyl acetate, m.p. 243°–244°.

EXAMPLE 153

Ethyl
6-(2-chlorophenyl)-1-methyl-8-nitro-4H-imidazo[1,5-a][1,4]benzodiazepine-3-carboxylate Diethyl acetamidomalonate, 43 g. (0.2 m) was added to a suspension of 10 g. (0.2 m) of sodium hydride (50% in mineral oil) in 500 ml. of dry dimethylformamide. The mixture was heated to 50° for 30 minutes under argon. After addition of 53 g. (0.1 m) of 5-(2-chlorophenyl)-2-[bis(morpholino)phosphinyloxy]-7-nitro-3H-1,4-benzodiazepine, the reaction mixture was heated on the steambath for 1 hour. The cooled brown mixture was partitioned between water and methylene chloride/ether. The organic phase was washed with water, dried and evaporated. The residue was chromatographed over 1 kg. of silica gel using ethyl acetate. The clean fractions of product were combined and evaporated. Crystallization of the residue from methylene chloride/ether yielded product as light yellow crystals with m.p. 233°–234°. The analytical sample was recrystallized from ethyl acetate, m.p. 234°–235°.

EXAMPLE 154

Ethyl
1-methyl-8-nitro-6-phenyl-4H-imidazo[1,5-a][1,4]benzodiazepine-3-carboxylate Sodium hydride dispersion (50% in mineral oil), 6 g. (0.125 m), was added to a solution of 28.1 g. (0.1 m) of 1,3-dihydro-7-nitro-5-phenyl-2H-1,4-benzo-diazepin-2-one in 300 ml. of dry tetrahydrofuran. After stirring for 1 hour at room temperature 30.2 g. (0.12 m) of dimorpholinophosphinic chloride was added and stirring was continued for 4 hours. The product was crystallized by addition of water and ether. The precipitate was collected and dissolved in methylene chloride. The solution was dried and evaporated and the residue was crystallized from ethyl acetate to yield crude 7-nitro-2-[bis(morpholino)phosphinyloxy]-5-phenyl-3H-1,4-benzodiazepine with m.p. 208°–209°.

Part of this material was added to a mixture of 8.6 g. (0.04 m) of diethyl acetaminomalonate, 2 g. (0.04 m) of sodium hydride suspension (50% in mineral oil) and 75 ml. of dimethylformamide which had been heated at 40° for 30 minutes. After addition the reaction mixture was heated for 30 minutes on the steambath and was then partitioned between water and ether. The organic phase was washed with water, dried and evaporated. The residue was chromatographed over 250 g. of silica gel using ethyl acetate. The combined clean fractions of product were evaporated and the residue was crystallized from methylene chloride/ether to yield product as off-white crystals with m.p. 240°–241°. The analytical sample was recrystallized from ethyl acetate.

EXAMPLE 155

1-Methyl-8-nitro-6-phenyl-4H-imidazo[1,5-a][1,4]benzodiazepine-3-carboxylic acid A mixture of 1.95 g. (5 mmol) of ethyl 1-methyl-8-nitro-6-phenyl-4H-imidazo[1,5-a][1,4]benzodiazepine-3-carboxylate, 50 ml. of methanol, 0.56 g. (0.01 m) of potassium hydroxide and 2 ml. of water was heated to reflux under nitrogen for 3 hours. After partial evaporation of the solvent the residue was acidified with 2 ml. of glacial acetic acid and was partitioned between methylene chloride containing 10% (v/v) of ethanol and water. The organic phase was dried and evaporated. Crystallization of the residue from ethyl acetate/methanol yielded product as straw colored crystals which were recrystallized from the same solvents for analysis, m.p. 240°–243° dec.

EXAMPLE 156

6-(2-Chlorophenyl)-1-methyl-8-nitro-4H-imidazo[1,5-a][1,4]benzodiazepine 3-carboxylic acid A mixture of 4.25 g. (0.01 m) of ethyl 6-(2-chlorophenyl)-1-methyl-8-nitro-4H-imidazo[1,5-a][1,4]benzodiazepine-3-carboxylate, 100 ml. of methanol, 1.12 g. (0.02 m) of potassium hydroxide and 4 ml. of water was heated to reflux under nitrogen for 3 hours. The bulk of the methanol was evaporated and the residue was partitioned between water and ether. The aqueous phase was washed with ether, acidified with acetic acid and extracted with methylene chloride. The extracts were dried and evaporated. Crystallization of the residue from methylene chloride/ethyl acetate yielded yellow

EXAMPLE 157

8-Bromo-1-methyl-6-(2-pyridyl)-4H-imidazo[1,5-a][1,4]benzodiazepine-3-carboxylic acid A mixture of 2.15 g. (5 mmol) of ethyl 8-bromo-1-methyl-6-(2-pyridyl)-4H-imidazo[1,5-a][1,4]benzodiazepine-3-carboxylate, 50 ml. of methanol, 0.84 g. (15 mmol) of potassium hydroxide and 2.5 ml. of water was heated to reflux for 5 hours. The bulk of the methanol was evaporated and the residue was partitioned between water and ether. The aqueous phase was acidified with acetic acid and extracted with methylene chloride. The extracts were dried and evaporated. Crystallization of the residue from methylene chloride/ethyl acetate gave product as colorless crystals which were recrystallized from methanol for analysis, m.p. 245°–250° dec. with previous sintering.

EXAMPLE 158

1-Methyl-8-nitro-6-phenyl-4H-imidazo[1,5-a][1,4]benzodiazepine maleate, hemi-ethyl acetate A suspension of 1.2 g. of 1-methyl-8-nitro-6-phenyl-4H-imidazo[1,5-a][1,4]benzodiazepine-3-carboxylic acid in 15 ml. of hexamethyl phosphoric acid triamide was heated to reflux for 3 minutes. The cooled solution was partitioned between methylene chloride/ether and aqueous sodium bicarbonate solution. The organic phase was washed with bicarbonate solution, dried and evaporated. The residue was chromatographed over 30 g. of silica gel using 3% (v/v) of ethanol in methylene chloride. Crystallization of the clean fractions from ether/methylene chloride/ethyl acetate yielded 1-methyl-8-nitro-6-phenyl-4H-imidazo[1,5-a][1,4]benzodiazepine with m.p. 168°–170°. It was converted to the maleate salt which crystallized from ethyl acetate with 0.5 m of solvent, m.p. 125°–128° dec.

EXAMPLE 159

6-(2-Chlorophenyl)-1-methyl-8-nitro-4H-imidazo[1,5-a][1,4]benzodiazepine maleate A mixture of 1.5 g. of 6-(2-chlorophenyl)-1-methyl-8-nitro-4H-imidazo[1,5-a][1,4]benzodiazepine-3-carboxylic acid and 10 ml. of ethylene glycol was heated to reflux for 1 hour. The reaction mixture was then partitioned between methylene chloride/toluene and saturated aqueous sodium bicarbonate solution. The organic phase was washed with water, dried and evaporated. The residue was dissolved in 10 ml. of 2-propanol and treated with 0.6 g. of maleic acid. The salt crystallized upon addition of ether to the warm solution. It was collected, washed with 2-propanol and ether to yield product as tan crystals which were recrystallized from 2-propanol for analysis, m.p. 150°–152°. The free base liberated from this salt was crystallized from ethyl acetate/hexane, m.p. 170°–173°.

EXAMPLE 160

8-Bromo-1-methyl-6-(2-pyridyl)-4H-imidazo[1,5-a][1,4]benzodiazepine

A solution of 1.3 g. of 8-bromo-1-methyl-6-(2-pyridyl)-4H-imidazo[1,5-a][1,4]benzodiazepine-3-carboxylic acid in 20 ml. of ethylene glycol was heated to reflux for 1 hour. The reaction mixture was partitioned between water and methylene chloride/toluene. The organic phase was washed with saturated sodium bicarbonate solution, dried and evaporated. Crystallization of the residue from ether/2-propanol gave product as tan crystals. The analytical sample was recrystallized from ethyl acetate/hexane, m.p. 189°–190°.

EXAMPLE 161

8-Chloro-6-(2-chlorophenyl)-3-hydroxymethyl-1-methyl-4H-imidazo[1,5-a][1,4]benzodiazepine A solution of 1.2 g. (3 mmol) of methyl 8-chloro-6-(2-chlorophenyl)-1-methyl-4H-imidazo[1,5-a][1,4]benzodiazepine-3-carboxylate in 10 ml. of tetrahydrofuran was added to a suspension of 0.4 g. (10 mmol) of lithium aluminum hydride in 30 ml. of ether cooled to 10°. Following the addition, the mixture was stirred at room temperature for 10 minutes and hydrolyzed by addition of 2 ml. of water. The inorganic material was filtered off and the filtrate was evaporated. Crystallization of the residue from methylene chloride/ether yielded product with m.p. 215°–217°. The analytical sample was recrystallized from tetrahydrofuran/hexane, m.p. 217°–128°.

EXAMPLE 162

8-Chloro-N,N-diethyl-6-(2-fluorophenyl)-1-methyl-4H-imidazo[1,5-a][1,4]benzodiazepine-3-carboxamide Phosphorus pentachloride, 1.25 g. (0.006 m) was added to a suspension of 1.85 g. (0.005 m) of 8-chloro-6-(2-fluorophenyl)-1-methyl-4H-imidazo[1,5-a][1,4]benzodiazepine-3-carboxylic acid in 250 ml. of methylene chloride. After stirring for 30 minutes in an ice bath, 15 ml. of diethylamine was added followed by 100 ml. of 10% aqueous sodium carbonate solution. The two phase system was stirred for 30 minutes at room temperature. The organic layer was separated, dried over sodium sulfate and evaporated. Crystallization of the residue from methylene chloride/ether yielded product with m.p. 182°–188°. The analytical sample was recrystallized from ethyl acetate/hexane, m.p. 183°–185°.

EXAMPLE 163

8-Chloro-N-(2-dimethylaminoethyl)-6-(2-fluorophenyl)-1-methyl-4H-imidazo[1,5-a][1,4]benzodiazepine-3-carboxamide 2-(Dimethylamino)ethylamine, 5 ml., was added to a solution of acid chloride prepared as described above from 1.85 g. (5 mmol) of 8-chloro-6-(2-fluorophenyl)-1-methyl-4H-imidazo[1,5-][1,4]benzodiazepine-3-carboxylic acid and 1.25 g. of phosphorus pentachloride in 250 ml. of methylene chloride. Following the addition of 100 ml. of 10% aqueous sodium carbonate solution, the mixture was stirred for 30 minutes at room temperature. The methylene chloride layer was separated, dried and evaporated. Crystallization of the residue from 2-propanol/ether yielded product with m.p. 209°–211°. The analytical sample was recrystallized from ethyl acetate/hexane, m.p. 210°–213°.

EXAMPLE 164

8-Chloro-6-(2-fluorophenyl)-1-methyl-4H-imidazo[1,5-a][1,4]benzodiazepine-3-carboxamide Methanolic ammonia, 20 ml., 25%, was added to a solution of acid chloride prepared as described in the previous example from 1.85 g. of 8-chloro-6-(2-fluorophenyl)-1-methyl-4H-imidazo[1,5-a][1,4]benzodiazepine-3-carboxylic acid and 1.25 g. of phosphorus pentachloride in 250 ml. of methylene chloride. After stirring for 10 minutes, 50 ml. of 10% aqueous sodium carbonate solution was added and stirring was continued for 1 hour at room temperature. The methylene chloride layer was separated, dried and evaporated. The residue was dissolved in a mixture of methylene chloride and ethanol. The solution was filtered over a bed of silica gel and the filtrate was evaporated. Crystallization of the residue from ethanol gave the product as colorless crystals. The analytical sample was recrystallized from ethanol/tetrahydrofuran, m.p. 300°–305°.

EXAMPLE 165

8-Chloro-6-(2-fluorophenyl)-1,N,N-trimethyl-4H-imidazo[1,5-a][1,4]benzodiazepine-3-carboxamide Dimethylamine, 4 ml. was added to a solution of the acid chloride prepared as in the previous example from 1.85 g. (0.005 m) of 8-chloro-6-(2-fluorophenyl)-1-methyl-4H-imidazo[1,5-a][1,4]benzodiazepine-3-carboxylic acid, and 1.25 g. (0.006 m) of phosphorus pentachloride in 250 ml. of methylene chloride. After stirring at room temperature for 1 hour, the reaction mixture was washed with 10% aqueous sodium carbonate solution, was dried and evaporated. The residue was purified by chromatography over 40 g. of silica gel using 5% (v/v) of ethanol in methylene cloride. Crystallization of the combined clean fractions from ether/hexane yielded product as colorless crystals, m.p. 177°–179°. A lower melting modification with m.p. 158°–160° was also observed.

EXAMPLE 166

1-[8-Chloro-6-(2-fluorophenyl)-1-methyl-4H-imidazo[1,5-a][1,4]benzodiazepin-3-oyl]pyrrolidine Pyrrolidine, 4 ml., was added to a solution of acid chloride prepared as described above from 1.85 g. of 8-chloro-6-(2-fluorophenyl)-1-methyl-4H-imidazo[1,5-a][1,4]benzodiazepine-3-carboxylic acid and 1.25 g. of phosphorus pentachloride in 250 ml. of methylene chloride. Subsequently 100 ml. of 10% aqueous sodium carbonate solution was added and the two phase mixture was stirred at room temperature for 1 hour. The organic phase was separated, dried and evaporated. Crystallization of the residue from 2-propanol/ether gave colorless product with m.p. 220°–221° after recrystallization from ethyl acetate/hexane.

EXAMPLE 167

8-Chloro-6-(2-fluorophenyl-1-methyl-4H-imidazo[1,5-a][1,4]benzodiazepine-3-carboxylic acid, 2,2-dimethylhydrazide 2,2-Dimethylhydrazine, 10 ml., was added to a solution of acid chloride prepared as described above from 1.85 g. of 8-chloro-6-(2-fluorophenyl)-1-methyl-4H-imidazo[1,5-a][1,4]benzodiazepine-3-carboxylic acid and 1.25 g. of phosphorus pentachloride in 250 ml. of methylene chloride. After addition of 100 ml. of 10% aqueous sodium carbonate solution the mixture was stirred for 30 minutes at room temperature. The organic layer was separated, dried and evaporated. Crystallization of the residue from ether/ethanol yielded colorless product. The analytical sample was purified by chromatography over 30 fold amount of silica gel, using 10% (v/v) of ethanol in methylene chloride. It was crystallized from methylene chloride/ethyl acetate/hexane, m.p. 238°–240°.

EXAMPLE 168

8-Chloro-6-(2-fluorophenyl)-3-(methyoxycarbonylamino)-1-methyl-4H-imidazo[1,5-a][1,4]benzodiazepine A mixture of 1.85 g. (5 mmol) of 8-chloro-6-(2-fluorophenyl)-1-methyl-4H-imidazo[1,5-a][1,4]benzodiazepine-3-carboxylic acid, 1.5 g. of diphenylphosphoric azide, 30 ml. of dimethylformamide and 2 ml. of triethylamine was stirred at room temperature for 15 minutes. 6 Ml. of methanol was added and the reaction mixture was heated to reflux for 30 minutes. The solvent was removed under reduced pressure, at the end azeotropically with xylene. Crystallization of the residue from ethyl acetate yielded product which was recrystallized from methylene chloride/methanol/ethyl acetate, m.p. 270°–275°. The analytical sample was recrystallized from tetrahydrofuran/ethanol, m.p. 272°–275° dec.

EXAMPLE 169

3-(Benzyloxycarbonylamino)-8-chloro-6-(2-fluorophenyl)-1-methyl-4H-imidazo[1,5-a][1,4]benzodiazepine A mixture of 1.85 g. (5 mmol) of 8-chloro-6-(2-fluorophenyl)-1-methyl-4H-imidazo[1,5-a][1,4]benzodiazepine-3-carboxylic acid, 1.5 g. of diphenylphosphoric azide, 10 ml. of dimethylformamide, 25 ml. of toluene and 2 ml. of triethylamine was stirred at room temperature for 10 minutes. Benzyl alcohol, 10 ml., was added and the mixture was heated to reflux for 30 minutes. After evaporation of the solvents under reduced pressure, the residue was crystallized from ether to yield product with m.p. 250°–253°. The analytical sample was recrystallized from methylene chloride/methanol/ethyl acetate, m.p. 253°–255°.

EXAMPLE 170

8-Chloro-3-methoxycarbonylamino-1-methyl-5-nitroso-6-phenyl-5,6-dihydro-4H-imidazo[1,5-][1,4]benzodiazepine Sodium nitrite, 1.8 g. (2.5 mmol), was added in portions over a 5 minute period to a solution of 3.7 g. (10 mmol) of 8-chloro-5,6-dihydro-1-methyl-6-phenyl-4H-imidazo[1,5-a][1,4]benzodiazepine-3-carboxylic acid hydrazide in 35 ml. of glacial acetic acid. After stirring for 30 minutes at room temperature, the azide was precipitated by addition of ice and water. The solids were collected and dissolved in methylene chloride. The solution was washed with water, sodium bicarbonate solution and ice, was dried and evaporated. The residue was dissolved in a mixture of 100 ml. of dimethylformamide and 25 ml. of methanol and heated to reflux for 20 minutes (temperature ca 103°). The solvents were removed under reduced pressure and the residue was crystallized from methanol/ethyl acetate to yield colorless crystals with m.p. 255°–258° dec. The analytical sample was recrystallized from tetrahydrofuran/ethanol and had the same melting point.

EXAMPLE 171

8-Chloro-5,6-dihydro-3-(methoxycarbonylamino)-1-methyl-6-phenyl-4H-imidazo[1,5-a][1,4]benzodiazepine 8-Chloro-3-methoxycarbonylamino-1-methyl-5-nitroso-6-phenyl-5,6-dihydro-4H-imidazo[1,5-a][1,4]benzodiazepine, 2.06 g. (5 mmol) was dissolved by warming in a mixture of 200 ml. of tetrahydrofuran and 100 ml. of methanol. After addition of Raney nickel (2 teaspoonsful) the mixture was hydrogenated at atmospheric pressure for 1 hour. The catalyst was separated by filtration and the filtrate was evaporated. Crystallization of the residue from methanol yielded colorless crystals with m.p. 280°–290° dec. The analytical sample was recrystallized from ethyl acetate/methanol.

EXAMPLE 172

8-Chloro-6-(2-fluorophenyl)-1-methyl-4H-imidazo[1,5-a][1,4]benzodiazepine 5-oxide A mixture of 9.75 g. (0.03 m) of 8-chloro-6-(2-fluorophenyl)-1-methyl-4H-imidazo[1,5-a][1,4]benzodiazepine, 200 ml. of methylene chloride and 12 g. (0.07 m) of m-chloroperbenzoic acid was stirred for 1½ hours. The solution was then extracted with 3×150 ml. of 1 N hydrochloric acid. The extracts were washed with ether, made alkaline with ammonia and extracted with methylene chloride. The methylene chloride extracts were dried and evaporated and the residue was crystallized from ethyl acetate to leave product which was further purified by chromatography over 100 g. of silica gel using 5% (v/v) of ethanol in methylene chloride. The clean fractions were combined and evaporated. Crystallization of the residue from ethyl acetate/ether yielded colorless crystals with m.p. 245°–246° dec.

EXAMPLE 173

4-Acetoxy-8-chloro-6-(2-fluorophenyl)-1-methyl-4H-imidazo[1,5-a][1,4]benzodiazepine A solution of 4 g. of 8-chloro-6-(2-fluorophenyl)-1-methyl-4H-imidazo[1,5-a][1,4]benzodiazepine 5-oxide in 100 ml. of acetic anhydride was heated on the steam bath for 24 hours. The reagent was evaporated under reduced pressure, at the end azeotropically with xylene. The residue was chromatographed over 80 g. of silica gel using 20% (v/v) methylene chloride in ethyl acetate. Crystallization of the clean fractions from methylene chloride/ether yielded colorless crystals, m.p. 201°–202°.

EXAMPLE 174

8-Chloro-6-(2-fluorophenyl)-4-hydroxy-1-methyl-4H-imidazo[1,5-a][1,4]benzodiazepine 4-Acetoxy-8-chloro-6-(2-fluorophenyl)-1-methyl-4H-imidazo[1,5-a][1,4]benzodiazepine, 0.5 g. (1.3 mmol) was added to 40 ml. of methanol containing 4 mmol of sodium methoxide. After stirring under nitrogen for ½ hour at room temperature, the solvent was evaporated under reduced pressure. The residue was dissolved in water and the solution was acidified with acetic acid. The precipitated crystals were collected and dissolved in methylene chloride. The solution was dried and evaporated and the residue was crystallized from methylene chloride/ether to yield colorless crystals with m.p. 185°–186°.

EXAMPLE 175

8-Chloro-6-(2-fluorophenyl)-1-methyl-4H-imidazo[1,5-a][1,4]benzodiazepine 2,5-dioxide A mixture of 9.75 g. (0.03 m) of 8-chloro-6-(2-fluorophenyl)-1-methyl-4H-imidazo[1,5-a][1,4]benzodiazepine, 18 g. (0.105 m) of m-chloroperbenzoic acid and 200 ml. of methylene chloride was stirred at room temperature overnight. After dilution with 500 ml. of ether, the reaction mixture was extracted 4 times with 75 ml. of 1N hydrochloric acid. The extracts were washed with ether, made alkaline with ammonia and extracted with methylene chloride. The extracts were dried and evaporated. Crystallization from ethyl acetate gave 8-chloro-6-(2-fluorophenyl)-1-methyl-4H-imidazo[1,5-a][1,4]benzodiazepine 5-oxide.

The aqueous phase was evaporated under reduced pressure to dryness. The residue was washed out well with methylene chloride containing 20% of ethanol. The combined washings were evaporated to leave crude 2,5-dioxide which was chromatographed over 40 g. of silica gel using 50% of methanol in methylene chloride. After elution of the less polar 8-chloro-6-(2-fluorophenyl)-1-methyl-4H-imidazo[1,5-a][1,4]benzodiazepine 2-oxide with m.p. 179°–181° dec. after recrystallization from ethyl acetate/methanol the pure fractions of the 2,5-dioxide were combined and evaporated. Crystallization from ethyl acetate yielded product as off-white crystals with m.p. 225°–230° dec. The analytical sample was recrystallized from methanol/ethyl acetate.

EXAMPLE 176

1-Acetoxymethyl-8-chloro-6-(2-fluorophenyl)-4H-imidazo[1,5-a][1,4]benzodiazepine 5-oxide A solution of 1 g. of 8-chloro-6-(2-fluorophenyl)-1-methyl-4H-imidazo[1,5-a][1,4]benzodiazepine 2,5-dioxide in 10 ml. of acetic anhydride was heated on the steambath for 15 minutes. The reagent was evaporated under reduced pressure and the residue was crystallized from ethyl acetate/ether to yield crystals with m.p. 203°–205°. For analysis it was recrystallized from ethyl acetate.

EXAMPLE 177

1-Acetoxymethyl-8-chloro-6-(2-fluorophenyl)-4H-imidazo[1,5-a][1,4]benzodiazepine A mixture of 1 g. of 1-acetoxymethyl-8-chloro-6-(2-fluorophenyl)-4H-imidazo[1,5-a][1,4]benzodiazepine 5-oxide, 30 ml. of methylene chloride and 3 ml. of phosphorus trichloride was allowed to sit at room temperature for 24 hours. After evaporation under reduced pressure the residue was partitioned between methylene chloride and saturated sodium bicarbonate solution. The organic phase was dried and evaporated. Crystallization of the residue from ethyl acetate/hexane gave colorless product with m.p. 151°–152°. For analysis it was recrystallized from ethyl acetate/ether.

EXAMPLE 178

8-Chloro-6-(2-fluorophenyl)-1-hydroxymethyl-4H-imidazo[1,5-a][1,4]benzodiazepine Sodium methoxide, 0.3 g., was added to a solution of 1 g. of 1-acetoxymethyl-8-chloro-6-(2-fluorophenyl)-4H-imidazo[1,5-a][1,4]benzodiazepine in 20 ml. of methanol. After standing for 10 minutes at room temperature, the separated crystals were collected, washed with aqueous methanol, methanol and ether to yield colorless product. The analytical sample was recrystallized from methylene chloride/ethanol, m.p. 258°–260°.

EXAMPLE 179

8-Chloro-6-(2-fluorophenyl)-4H-imidazo[1,5-a][1,4]benzoidazepine-1-carboxaldehyde A mixture of 0.2 g. of 8-chloro-6-(2-fluorophenyl)-1-hydroxymethyl-4H-imidazo[1,5-a][1,4]benzodiazepine, 20 ml. of methylene chloride and 1 g. of activated manganese dioxide was stirred at room temperature for 2 hours. The manganese dioxide was removed by filtration over celite and the filtrate was evaporated. Crystallization of the residue from methylene chloride/ethyl acetate/hexane gave product as colorless crystals with m.p. 182°–183°.

EXAMPLE 180

3-Bromo-8-chloro-6-(2-fluorophenyl)-1-methyl-4H-imidazo[1,5-a][1,4]benzodiazepine N-bromosuccinimide, 13.7 g (0.077 m) was added to a stirred solution of 8-chloro-6-(2-fluorophenyl)-1-methyl-4H-imidazo[1,5-a][1,4]benzodiazepine, 10 g. (0.030 m) in 450 ml. of chloroform and 30 ml. of glacial acetic acid. The mixture was stirred under reflux for 1.5 hours and then cooled. The mixture was then washed with saturated sodium bicarbonate solution and the chloroform layer dried and evaporated. The oily residue was chromatographed using 150 g. of Woelm neutral aluminum oxide. Impurities were removed first with methylene chloride, followed by ethyl acetate to remove the product. The fractions containing product were combined and evaporated. Crystallization of the residue with ether yielded product with m.p. 201°–205° C. The analytical sample was recrystallized from ether/hexane, m.p. 203°–205° C.

EXAMPLE 181

8-Chloro-3-cyano-1-methyl-6-phenyl-4H-imidazo[1,5-a][1,4]benzodiazepine

A mixture of 2.45 g. (0.07 m) of 8-chloro-1-methyl-6-phenyl-4H-imidazo[1,5-a][1,4]benzodiazepine-3-carboxamide, 50 ml. of pyridine and 7 g. of phosphorus pentoxide was heated to reflux for 15 minutes. The pyridine was evaporated under reduced pressure and the residue was partitioned between ice, 10% sodium carbonate solution and methylene chloride. The organic layer was separated, dried and evaporated. The residue was chromatographed over 50 g. of silica gel using ethyl acetate/methylene chloride 1:1. Crystallization from ethyl acetate/hexane yielded product with m.p. 228°–229°.

EXAMPLE 182

8-Chloro-6-(2-chlorophenyl)-1-methyl-4H-imidazo[1,5-a][1,4]benzodiazepine-3-carboxaldehyde Activated manganese dioxide, 5 g., was added to a solution of 1 g. of 8-chloro-6-(2-chlorophenyl)-3-hydroxymethyl-1-methyl-4H-imidazo[1,5-a][1,4]benzodiazepine in 50 ml. of methylene chloride. The mixture was stirred at room temperature for 2 hours. The manganese dioxide was filtered off and the filtrate was evaporated. Crystallization of the residue from ethanol gave product as colorless crystals with m.p. 237°–239°. The analytical sample was recrystallized from tetrahydrofuran/ethanol.

EXAMPLE 183

8-Chloro-6-(2-fluorophenyl)-1-methyl-4H-imidazo[1,5-a][1,4]benzodiazepine-3-carboxaldoxime A mixture of 1.4 g. (4 mmol) of 8-chloro-6-(2-fluorophenyl)-1-methyl-4H-imidazo[1,5-a][1,4]benzodiazepine-3-carboxaldehyde, 2 ml. of triethylamine, 30 ml. of ethanol and 0.56 g. (8 mmol) of hydroxylamine hydrochloride was allowed to stand at room temperature for 1½ hours. After dilution with water the precipitated crystals were collected and dried to yield oxime with m.p. 269°–271°. The analytical sample was recrystallized from tetrahydrofuran/ethanol, m.p. 272–275°.

EXAMPLE 184

2-[(Amino)methoxycarbonylmethylene]-7-chloro-5-(2-chlorophenyl)-1,3-dihydro-2H-1,4-benzodiazepine 7-Chloro-5-(2-chlorophenyl)-alpha-hydroxyimino-3H-1,4-benzodiazepine-2-acetic acid, methyl ester, 7.8 g. (0.02 m) was dissolved in a mixture of 200 ml. of tetrahydrofuran and 100 ml. of ethanol by warming. The solution was hydrogenated in the presence of Raney nickel (2 teaspoonsful) at atmospheric pressure for 2 hours. The catalyst was separated by filtration over Celite and the filtrate was evaporated under reduced pressure. Crystallization of the residue from ethanol gave product as orange crystals with m.p. 115°–117° dec. Recrystallization of this solvated product from ether/hexane gave yellow needles with m.p. 145°–150° dec.

EXAMPLE 185

Methyl 8-chloro-6-(2-chlorophenyl)-1-methyl-4H-imidazo[1,5-a][1,4]benzodiazepine-3-carboxylate Acetaldehyde, 0.25 ml., was added to a solution of 0.5 g. of 2-[(amino) methoxycarbonylmethylene]-7-chloro-5-(2-chlorophenyl)-1,3-dihydro-2H-1,4-benzodiazepine in 25 ml. of methylene chloride. Following the addition of molecular sieves 5A, the mixture was stirred at room temperature for 15 minutes. Activated manganese dioxide, 1g., was then added and stirring was continued for 30 minutes. The solid material was separated by filtration over celite and the filtrate ;was evaporated. Crystallization of the residue from ethyl acetate/hexane gave product with m.p. 228°–230°.

EXAMPLE 186

8-Chloro-6-(2-chlorophenyl)-1-methyl-4H-imidazo[1,5-a][1,4]benzodiazepine-3-carboxylic acid A stirred solution of 4.1 g. (0.01 m) of ethyl 8-chloro-6-(2-chlorophenyl)-1-methyl-4H-imidazo[1,5-a][1,4]benzodiazepine-3-carboxylate in 100 ml. of methanol containing 3 ml. of water and 1.2 g. (0.02 m) of potassium hydroxide was heated at reflux under nitrogen for 4.5 hours and concentrated at reduced pressure to remove the methanol. The residue was dissolved in cold water and acidified with acetic acid to give an off-white solid. After air drying on the funnel overnight, product was obtained. Recrystallization of a sample from 1:1 methylene chloride/ethanol gave white platelets, m.p. 265°–267° (dec.).

EXAMPLE 187

8-Chloro-6-(2-chlorophenyl)-1-methyl-4H-imidazo[1,5-a][1,4]benzodiazepine-3-carboxamide A stirred suspension of 1.2 g. (0.0031 m) of ethyl 8-chloro-6-(2-chlorophenyl)-1-methyl-4H-imidazo[1,5-a][1,4]benzodiazepine-3-carboxylate in 25 ml. of methylene chloride was cooled in an ice bath and tretaed with 0.7 g. (0.004 m) of phosphorus pentachloride in portions. The mixture was protected by a drying tube and stirring in the cold was continued 30 minutes longer during which time most of the solid dissolved. With continued cooling and stirring, the mixture was treated with gaseous ammonia for 5 minutes and stirred an additional 30 minutes in the cold. The mixture was evaporated in vacuo to give a light solid which was stirred with dilute aqueous ammonia and filtered through a coarse sintered glass funnel. After washing with water the solid was air dried on the funnel to give product. Recrystallization of a sample from 2:1 methylene chloride/ethanol solution gave white plates, m.p. 318°–320° (dec.).

EXAMPLE 188

5-Aminomethyl-1-[4-chloro-2-(2-fluorobenzoyl)-phenyl]-2-methylimidazole dihydrochloride A solution of 25 g. of 8-chloro-6-(2-fluorophenyl)-1-methyl-4H-imidazo[1,5-a][1,4]benzodiazepine in 50 ml. of water and 50 ml. of concentrated hydrochloric acid was allowed to stand at room temperature for 3 hours. Following addition of 250 ml. of 2-propanol the mixture was evaporated partially under reduced pressure without heating. Additional 200 ml. of 2-propanol were added and partial evaporation was resumed. The precipitated crystals were collected and washed well with 2-propanol and ether to yield product with m.p. 302°–307° (dec.). The analytical sample was recrystallized from methanol/2-propanol without heating.

EXAMPLE 189

3-Acetamino-8-chloro-6-(2-fluorophenyl)-1-methyl-4H-imidazo[1,5-a][1,4]benzodiazepine A solution of 0.2 g. of 3-(benzyloxycarbonylamino)-8-chloro-6-(2-fluorophenyl)-1-methyl-4H-imidazo[1,5-a][1,4]benzodiazepine in 10 ml. of glacial acetic acid and 2 ml. of acetic anhydride was hydrogenated over palladium on charcoal (10%) for 1 hour at atmospheric pressure. The catalyst was filtered off and the filtrate was evaporated, at the end azeotropically with xylene. The residue was chromatographed over 6 g. of silica gel using 10% ethanol in methylene chloride. Crystallization of the combined pure fractions from ethyl acetate/ether gave product as colorless crystals with m.p. 175°–178°.

EXAMPLE 190

Methyl 8-chloro-6-(2-fluorophenyl)-1-methyl-4H-imidazo[1,5-a][1,4]benzodiazepin-4-carboxylate Potassium t-butoxide, 0.25 g. (2.2 mmol) was added to a solution of 0.65 g. (2 mmol) of 8-chloro-6-(2-fluorophenyl)-1-methyl-4H-imidazo[1,5-a][1,4]benzodiazepine in 10 ml. of dimethylformamide cooled to −30°. After stirring under nitrogen for 10 minutes, 0.2 ml. of methyl chloroformate was added in one portion at −30°. When the reaction mixture had warmed to 0° it was partitioned between methylene chloride and saturated sodium bicarbonate solution. The methylene chloride layer was diluted with benzene and washed with bicarbonate solution and water, was dried and evaporated. The residue was chromatographed over 20 g. of silica gel using ethyl acetate. Crystallization of the combined clean fractions of product from ether yielded colorless crystals with m.p. 203°–205°. The analytical sample was recrystallized from ethyl acetate/hexane.

EXAMPLE 191

8-Chloro-6-(2-chlorophenyl)-1-methyl-4H-imidazo[1,5-a][1,4]benzodiazepine-3-carboxaldoxime Hydroxylamine hydrochloride, 0.14 g. (2 mmol) was added to a suspension of 0.37 g. (1 mmol) of 8-chloro-6-(2-chlorophenyl)-1-methyl-4H-imidazo[1,5-a][1,4]benzodiazepine-3-carboxaldehyde in 10 ml. of ethanol and 0.5 ml. of triethylamine. The mixture was heated on the steambath until solution was complete and the solution was allowed to stand for 2 hours. The separated crystals were collected, washed with water, ethanol and ether to yield oxime. The analytical sample was recrystallized from tetrahydrofuran/ethanol, m.p. 290°–292° dec.

EXAMPLE 192

8-Chloro-6-(2-chlorophenyl)-3-(1-hydroxyethyl)-1-methyl-4H-imidazo[1,5-a][1,4]benzodiazepine A solution of methyl magnesium iodide in ether, 5 ml., ca. 1-molar, was added to a solution of 0.37 g. (1 mmol) of 8-chloro-6-(2-chlorophenyl)-1-methyl-4H-imidazo[1,5-a][1,4]benzodiazepine-3-carboxaldehyde in 10 ml. of tetrahydrofuran. After sitting for 15 minutes at room temperature the mixture was decomposed with water. The inorganic material was filtered off and washed with methylene chloride. The filtrate was dried and evaporated. Crystallization of the residue from ether and recrystallization from ethyl acetate/hexane gave product as colorless crystals with m.p. 197°–199°.

EXAMPLE 193

3-Acetyl-8-chloro-6-(2-chlorophenyl)-1-methyl-4H-imidazo[1,5-a][1,4]benzodiazepine A solution of 0.1 g. of 8-chloro-6-(2-chlorophenyl)-3-(1-hydroxyethyl)-1-methyl-4H-imidazo[1,5-a][1,4]benzodiazepine in 20 ml. of methylene chloride was stirred at room temperature for 3 hours in the presence of 0.5 g. of activated manganese dioxide. The manganese dioxide was filtered off and the filtrate was evaporated. The crystalline residue was recrystallized from ethyl acetate/hexane to yield product as colorless crystals with m.p. 234°–236°.

EXAMPLE 194

2-Methylamino-5-phenyl-3H-thieno-[3,2-e][1,4]diazepine

A mixture of 10 g. (0.036 m) of 1,3-dihydro-5-phenyl-2H-thieno-[3,2-e][1,4]diazepine-2-one in 50 ml. of benzene and 300 ml. of tetrahydrofuran was stirred on an ice bath and saturated with methylamine gas. To this mixture was added dropwise a solution of titanium tetrachloride, 9.48 g. (0.05 m) in 50 ml. of benzene. After the addition was complete, the mixture was stirred on the ice bath for 15 minutes. The ice bath was then replaced with a heating mantel and the mixture refluxed for ½ hour. The mixture was cooled and 100 g. of ice carefully added. The mixture was filtered and the residue washed with tetrahydrofuran. The filtrates were combined, dried and evaporated. The product was crystallised from methylene chloride to yield product, m.p. 223°–227°. From the concentrated mother liquors was obtained additional product, m.p. 222°–225°. The analytical sample was recrystallized from methylene chloride, m.p. 227°–229°.

EXAMPLE 195

7-Chloro-5-phenyl-2-methylamino-3H-thieno-[2,3-e][1,4]diazepine

A mixture of 7.7 g. (0.0278 m) 7-chloro-1,3-dihydro-5-phenyl-2H-thieno[2,3-e][1,4]diazepin-2-one, 50 ml. of benzene and 250 ml. of tetrahydrofuran was stirred on an ice bath and saturated with methylamine gas. To this mixture was added a solution of titanium tetrachloride (7.38 g.), (0.0389 m) in 50 ml. of benzene from a dropping funnel. After the addition was complete, the mixture was stirred on the ice bath for 15 minutes. The ice bath was then replaced by a heating mantel and the reaction mixture was refluxed for 20 minutes. The mixture was cooled and 100 g. of ice were carefully added. The mixture was then filtered, and the residue washed with tetrahydrofuran. The filtrates were combined, dried and evaporated. The product was crystallised from methylene chloride/ether m.p. 246°–249°. The analytical sample was recrystallized from methylene chloride, m.p. 247°–250°.

EXAMPLE 196

7-Chloro-5-(2-chlorophenyl)-2-methylamino-3H-thieno[2,3-e][1,4]diazepine

A solution of 50 g. (0.161 m) of 7-chloro-5-(2-chlorophenyl)-1,3-dihydro-2H-thieno[2,3-e][1,4]diazepin-2-one, in 900 ml. of dry tetrahydrofuran and 300 ml. of dry benzene was cooled in an ice bath, and methylamine was bubbled in until the solution was saturated, a solution of 40 g. (0.209 m) of titanium tetrachloride in 100 ml. of benzene was added dropwise with stirring. After 4 hours at room temperature a few grams of ice were added and the reaction was filtered. The precipitate was washed several times with hot tetrahydrofuran, and the combined filtrates were evaporated. The residue was partitioned between 250 ml. of dichloromethane and 200 ml. of water and filtered. The dichloromethane solution was separated, dried and evaporated. This residue and the precipitate were recrystallized from a mixture of tetrahydrofuran and ethanol to give product. A sample was recrystallized for analysis from a mixture of tetrahydrofuran and hexane to give pale yellow prisms, m.p. 259°–262°.

EXAMPLE 197

2-(N-nitrosomethylamino)-5-phenyl-3H-thieno[3,2-e][1,4]diazepine

Nitrosyl chloride was introduced into a solution of 7.8 g. (0.03 m) of 2-methylamino-5-phenyl-3H-thieno[3,2-e][1,4]diazepine in 100 ml. of methylene chloride and 40 ml. of pyridine cooled in ice water. The reaction was monitored by thin layer chromatography and when the starting material had disappeared the nitrosyl chloride addition was terminated and the reaction mixture was partitioned between methylene chloride and water. The methylene chloride solution was dried and evaporated. Crystallization of the residue from methylene chloride/hexane yielded product as yellow crystals with m.p. 156°–159°. The analytical sample was recrystallized from ether/hexane, m.p. 158°–160°.

EXAMPLE 198

7-Chloro-2-(N-nitrosomethylamino)-5-phenyl-3H-thieno[2,3-e][1,4]diazepine

Nitrosyl chloride was introduced into a solution of 5.8 g. (0.02 m) of 7-chloro-5-phenyl-2-methylamino-3H-thieno[2,3-e][1,4]diazepine in 100 ml. of methylene chloride and 50 ml. of pyridine until the reaction was complete according to thin layer chromatogram. The mixture was partitioned between water and toluene. The organic phase was dried and evaporated. Crystallization of the residue from ether/hexane yielded product as yellow crystals with m.p. 108°–110°. For analysis it was recrystallized from ether/hexane, m.p. 111°–113°.

EXAMPLE 199

7-Chloro-5-(2-chlorophenyl)-2-(N-nitrosomethylamino)-3H-thieno[2,3-e][1,4]diazepine A mixture of 40 g. (0.123 m) of 7-chloro-5-(2-chlorophenyl)-2-(N-nitrosomethylamino)-3H-thieno[2,3-e][1,4]diazepine, 700 ml. of dichloromethane and 350 ml. of pyridine was cooled in an ice bath and nitrosyl chloride was bubbled in for 20 minutes with stirring. After 1 hour it was bubbled in for 5 minutes more and then 600 ml. of water was added slowly. The dichloromethane layer was separated, washed with 200 ml. of water, dried over anhydrous sodium sulfate and evaporated to dryness. The oil was dissolved in dichloromethane and filtered through 400 g. of Florisil. This was eluted with dichloromethane, and then ether. Crystallization of the dichloromethane fraction from a mixture of ether and petroleum ether gave product and more product was obtained from the ether fraction. A sample was recrystallized for analysis from a mixture of ether and petroleum ether to give yellow prisms, m.p. 104°–107°.

EXAMPLE 200

1,2-Dihydro-2-nitromethylene-5-phenyl-3H-thieno[3,2-e][1,4]diazepine 2-(N-nitrosomethylamino)-5-phenyl-3H-thieno[3,2-e][1,4]diazepine, 5.7 g. (0.02 m) was added to a mixture of 15 ml. of nitromethane, 4.5 g. of potassium t-butoxide and 60 ml. of dimethylformamide which had been stirred for 10 minutes at room temperature. Following addition, the reaction mixture was stirred under nitrogen and heated on the steam bath for 10 minutes. After acidification with 4 ml. of glacial acetic acid the mixture was partitioned between methylene chloride/toluene and saturated sodium bicarbonate solution. The organic layer was washed with water, dried and evaporated. Crystallization of the residue from methanol with seeding yielded product as yellow crystals, m.p. 160°–163°. Seeds were obtained by chromatographic purification over 30 fold amount of silica gel using 10% (v/v) of ethyl acetate in methylene chloride. The analytical sample was recrystallized from methanol, m.p. 163°–164°.

EXAMPLE 201

7-Chloro-2,3-dihydro-2-nitromethylene-5-phenyl-1H-thieno[2,3-e][1,4]diazepine

7-Chloro-2-(N-nitrosomethylamino)-5-phenyl-3H-thieno[2,3-e][1,4]diazepine, 3.2 g. (0.01 m), was added to a mixture of 10 ml. of nitromethane, 35 ml. of dimethylformamide and 2.26 g. (0.02 m) of potassium t-butoxide which had been stirred under nitrogen for 10 minutes at room temperature. After heating for 10 minutes on the steam bath the reaction mixture was acidified by addition of 2 ml. of glacial acetic acid and was partitioned between water and toluene. The toluene layer was washed with water, dried and evaporated. The residue crystallized from ethyl acetate/hexane to yield crude product. It was purified by chromatography over 40 g. of silica gel using 10% (v/v) of ethyl acetate in methylene chloride. The pure product was obtained as yellow crystals with m.p. 154°–156° C.

EXAMPLE 202

2-Aminomethyl-2,3-dihydro-5-phenyl-1H-thieno[3,2-e][1,4]diazepine dimaleate

A solution of 1.42 g. (5 mmol) of 1,2-dihydro-2-nitromethylene-5-phenyl-3H-thieno[3,2-e][1,4]diazepine in 200 ml. of ethanol was hydrogenated over Raney nickel (2 teaspoonful) for 1 hour at atmospheric pressure. The catalyst was removed by filtration and the filtrate was evaporated. The residue was treated with 1.2 g. of maleic acid in 10 ml. of 2-propanol. The salt was crystallized by addition of ether to yield product as yellow crystals with m.p. 170°–173°. The analytical sample was recrystallized from methanol/2-propanol, m.p. 187°–189°.

EXAMPLE 203

2-Aminomethyl-7-chloro-2,3-dihydro-5-phenyl-1H-thieno[2,3-e][1,4]diazepine dimaleate (A) A solution of 320 mg. (1 mmol) of 7-chloro-2,3-dihydro-2-nitromethylene-5-phenyl-1H-thieno[2,3-e][1,4]diazepine in 20 ml. of ethanol was hydrogenated over Raney nickel for 5 hours of atmospheric pressure. The catalyst was removed by filtration and the filtrate was evaporated. The residue was chromatographed over 7 g. of silica gel using methylene chloride, methanol, triethylamine in a ratio of 13:6:1. The fractions containing pure product were combined, evaporated and the residue was treated with maleic acid in 2-propanol. Crystallization of the dimaleate salt from 2-propanol/ether and recrystallization from ethyl acetate/ethanol yielded yellow crystals, m.p. 176°–177° C.

(B) A solution of 320 mg. (1 mmol) of 7-chloro-2,3-dihydro-2-nitromethylene-5-phenyl-1H-thieno[2,3-e][1,4]diazepine in 3 ml. of tetrahydrofuran was added to a suspension of 0.8 g. of lithium aluminum hydride in 20 ml. of tetrahydrofuran. After heating to reflux for 5 minutes, the reaction mixture was cooled and hydrolyzed by addition of 5 ml. of water. The inorganic material was separated by filtration and the filtrate was evaporated. The residue was chromatographed as described above the pure product was converted to the maleate to give dimaleate with m.p. 176°–178°.

EXAMPLE 204

1-Methyl-6phenyl-4H-imidazo[1,5-a]thieno[2,3-f]diazepine

2-Aminomethyl-2,3-dihydro-5-phenyl-1H-thieno[3,2-e][1,4]diazepine dimaleate, 1 g. (2 mmol), was partitioned between methylene chloride and aqueous ammonia. The methylene chloride layer was dried and evaporated. The residue was heated to reflux for 1 hour with 1 ml. of triethyl orthoacetate in 20 ml. of xylene. The solvent was evaporated under reduced pressure and the residue was crystallized from 2propanol/ether to yield 1-methyl-3a,4-dihydro-6-phenyl-3H-imidazo[1,5-a]thieno[2,3-f]diazepine with m.p. 150°–152°. This material was heated to reflux in 30 ml. of toluene with 2 g. of activated manganese dioxide for 2 hours. The manganese dioxide was filtered off and washed well with methylene chloride. The filtrate was evaporated and the residue was chromatographed over 7 g. of silica gel using 3% (v/v) of ethanol in methylene chloride. The fractions containing pure product were combined and evaporated. Crystallization from methylene chloride/ether and recrystallization from ethyl acetate/hexane yielded product with m.p. 223°–225°.

EXAMPLE 205

8-Chloro-1-methyl-6-phenyl-4H-imidazo[1,5-a]thieno[3,2-f][1,4]diazepine

2-Aminomethyl-7-chloro-2,3-dihydro-5-phenyl-1H-thieno[2,3-e][1,4]diazepine dimaleate, 0.52 g. (1 mmol) was partitioned between methylene chloride and aqueous ammonia. The methylene chloride solution was dried and evaporated. The residue was heated to reflux for 1 hour with 0.5 ml. of triethyl orthoacetate in 10 ml. of xylene. The crude product obtained after evaporation under reduced pressure was dissolved in 25 ml. of toluene and the solution was heated to reflux for 1½ hours after addition of 2.5 g. of activated manganese dioxide. The manganese dioxide was then filtered off and the filtrate was evaporated. The residue was chromatographed over 6 g. of silica gel using 4% (v/v) of ethanol in methylene chloride. Fractions containing the pure compound were combined and evaporated. Crystallization of the residue from ether/hexane yielded product with m.p. 168°–170° C.

EXAMPLE 206

7-Chloro-5-(2-chlorophenyl)-1,3-dihydro-2-dimethoxymalonylidene-2H-thieno[2,3-e][1,4]diazepine A mixture of 3.4 g. (0.03 m) of potassium t-butoxide, 7 ml. of dimethylmalonate and 20 ml. of dimethylformamide was stirred for 5 minutes under an atmosphere of nitrogen. Following the addition of 3.55 g. (0.01 m) of 7-chloro-5-(2-chlorophenyl)-2-(N-nitrosomethylamino)-3H-thieno[2,3-e][1,4]diazepine, the mixture was stirred and heated on the steambath for 5 minutes, was acidified by addition of 3 ml. of acetic acid an crystallized by slow addition of water. The precipitated material was collected, washed with water and methanol and dissolved in methylene chloride. The solution was dried and evaporated and the residue was crystallized from ethanol to yield pinkish crystals which were recrystallized from ethanol for analysis, m.p. 158°–160°.

EXAMPLE 207

7-Chloro-5-(2-chlorophenyl)-alpha-hydroxyimino-3H-thieno[2,3-e][1,4]diazepine-2-acetic acid, methyl ester A mixture of 2.15 g. (5 mmol) of 7-chloro-5-(2-chlorophenyl)-1,3-dihydro-2-dimethyoxymalonylidene-2H-thieno[2,3-e][1,4]diazepine, 50 ml. of methanol and 0.7 g. (1.25 mmol) of potassium hydroxide was heated to reflux under nitrogen for 3 hours. The solvent was partially evaporated and the residue was partitioned between methylene chloride and saturated sodium bicarbonate solution. The organic phase was dried and evaporated. The crude 7-chloro-5-)2-clorophenyl)-2,3-dihydro-2-(methoxycarbonylmethylene)-2H-thieno[2,3-e][1,4]diazepine obtained was dissolved in 20 ml. of glacial acetic acid. Sodium nitrite, 0.5 g., was added and the mixture was stirred for 15 minutes at room temperature, diluted with water and extracted with methylene chloride. The extracts were washed with water and sodium bicarbonate solution, dried and evaporated. Crystallization of the residue from methylene chloride/ether and recrystallization from tetrahydrofuran/methanol gave yellow crystals with m.p. 242°–245° dec.

EXAMPLE 208

Methyl 8-chloro-6-(2-chlorophenyl)-1-methyl-4H-imidazo[1,5-a]thieno[3,2-f][1,4]diazepine-3-carboxylate 7-Chloro-5-(2-chlorophenyl)-alpha-hydroxyimino-3H-thien[3,2-f][1,4]diazepine-2-acetic acid, methyl ester, 0.4 g. (1 mmol) was dissolved by warming in 30 ml. of tetrahydrofuran and 20 ml. of ethanol. Following the addition of Raney nickel (½ teaspoonful) the mixture was hydrogenated for 45 minutes at atmospheric pressure. The catalyst was filtered off and the filtrate was evaporated. The residue was dissolved in 10 ml. of methanol and treated with 0.4 ml. of triethyl orthoacetate and 3 drops of ethanolic hydrogen chloride. After heating to reflux for 10 minutes the solvent was evaporated and the residue was partitioned between methylene chloride and sodium bicarbonate solution. The organic layer was dried and evaporated. Chromatography of the residue over 10 g. of silica gel using methylene chloride/ethyl acetate 3:5 (v/v) and crystallization of the residue obtained after removal of the eluent from ethanol yielded product with m.p. 211°–212°.

EXAMPLE 209

8-Chloro-6-(2-chlorophenyl)-3-hydroxymethyl-1-methyl-4H-imidazo[1,5-a]thieno[3,2-f][1,4]diazepine To 20 ml. of ether under nitrogen was added 38 mg. (0.001 m) of lithium aluminum hydride. The reaction was cooled in an ice bath and 0.2 g. (0.000493 m) of methyl 8-chloro-6-(2-chlorophenyl)-1-methyl-4H-imidazo[1,5-a]thieno[3,2-f][1,4]diazepine-3-carboxylate was dissolved in 20 ml. of dry tetrahydrofuran and added dropwise with stirring to the reaction. After one hour 5 ml. of ethyl acetate was added followed by 3 ml. of a saturated solution of sodium bicarbonate. The reaction was filtered through Celite, which was then washed with dichloromethane and the combined filtrates were evaporated and crystallized from a mixture of dichloromethane and ether. Recrystallization from the same solvents gave off-white prisms, m.p. 100°–110° resets, m.p. 190°–194° C.

EXAMPLE 210

8-Chloro-6-(2-chlorophenyl)-1-methyl-4H-imidazo[1,5-a]thieno[3,2-f][1,4]diazepine-3-carboxylic acid To 10 ml. of methanol and 1 ml. of water was added 0.1 g. (0.000247 m) of methyl 8-chloro-6-(2-chlorophenyl)-1-methyl-4H-imidazo[1,5-a]thieno[3,2-f][1,4]diazepine-3-carboxylate and 0.028 g. (0.000493 m) of potassium hydroxide. The reaction was refluxed for 2 hours and evaporated. The residue was dissolved in 10 ml. of water, washed with 10 ml. of ether and then acidified with acetic acid. This was extracted with 30 ml. of dichloromethane, which was dried over anhydrous sodium sulfate, concentrated, cooled and filtered. Recrystallization of the precipitate from a mixture of dichlormethane and ether gave white prisms, m.p. 242°–247°.

EXAMPLE 211

8-Chloro-6-(2-chlorophenyl)-1-methyl-4H-imidazo[1,5-a]thieno[3,2-f][1,4]diazepine-3-carboxamide To 0.8 g. (0.00204 m) of 8-chloro-6-(2-chlorophenyl)-1-methyl-4H-imidazo[1,5-a]thieno[3,2-f][1,4]diazepine-3-carboxylic acid in 100 ml. of dry dichloromethane in an ice bath was added 0.46 g. (0.0022 m) of phosphorus pentachloride. After 30 minutes ammonia was bubbled in for 5 minutes with stirring. After 2 hours 75 ml. of water was added and the product was filered off. The dichloromethane was separated, dried and evaporated. The product obtained by crystallization of the residue from ethanol was combined with the first precipitate and recrystallized from a mixture of chloroform and ethanol to give white rods, m.p. 300°–305°.

EXAMPLE 212

Methyl 8-Chloro-6-(2-fluorophenyl)-1-phenyl-4H-imidazo[1,5-a][1,4]benzodiazepine-3-carboxylate A solution of 1.15 g. (2.5 mmol) of 2[(benzoylamino)-methoxy-carbonylmethylene]-7-chloro-5-(2-fluorophenyl)-1,3-dihydro-2H-1,4-benzodiazepine in 10 ml. of hexamethyl phosphoric triamide was heated to reflux for 10 minutes. The dark mixture was partitioned between water and ether/methylene chloride. The organic layer was washed with water, dried and evaporated. The residue was dissolved in methylene chloride and filtered over activated aluminum oxide with ethyl acetate. The filtrate was evaporated and chromatographed over 20 g. of silica gel using 10% (v/v) ethyl acetate in methylene chloride. Crystallization of the combined clean fractions from ether/hexane gave final product with mp 208°–209° C.

EXAMPLE 213

Methyl 8-chloro-6-(2-chlorophenyl)-1-phenyl-4H-imidazo[1,5-a][1,4]benzodiazepine-3-carboxylate A mixture of 375 mg. of 2-[(amino)methoxycarbonylmethylene]-7-chloro-5-(2-chlorophenyl)-1,3-dihydro-2H-1,4-benzodiazepine, 20 ml. of toluene and 0.5 ml. of benzaldehyde was heated to reflux for 10 minutes over molecular sieves 5A. Following the addition of 1 g. of activated manganese dioxide refluxing was continued for another 10 minutes. The mixture was filtered over Celite and the filtrate was evaporated. The crystalline residue was collected with ether and recrystallized from ethyl acetate/hexane to yield off-white crystals with m.p. 272°–275° C.

EXAMPLE 214

Ethyl 8-chloro-6-(2-chlorophenyl)-1-methyl-4H-imidazo[1,5-a][1,4]benzodiazepine-3-carboxylate-4-oxide A stirred solution of 12.4 g. (0.03 m) of ethyl 8-chloro-6-(2-chlorophenyl)-1-methyl-4H-imidazo[1,5-a][1,4]benzodiazepine-3-carboxylate in 200 ml. of methylene chloride was treated with 12 g. (0.07 m) of m-chloroperoxybenzoic acid in portions at room temperature. Stirring was continued for 2.5 hours. The solution was washed with 1 N sodium hydroxide solution and the turbid methylene chloride layer was separated, diluted with methanol and dried over sodium sulfate. Filtration and evaporation at reduced pressure gave a gum which gave off-white crystals when triturated with ether. An analytical sample was obtained after two recrystallizations from 1:1 ethanol-methylene chloride solution, m.p. 247°–249° C.

EXAMPLE 215

2-Methylamino-5-phenyl-3H-1,4-benzodiazepine

A solution of 23.6 g. (0.10 mole) of 1,3-dihydro-5-phenyl-2H-1,4-benzodiazepin-2-one in 1 liter of tetrahydrofuran (containing about 20 moles of monomethylamine) was chilled in an ice bath. To this mixture was added 14 ml. (d=1.73, 0.125 mole) of titanium tetrachloride in 200 ml. of benzene.

This mixture was stirred at room temperature for two days. The titanium complex was destroyed with 20 ml. of water. The inorganic salts that precipitated, were removed by filtration. The solvent was evaporated in vacuo, the residue was partitioned between methylene chloride and water. A colorless amorphous solid m.p. 227°–229° C. was removed by filtration. An additional sample, m.p. 226°–228° C. of a colorless solid was obtained from the methylene chloride mother liquors after drying over anhydrous sodium sulfate, evaporation to dryness, and crystallization from ethyl acetate.

An analytical sample was prepared by recrystallization from dimethylformamide to yield colorless prisms, m.p. 227°–229° C.

EXAMPLE 216

7-Ethyl-5-(2-fluorophenyl)-2-methylamino-3H-1,4-benzodiazepine

A solution of 56.4 g. (0.20 mole) of 1,3-dihydro-7-ethyl-5-(2-fluorophenyl)-2H-1,4-benzodiazepin-2-one in 2.0 l. of tetrahydrofuran containing 4 moles of monomethylamine was chilled in an ice bath. To this was added 33.0 ml. (0.30 mole) of titanium tetrachloride in 350 ml. of benzene. The mixture was stirred at room temperature for three days.

The titanium tetrachloride was decomposed with 100 ml. of water. The inorganic salts were removed by filtration. The filtrate was evaporated to dryness in vacuo. The residue was partitioned between methylene chloride and water. The methylene chloride layer was dried over anhydrous sodium sulfate, evaporated to dryness in vacuo. The residue on crystallization from acetonitrile yielded the amidine as light yellow prisms, m.p. 172°–174° C.

An analytical sample was prepared by recrystallization from acetonitrile to give light yellow prisms, m.p. 172°–174° C.

EXAMPLE 217

8-chloro-6-(2-fluorophenyl)-1-phenyl-4H-imidazo[1,5-a][1,4]benzodiazepine-3-carboxylic acid To a solution of 2.66 g (5.77 mmol) of methyl 8-chloro-6-(2-fluorophenyl)-1-phenyl-4H-imidazo[1,5-a][1,4]benzodiazepine-3-carboxylate in 50 ml of refluxing methanol was added a solution of 755 mg (11.5 mmol) of potassium hydroxide in 10 ml of water and the resulting mixture was heated for 2.5 hr. The solvent was removed in vacuo, the residue was dissolved in 50 ml of hot acetic acid and the solution was then poured into 100 ml of cold water. The product was collected, washed with water and air dried to give the title compound as an off-white solid. An analytical sample was recrystallized from benzene, mp 267°–269°.

EXAMPLE 218

8-chloro-6-(2-fluorophenyl)-1-phenyl-4H-imidazo[1,5-a][1,4]benzodiazepine

A suspension of 1.5 g (3.48 mmol) of 8-chloro-6-(2-fluorophenyl)-1-phenyl-4H-imidazo[1,5-a][1,4]benzodiazepine-3-carboxylic acid in 20 ml of mineral oil was stirred vigorously at 190° for ½ hr. The dark suspension was then slurried with hexane and extracted twice with 1 N hydrochloric acid. The acidic aqueous layer was then washed once with hexane and neutralized with 5% aqueous sodium carbonate. The precipitated product was collected and air dried; concentration of the filtrate gave an additional yield of the title compound as an off-white solid. An analytical sample was obtained by column chromatography on silica gel eluting with ethyl acetate, mp 241°–243°.

EXAMPLE 219

N,N-Dimethyl-[8-chloro-6-(2-fluorophenyl)-1-phenyl-4H-imidazo[1,5-a][1,4]benzodiazepine]-3-carboxamide A solution of 1.0 g (2.31 mmol) of 8-chloro-6-(2-fluorophenyl)-1-phenyl-4H-imidazo[1,5-a][1,4]benzodiazepine-3-carboxylic acid in 5 ml of thionyl chloride was refluxed for ½ hr., then cautiously added dropwise to 70 ml of cold 40% aqueous dimethylamine. The brown solid was collected, washed with water, dried and chromatographed on silica gel using ethyl acetate as the eluent to give the title compound as a brown foam. Recrystallization three times from acetone-water gave the analytical sample, mp 221°–223°.

EXAMPLE 220

8-chloro-6-(2-fluorophenyl)-1-phenyl-4H-imidazo[1,5-a][1,4]benzodiazepine-3-carboxamide A solution of 1.0 g (2.31 mmol) of 8-chloro-6-(2-fluorophenyl)-1-phenyl-4H-imidazo[1,5-a][1,4]benzodiazepine-3-carboxylic acid in 5 ml of thionyl chloride was refluxed for ½ hr., then cautiously added dropwise to 70 ml of cold ammonium hydroxide. The pink solid was collected, washed with water, air dried and chromatographed on silica gel using ethyl acetate as the eluent to give the title compound as a brown foam. Trituration with acetone gave the analytical sample as a white powder, mp 260°–262°.

EXAMPLE 221

2-chloro-13a-(2-fluorophenyl)-12,13a-dihydro-6-methyl-9H,11H-imidazo[1,5-a]oxazolo-[3,2-d][1,4]benzodiazepine A solution of 0.7 g (0.00203 m) of (2-fluorophenyl)-[2-[5-hydroxymethyl-2-methyl-1-imidazolyl)-5-chlorophenyl]methanone in 40 ml of dry dichloromethane was cooled in an ice bath and 0.22 ml (0.00227 m) of phosphorus tribromide was added with stirring. After 1 hr. at room temperature the mixture was cooled in an ice bath and 2 ml (0.0328 m) of ethanolamine was added. The solution was stirred for 2 hrs. at room temperature, refluxed for 1 hr. and then poured into 50 ml of water. The organic layer was separated, dried over anhydrous sodium sulfate, and concentrated to a small volume. The residue was developed on 4 silica gel thick layer plates in a solution of 5% methanol in ethyl acetate (v/v). The material corresponding to an Rf of 0.5 was removed from the plate and treated with methanol. The solution was filtered and the filtrates were evaporated.

The product was crystallized from ether. Recrystallization from a mixture of methanol and ether gave 0.1 g of the pure product as white prisms mp and mmp with an authentic sample 176°–181°.

EXAMPLE 222

Methyl 1-benzyl-8-chloro-6-(2-chlorophenyl)-4H-imidazo[1,5-a][1,4]benzodiazepine-3-carboxylate Phenylacetaldehyde, 2.4 g (0.02 m), was added to a solution of 3.8 g (0.01 m) of 2-[(amino)methoxycarbonylmethylene]-7-chloro-methylene chloride. Following the addition of 10 g of molecular sieves 5A the mixture was stirred at room temperature for 15 min and treated with 10 g of activated maganese dioxide for additional 15 min at room temperature. The inorganic material was separated by filtration over Celite. The filtrate was evaporated and the residue was crystallized from ether/hexane to yield colorless crystals with mp 155°–158°. The analytical sample was recrystallized from ethyl acetate/hexane, mp 160°–162°.

EXAMPLE 223

1-Benzyl-8-chloro-6-(2-chlorophenyl)-4H-imidazo[1,5-a][1,4]benzodiazepine-3-carboxamide A mixture of 2 g (4.2 mmol) of methyl 1-benzyl-8-chloro-6-(2-chlorophenyl)-4H-imidazo[1,5-a][1,4]benzodiazepine-3-carboxylate, 1 g of potassium hydroxide, 50 ml of methanol and 5 ml of water was heated to reflux for 4 hrs. under an atmosphere of nitrogen. The solvent was evaporated, the residue was dissolved in water and the solution was acidified with acetic acid. The precipitated crystals were collected, washed with water and dissolved in methylene chloride. The solution was dried and evaporated. Crystallization from methylene chloride/ethyl acetate yielded 1-benzyl-8-chloro-6-(2-chlorophenyl)-4H-imidazo[1,5-a][1,4]benzodiazepine-3-carboxylic acid with mp 305°–310° dec.

This material was suspended in 30 ml of methylene chloride. Phosphorus pentachloride, 0.8 g was added and the mixture was stirred over ice/water for 30 min. Ammonia gas was then introduced until the reaction mixture was alkaline. After stirring for 15 min at room temperature, aqueous ammonia was added and the two phase system was stirred for another 15 min. The methylene chloride phase was separated, dried and evaporated. The crystalline residue was recrystallized from ethyl acetate/methanol to yield colorless product with mp 282°–284°.

The analytical sample was chromatographed over silica gel (40 fold amount) using methylene chloride/ethyl acetate 1:1 (v/v) for elution, mp 286°–288°.

EXAMPLE 224

Preparation of 3-Ethyl-1,6-dihydro-1-methyl-7-methylamino-4-phenylpyrazolo[3,4-e][1,4]diazepine A solution of 6.8 g (0.0255 M) of 6,8-dihydro-3-ethyl-1-methyl-5-phenylpyrazolo[3,4-e][1,4]diazepin-7(1H)-one in 125 ml of dry tetrahydrofuran and 50 ml of dry benzene was cooled in an ice bath and methylamine was bubbled in until the solution was saturated. A solution of 6.3 g (0.0331 M) of titanium tetrachloride in 20 ml of benzene was then added dropwise with stirring and after 18 hr at room temperature the mixture was refluxed for 30 minutes. The solution was cooled, and treated with 4 g of ice. The reaction mixture was filtered and the precipitate was wasehd with tetrahydrofuran and then with dichloromethane. The combined filtrates were evaporated to dryness and the residue was crystallized from a mixture of methanol and ether, and recrystallized from a mixture of dichloromethane and ether to give the product as off-white prisms, mp 218°–221°.

EXAMPLE 225

Preparation of (3-Ethyl-1,6,7,8-tetrahydro-1-methyl-4-phenylpyrazolo[3,4-e][1,4]diazepin-7-ylidene)propanedioic acid, dimethyl ester A solution of 5.6 g (0.0199 M) of 3-ethyl-1,6-dihydro-1-methyl-7-methylamino-4-phenylpyrazolo[3,4-e][1,4]diazepine in 100 ml of dichloromethane and 50 ml of pyridine was stirred in an ice bath and nitrosyl chloride was bubbled in for 10 min. After 2 hr at room temperature, nitrosyl chloride was bubbled in for an additional 5 min. The mixture was allowed to stand for 30 min when it was poured into 200 ml of ice water. The organic layer was separated, washed with 100 ml of water, dried over anhydrous sodium sulfate, and filtered through 100 g of Florisil. The Florisil was thoroughly washed with ether, and the combined filtrates were evaporated to dryness. The intermediate N-nitroso derivative was not further purified but was used in the next step as follows.

A mixture of 14 ml of dimethyl malonate and 35 ml of N,N-dimethylformamide was treated with 6.5 g (0.0580 M) of potassium tertiary butoxide and after stirring for 5 min a solution of the N-nitroso compound prepared as described above in 10 ml of N,N-dimethylformamide was added. The resulting mixture was heated on the steam bath for 5 min, cooled, and 6 ml of glacial acetic acid was added. The reaction mixture was next poured into 300 ml of cold water, and after 15 min the solution was decanted. The remaining oil was dissolved in 75 ml of dichloromethane which was washed with 50 ml of dilute ammonium hydroxide, dried over anhydrous sodium sulfate and chromatographed through Florisil. The column was eluted first with dichloromethane, then with ether and finally with ethyl acetate. The ether and ethyl acetate fractions were combined and evaporated. The residue was crystallized and recrystallized from methanol to give the diester as off-white rods mp 145°–148°.

EXAMPLE 226

Preparation of 3-Ethyl-1,6-dihydro-α-hydroxyimino-1-methyl-4-phenylpyrazolo[3,4-e][1,4]diazepin-7-acetic acid, methyl ester A solution of 1.7 (0.00445 M) of (3-ethyl-1,6,7,8-tetrahydro-1-methyl-4-phenylpyrazolo[3,4-e][1,4]diazepin-7-ylidene) propanedioic acid, dimethyl ester in 40 ml of methanol was treated with n 0.56 g (0.01 M) of potassium hydroxide, and the solution was refluxed for 2.5 hr. The solvent was evaporated, and the residue was partitioned between 50 ml of dichloromethane and 30 ml of water. The water layer was first acidified with hydrochloric acid then made basic with ammonium hydroxide and extracted with 75 ml of dichloromethane. The organic layers were combined, dried over anhydrous sodium sulfate and filtered through Florisil. The Florisil was eluted with ether, and then with ether acetate. The eluents were combined and evaporated to give the crude monoester as an oil. This product was not further purified but was dissolved in 10 ml of glacial acetic acid and treated with 0.35 g (0.005 M) of sodium nitrite while stirring. After 45 min the reaction mixture was poured into 100 ml of water, which was extracted with 75 ml of dichloromethane. The organic layer was washed with 50 ml of dilute sodium bicarbonate solution, dried over anhydrous sodium sulfate and evaporated to dryness. The product was crystallized from a mixture of ethyl acetate and ether. Recrystallization from a mixture of dichloromethane and ether gave the pure material as off-white rods, mp 225°–227°.

EXAMPLE 227

Method A: Preparation of 7-Ethyl-1,9-dimethyl-6-phenyl-4H-9H-imidazo[1,5-a]pyrazolo[4,3-f][1,4]diazepin-3-carboxylic acid, methyl ester A solution of 0.35 g (0.000986 M) of 3-ethyl-1,6-dihydro-α-hydroxyimino-1-methyl-4-phenylpyrazolo[3,4-e][1,4]diazepin-7-acetic acid, methyl ester in 20 ml of dry tetrahydrofuran, and 25 ml of methanol was treated with 2 ml (0.0109 M) of triethylorthoacetate and 1 spatula of Raney nickel. The reaction mixture was hydrogenated at room temperature and atmospheric pressure for 2.5 hr. The catalyst was removed by filtration and the spent nickel was washed with methanol. The combined filtrates were evaporated and the residue was dissolved in 50 ml of dichloromethane. The solution was washed with 40 ml of dilute ammonium hydroxide, dried over anhydrous sodium sulfate, and evaporated to dryness. The residue was refluxed for 20 min in a solution of 50 ml of methanol, containing 2 ml (0.109 M) of triethylorthoacetate and 0.2 ml (0.00114 M) of 5.7 N ethanolic hydrogen chloride. Solvents were removed by evaporation under reduced pressure and the residue was dissolved in dichloromethane, which was then washed with dilute ammonium hydroxide, dried over anhydrous sodium sulfate and evaporated. The crude product, obtained in an oil was developed on three silica gel thick layer plates in a mixture of 5% methanol in ethyl acetate. The product which had an Rf of 0.5 was scraped off, stirred with methanol and filtered. The solution was evaporated, and the residue was crystallized from ether to give the pure product as white prisms, mp 186°–189°.

Method B:
7-Ethyl-1,9-dimethyl-6-phenyl-9H,9H-imidazo[1,5-a]pyrazolo[4,3-f][1,4]diazepine-3-carboxylic acid, methyl ester A stirred solution of 0.2 g (0.000567 M) of 3-ethyl-1,6-dihydro-α-hydroxyimino-1-methyl-4-phenyl-pyrazolo[3,4-e][1,4]diazepin-7-acetic acid, methyl ester in 10 ml of dichloromethane and 0.35 ml of acetic acid was treated with 0.4 g (0.0061 M) of zinc dust and stirring was continued for 5 min. The mixture was filtered, and the zinc was washed with dichloromethane and tetrahydrofuran. The combined filtrates were next treated with 0.3 ml (0.00164 M) of triethylorthoacetate. The mixture was evaporated under reduced pressure and the residue was heated under reflux for 1 min in a solution of 15 ml of ethyl acetate which contained 0.3 ml of triethylorthoacetate. The solution was evaporated and developed on 2 thick layer silica gel plates in a solution of ethyl acetate containing methanol (10%). The area having an Rf of 0.2–0.4 was scraped off and washed with methanol. The methanol solution was filtered and evaporated. Crystallization of the residue from ethyl acetate and recrystallization from a mixture of ethyl acetate and ether gave final product as white rods, m.p. 186°–189°.

EXAMPLE 228

8-Chloro-6-(2-chlorophenyl)-1,N,N-trimethyl-4H-imidazo[1,5-a]thieno-[3,2-f][1,4]diazepine-3-carboxamide Phosphorus pentachloride, 0.46 g (2.2 mmol), was added to a suspension of 0.785 g (2 mmol) of 8-chloro-6-(2-chlorophenyl)-1-methyl-4H-imidazo[1,5-a]thieno[3,2-f][1,4]diazepine-3-carboxylic acid in 50 ml of methylene chloride. After stirring under nitrogen in an ice bath for 30 min, dimethylamine was introduced until the reaction mixture was alkaline. It was stirred for 30 min at room temperature and washed with saturated sodium bicarbonate solution, dried and evaporated. Crystallization of the residue from ethyl acetate/ether gave off white crystals which were recrystallized from ethyl acetate for analysis, mp 197°–200°.

EXAMPLE 229

Ethyl 8-chloro-6-(2-fluorophenyl)-1-phenyl-4H-imidazo[1,5-a][1,4]benzodiazepine-3-carboxylate A solution of 4.15 g (20.1 mmol) of Ethyl 2-[phenylmethylene) amino]acetate,* N-oxide in 200 ml. of THF was cooled to −73° and 13.2 ml (21.2 mmol) of n-butyl lithium in hexane (MCB) was added slowly dropwise to give a light orange solution. After 15 min., a solution of 10.15 g (20 mmol) of 7-chloro-2-di(morpholino)phosphinyloxy-5-(2-fluorophenyl)-3H-1,4-benzodiazepine in 255 ml of THF was added slowly dropwise and the resulting dark brown suspension was allowed to warm to room temperature and stir overnight. The mixture was quenched with 3 ml of water and the solvent was removed in vacuo. The residue was diluted with 300 ml of water and extracted repeatedly with ether; the combined organic layers were washed twice with water, once with brine, dried with anhydrous magnesium sulfate and concentrated in vacuo to give the crude product as a light yellow solid. Recrystallization from aqueous acetone gave the product as a white crystalline solid.** Concentration of the mother liquor gave a further yield of final product.

* E. Buehler and G. B. Brown, *J. Org. Chem.*, 32, 265 (1967).
** m.p.—228°–230° C.

EXAMPLE 230

Methyl 8-chloro-6-(2-chlorophenyl)-1-(2-pyridyl)-4H-imidazo[1,5-a][1,4]benzodiazepine-3-carboxylate A mixture of 8.5 g (0.02 m) of 2-[(amino)methoxycarbonylmethylene]-7-chloro-5-(2-chlorophenyl)-1,3-dihydro-2H-1,4-benzodiazepine ethanolate, 200 ml of toluene, 4 ml of pyridine-2-carboxaldehyde and 15 g of molecular sieves 4A was heated to reflux for 10 min. Following addition of 20 g of activated manganese dioxide heating and stirring was continued for another 10 min. The mixture was filtered over Celite and the filtrate was evaporated. Crystallization of the residue from ethylacetate/ether yielded off-white crystals with mp 282°–285°. The analytical sample was recrystallized from methylene chloride/ethylacetate, mp 283°–285°.

EXAMPLE 231

Methyl 8-chloro-6-(2-chlorophenyl)-1-propyl-4H-imidazo[1,5-a][1,4]benzodiazepine-3-carboxylate A mixture of 4.5 g (0.0107 m) of 2-[(amino)methoxycarbonylmethylene]-7-chloro-5-(2-chlorophenyl)-1,3-dihydro-2H-1,4-benzodiazepine ethanolate, 100 ml of methylene chloride, 2 ml of butylaldehyde and 5 g of molecular sieves 5A was stirred at room temperature for 15 min. Activated manganese dioxide, 10 g, was then added and stirring was continued for additional 15 min. The mixture was filtered over Celite and the filtrate was evaporated. Crystallization of the residue from ether yielded a final product with mp 196°-198°. The analytical sample was recrystallized from ethylacetate/tetrahydrofuran/hexane, mp 197°-198°.

EXAMPLE 232

Methyl 8-chloro-6-(2-chlorophenyl)-1-isopropyl-4H-imidazo[1,5-a][1,4]benzodiazepine-3-carboxylate Following the procedure of Example 231, but substituting butylaldehyde by isobutylaldehyde gave a final product, crystallized from ether. For analysis it was recrystallized from ethylacetate/tetrahydrofuran/hexane, mp 234°-235°.

EXAMPLE 233

Methyl 8-chloro-1-chloromethyl-6-(2-chlorophenyl)-4H-imidazo[1,5-a][1,4]benzodiazepine-3-carboxylate A solution of chloroacetaldehyde, 5 ml, which was prepared by heating a mixture of 50 ml 2N hydrochloric acid and 50 ml of chloroacetaldehyde dimethylacetal for 30 min to reflux, was added to a solution of 4.5 g (0.0107 mol) of 2-[(amino)methoxycarbonylmethylene]-7-chloro-5-(2-chlorophenyl)-1,3-dihydro-2H-1,4-benzodiazepine ethanolate in 200 ml of methylene chloride. After stirring for 15 min, the reaction mixture was partitioned between methylene chloride and saturated aqueous sodium bicarbonate solution. The organic phase was dried and treated with 12 g of activated manganese dioxide. After stirring for 15 min at room temperature, the MnO$_2$ was separated by filtration over Celite and the filtrate was evaporated. Crystallization of the residue from methylene chloride/ether yielded the final product. The analytical sample was purified by chromatography over 30 fold amount of silica gel using methylene chloride/ethylacetate 7:3 (v/v). The pure product was crystallized from ether, mp 237°-239° dec.

EXAMPLE 234

Methyl 8-chloro-6-(2-chlorophenyl)-1-(2-dimethylaminoethyl)-4H-imidazo[1,5-a][1,4]benzodiazepine-3-carboxylate Dimethylamine, 5 ml, and 2 ml of acrolein were added to a solution of 4.5 g (0.0107 mol) of 2-[(amino)-methoxycarbonylmethylene]-7-chloro-5-(2-chlorophenyl)-1,3-dihydro-2H-1,4-benzodiazepine ethanolate in 100 ml of methylene chloride. After stirring for 10 min at room temperature, 12 g of activated manganese dioxide was added and stirring was continued for 15 min. The MnO$_2$ was removed by filtration over Celite and the filtrate was evaporated. Crystallization of the residue from ethanol/ether yielded final product which was recrystallized from ethylacetate/methanol/hexane for analysis, mp 203°-204°.

EXAMPLE 235

8-chloro-6-(2-chlorophenyl)-1-(2-pyridyl)-4H-imidazo[1,5-a][1,4]benzodiazepine-3-carboxylic acid A mixture of 4.3 g (0.009 mol) of methyl 8-chloro-6-(2-chlorophenyl)-1-(2-pydidyl)-4H-imidazo[1,5-a][1,4]benzodiazepine-3-carboxylate, 200 ml of methanol, 10 ml of water and 1.7 g (0.03 m) of potassium hydroxide was heated to reflux for 4 hrs. After partial evaporation of the solvent, the residue was acidified with glacial acetic acid and diluted with water. The precipitated product was collected, washed with water and dried to leave crystalline material which for analysis was recrystallized from methylene chloride/methanol/ethylacetate, mp 262°-265° dec.

EXAMPLE 236

8-chloro-6-(2-chlorophenyl)-1-(2-pyridyl)-4H-imidazo[1,5-a][1,4]benzodiazepine-3-carboxamide Phosphorus pentachloride, 3 g (0.0145 mol) was added to a suspension of 4 g (0.0089 mol) of 8-chloro-6-(2-chlorophenyl)-1-(2-pyridyl)-4H-imidazo[1,5-a][1,4]benzodiazepine-3-carboxylic acid in 250 ml of methylene chloride cooled by ice/water. After stirring for 30 min over ice/water, ammonia gas was introduced until the mixture showed alcaline reaction. Aqueous ammonia, 20 ml, and 200 ml of methylene chloride and then added and stirring was continued for 15 min. The organic layer was separated, dried over sodium sulfate and passed over a pad of silica gel using 5% (v/v) of ethanol in methylene chloride. The solution was evaporated and the residue was crystallized from ethanol/ethylacetate to yield off-white crystals which were recrystallized for analysis from methylene chloride/ethylacetate, mp 255°-257°, reset and melted again at 275°-278°.

EXAMPLE 237

8-chloro-6-(2-chlorophenyl)-1-propyl-4H-imidazo[1,5-a][1,4]benzodiazepine-3-carboxamide Reaction of 1.5 g (3.5 mmol) of methyl 8-chloro-6-(2-chlorophenyl)-1-propyl-4H-imidazo[1,5-a][1,4]benzodiazepine-3-carboxylate with 20 ml of methanolic ammonia yielded, under the conditions described in Example 238, a final product, crystallized from methylene chloride/ethanol, mp 298°-300°.

EXAMPLE 238

8-chloro-6-(2-chlorophenyl)-1-isopropyl-4H-imidazo[1,5-a][1,4]benzodiazepine-3-carboxamide A mixture of 1.3 g (3 mmol) of methyl 8-chloro-6-(2-chlorophenyl)-1-isopropyl-4H-imidazo[1,5-a][1,4]benzodiazepine-3-carboxylate and 20 ml of methanol containing 20% by weight of ammonia was heated in an autoclave at 130° for 20 hrs. The solvent was evaporated and the residue was crystallized from methylene chloride/ethanol to give the final product with mp 328°-330°. The analytical sample was recrystallized from the same solvents.

EXAMPLE 239

8-chloro-6-(2-chlorophenyl)-1-(2-dimethylaminoethyl)-4H-imidazo[1,5-a][1,4]benzodiazepine-3-carboxamide A mixture of 0.46 g of methyl 8-chloro-6-(2-chlorophenyl)-1-(2-dimethylaminoethyl)-4H-imidazo[1,5-a][1,4]benzodiazepine-3-carboxylate and 10 ml of methanol containing 20% of ammonia was heated in the bomb for 20 hours at 130°. The solvent was evaporated and the residue was chromatographed over silica gel (7 g) using 20% of ethanol in methylene chloride. Crystallization of the clean fractions from 2-propanol gave pure product with mp 249°–251°.

EXAMPLE 240

8-chloro-6-(2-chlorophenyl)-N-methyl-1-methylaminomethyl-4H-imidazo[1,5-a][1,4]benzodiazepine-3-carboxamide A solution of methylamine in tetrahydrofuran, 75 ml containing 20% methylamine, was added to a solution of 3 g (6.9 mmol) of methyl 8-chloro-1-chloromethyl-6-(2-chlorophenyl)-4H-imidazo [1,5-a][1,4]benzodiazepine-3-carboxylate in 50 ml of tetrahydrofuran. The mixture was heated to 100° for 118 hrs in a sealed vessel. The solvent was evaporated and the residue was crystallized from ethanol to yield final product which was purified by chromatography over 50 g of silica gel using 5% (v/v) of ethanol in methylene chloride. The combined clean fractions gave after evaporation and crystallization from methylene chloride/ethanol, product with mp 270°–273°.

EXAMPLE 241

Methyl 1-Aminomethyl-8-chloro-6-(2-chlorophenyl)-4H-imidazo[1,5-a][1,4]benzodiazepine-3-carboxylate, hydrochloride A solution of 2.4 g (5.4 mmol) of methyl 1-azidomethyl-8-chloro-6-(2-chlorophenyl)-4H-imidazo[1,5-a][1,4]benzodiazepine-3-carboxylate in 50 ml of tetrahydrofuran and 50 ml of ethanol was hydrogenated for 2 hrs at atmospheric pressure with Raney nickel as catalyst. The catalyst was removed by filtration and the filtrate was evaporated. The residue was dissolved in 2-propanol and the solution was treated with 5 mmol of ethanolic hydrogen chloride. The precipitated hydrochloride was collected and recrystallized from 2-propanol/methanol to yield product with mp 265°–270° dec. The analytical sample was recrystallized from the same solvents, mp 270°–275° dec.

EXAMPLE 242

Methyl 8-chloro-6-(2-chlorophenyl)-1-dimethylaminomethyl-4H-imidazo[1,5-a][1,4]benzodiazepine-3-carboxylate A mixture of 0.435 g (1 mmol) of methyl 8-chloro-1-chloromethyl-6-(2-chlorophenyl)-4H-imidazo[1,5-a][1,4]benzodiazepine-3-carboxylate, 15 ml of tetrahydrofuran and 1.5 ml of dimethylamine was heated in a sealed tube at 100° for 3 hours. The solvent was evaporated and the residue was partitioned between methylene chloride and aqueous sodium bicarbonate solution. The orgnic phase was dried and evaporated and the residue was crystallized from ether to yield final product. The analytical sample was recrystallized from ethylacetate/hexane mp 181°–183°.

EXAMPLE 243

Methyl 1-azidomethyl-8-chloro-6-(2-chlorophenyl)-4H-imidazo[1,5-a][1,4]benzodiazepine-3-carboxylate A mixture of 2.18 g (5 mmol) of methyl 8-chloro-1-chloromethyl-6-(2-chlorophenyl)-4H-imidazo[1,5-a][1,4]benzodiazepine-3-carboxylate, 0.65 g (10 mmol) of sodium azide and 30 ml of dimethylformamide was heated to reflux for 5 min. The product was precipitated by addition of water, was collected and dissolved in methylene chloride. The solution was dried and evaporated. Crystallization from ethylacetate/ether yielded colorless crystals with mp 187°–189°. The analytical sample was recrystallized from ethylacetate/hexane, mp 188°–190°.

EXAMPLE 244

Methyl 1-acetoxymethyl-8-chloro-6-(2-chlorophenyl)-4H-imidazo[1,5-a][1,4]benzodiazepine-3-carboxylate A mixture of 0.435 g (1 mmol) of methyl 8-chloro-1-chloromethyl-6-(2-chlorophenyl)-4H-imidazo[1,5-a][1,4]benzodiazepine-3-carboxylate, 0.5 g of sodium acetate and 20 ml of dimethyl formamide was heated to reflux for 10 min under an atmosphere of nitrogen. The solvent was removed under reduced pressure and the residue was partitioned between water and methylene chloride. The methylene chloride layer was dried and evaporated and the residue was chromatographed over 7 g of silica gel using 30% (v/v) of ethylacetate in methylene chloride. Crystallization of the combined clean fractions from ether yielded final product with mp 186°–188°. For analysis it was recrystallized from methylene chloride/ether/hexane.

EXAMPLE 245

1-Aminomethyl-8-chloro-6-(2-chlorophenyl)-4H-imidazo[1,5-a][1,4]benzodiazepine-3-carboxamide hydrochloride hemihydrate hemiisopropanolate A solution of 2 g (4.65 mmol) of 1-azidomethyl-8-chloro-6-(2-chlorophenyl)-4H-imidazo[1,5-a][1,4]benzodiazepine-3-carboxamide in 150 ml of tetrahydrofuran and 75 ml of ethanol was hydrogenated for 1½ hours at atmospheric pressure with Raney nickel as catalyst. The catalyst was separated by filtration and the filtrate was evaporated. Crystallization from ethanol/ether yielded final product with mp 230°–235° which was converted to the hydrochloride as follows: 1.2 g of the above base was dissolved in a mixture of hot ethanol and methanol. Ethanolic hydrogen chloride (3 mmol) was added. The mixture was concentrated and the hydrochloride was crystallized by addition of isopropanol and cooling. The crystals were collected, washed with 2-propanol and ether to leave product with mp 250°–260°. The analytical sample was recrystallized from methanol/2-propanol to give crystals which analyzed for a hemihydrate hemiisopropanolate, mp 250°–260° undefined.

EXAMPLE 246

8-chloro-6-(2-chlorophenyl)-1-dimethylaminoethyl-4H-imidazo[1,5-a][1,4]benzodiazepine-3-carboxamide A mixture of 0.44 g (1 mmol) of methyl 8-chloro-6-(2-chlorophenyl)-1-dimethylaminomethyl-4H-imidazo[1,5-a][1,4]benzodiazepine-3-carboxylate and 15 ml of methanol containing 20% of ammonia was heated for 16 hrs at 130° in an autoclave. The solvent was evaporated and the residue was crystallized from ethanol/ether to yield final product. The analytical sample was purified by passing over silica gel using methylene chloride/ethylacetate 1:1 (v/v) and crystallization from ethylacetate, mp 242°–245°.

EXAMPLE 247

1-Azidomethyl-8-chloro-6-(2-chlorophenyl)-4H-imidazo[1,5-a][1,4]benzodiazepine-3-carboxamide A mixture of 4.4 g (0.01 mol) of methyl 1-azidomethyl-8-chloro-6-(2-chlorophenyl)-4H-imidazo[1,5-a][1,4]benzodiazepine-3-carboxylate, 200 ml of methanol, 10 ml of water and 1.7 g (0.03 mol) of potassium hydroxide was heated to reflux for 3 hrs. After partial evaporation the mixture was acidified with glacial acetic acid and diluted with water. The precipitated product was collected and dissolved in methylene chloride. The solution was dried and evaporated and the residue was crystallized from methylene chloride/ethylacetate/hexane to yield 1-azidomethyl-8-chloro-6-(2-chlorophenyl)-4H-imidazo[1,5-a][1,4]benzodiazepine-3-carboxylic acid which was converted to the amide as follows: Phosphorus pentachloride 2.1 g (0.01 mol) was added to a suspension of the above material in 200 ml of methylene chloride and the mixture was stirred in ice-water for 20 min. A stream of ammonia was then introduced until the reaction mixture was alcaline. After stirring for an additional 15 min, aqueous ammonia was added and stirring was continued for 1 hr at room temperature. The mixture was diluted with methylene chloride and washed with saturated sodium chloride solution. The organic phase was dried and evaporated. The residue was chromatographed over 120 g of silica gel using 2.5% (v/v) of ethanol in methylene chloride. The clean fractions were combined and evaporated and the residue was crystallized from ethanol to yield final product with mp 258°–260° dec. The analytical sample was recrystallized from methylene chloride/ethylacetate.

EXAMPLE 248

Methyl 8-chloro-6-phenyl-4H-imidazo[1,5-a][1,4]benzodiazepine-3-carboxylate

Raney nickel, 2 teaspoonsful, was added to a solution of 10 g (0.028 mol) of 7-chloro-alpha-hydroximino-5-phenyl-3H-1,4-benzodiazepine-2-acetic acid, methyl ester in a mixture of 200 ml of methanol and 200 ml of tetrahydrofuran. The mixture was hydrogenated at atmospheric pressure for 5 hrs. The catalyst was separated by filtration over Celite and the filtrate was evaporated to dryness. The residue was dissolved in 100 ml of methanol and the solution was treated with 10 ml of triethyl orthoformate and 5 ml of ethanolic hydrogen chloride. After refluxing the mixture for 10 min the solvent was evaporated under reduced pressure and the residue was partitioned between methylene chloride and saturated aqueous sodium bicarbonate solution. The organic phase was dried and evaporated. Crystallization of the residue from ether yielded final product which was recrystallized from methylene chloride/ether for analysis, mp 235°–236°.

EXAMPLE 249

Methyl 8-chloro-6-(2-chlorophenyl)-4H-imidazo[1,5-a][1,4]benzodiazepine-3-carboxylate A mixture of 9 g of 2-[(amino)methoxycarbonyl methylene]-7-chloro-5-(2-chlorophenyl)-1,3-dihydro-2H-1,4-benzodiazepine ethanolate, 100 ml of toluene and 20 ml of triethyl orthoformate was heated to reflux for 15 min. The solvent was evaporated under reduced pressure and the crystalline residue was collected with ether and recrystallized from ethylacetate/methanol to yield final product with mp 206°–208°.

EXAMPLE 250

8-chloro-6-phenyl-4H-imidazo[1,5-a][1,4]benzodiazepine-3-carboxamide

A mixture of 5 g of methyl 8-chloro-6-phenyl-4H-imidazo[1,5-a][1,4]benzodiazepine-3-carboxylate and 100 ml of methanol containing 20% of ammonia was heated to 130° in an autoclave for 8 hrs. The precipitated crystals were collected and recrystallized from tetrahydrofuran/methanol to yield final product with mp 295°–296°. The analytical sample was recrystallized from dimethylformamide/ether, mp 296°–297°.

EXAMPLE 251

8-chloro-6-(2-fluorophenyl)-4H-imidazo[1,5-a][1,4]benzodiazepine-3-carboxamide

Phosphorus pentachloride, 2.6 g (0.0125 m) was added to a suspension of 3.55 g (0.01 m) of 8-chloro-6-(2-fluorophenyl)-4H-imidazo[1,5-a][1,4]benzodiazepine-3-carboxylic acid in 200 ml of methylene chloride cooled with ice/water. After stirring for 30 min ammonia gas was introduced until the reaction mixture was alkaline. After additional 15 min aqueous ammonia was added and stirring was continued for 30 min. The reaction mixture was then partitioned between water and methylene chloride containing 10% (v/v) of ethanol. The organic phase was dried and passed over a pad of silica gel. The solution was evaporated and the solid residue was recrystallized from ethanol to yield the final product. The analytical sample was recrystallized from tetrahydrofuran/ethanol, mp 292°–294°.

EXAMPLE 252

8-chloro-6-(2-chlorophenyl)-4H-imidazo[1,5-a][1,4]benzodiazepine-3carboxamide

A mixture of 5 g (0.013 mol) of methyl 8-chloro-6-(2-chlorophenyl)-4H-imidazo[1,5-a][1,4]benzodiazepine-3-carboxylate and 75 ml of methanol containing 20% of ammonia was heated in an autoclave at 130° for 18 hrs. The reaction mixture from which the product had crystallized was heated in methanol/methylene chloride until solution was complete. Filtration and concentration yielded the final product with mp >300°. The analytical sample was recrystallized from methylene chloride/ethanol.

EXAMPLE 253

8-chloro-N,N-dimethyl-6-phenyl-4H-imidazo[1,5-a][1,4]benzodiazepine-3-carboxamide A mixture of 5 g (0.014 mol) of methyl 8-chloro-6-phenyl-4H-imidazo[1,5-a][1,4]benzodiazepine-3-carboxylate, 2.4 g (0.043 mol) of potassium hydroxide, 10 ml of water and 140 ml of methanol heated to reflux for 6 hrs. The solvent was evaporated and the residue was dissolved in water. The solution was filtered and acidified with glacial acetic acid. The precipitated crystals were collected and crystallized from methylene chloride/ethanol to give 8-chloro-6-phenyl-4H-imidazo[1,5-a][1,4]benzodiazepine-3-carboxylic acid with mp 268°-270°.

1 g of this acid was stirred with 1.3 g of phosphorus pentachloride and 100 ml of methylene chloride at room temperature for 2 hrs. Dimethylamine was bubbled into the mixture with cooling until a clear solution with basic pH resulted. The solution was then washed with sodium chloride solution and water. The methylene chloride layer was dried and evaporated.

Crystallization of the residue from ether yielded the final product which was recrystallized from methylene chloride/ethylacetate for analysis, mp 231°-233°.

EXAMPLE 254

8-chloro-6-(2-chlorophenyl)-N,N-dimethyl-4H-imidazo[1,5-a][1,4]benzodiazepine-3-carboxamide A mixture of 2 g of methyl 8-chloro-6-(2-chlorophenyl)-4H-imidazo[1,5-a][1,4]benzodiazepine-3-carboxylate, 15 ml of hexamethyl phosphoric triamide and 1.5 g of lithium chloride was heated to 225°. The cooled reaction mixture was partitioned between water and methylene chloride/ether. The organic phase was washed with aqueous bicarbonate solution, was dried and evaporated. Crystallization from ether yielded the final product which was recrystallized from ethylacetate/methanol for analysis, mp 240°-242°.

EXAMPLE 255

8-chloro-6-(2-chlorophenyl)-3-hydroxymethyl-4H-imidazo[1,5-a][1,4]benzodiazepine isopropanolate A solution of 25 g (0.065 mol) of methyl 8-chloro-6-(2-chlorophenyl)-4H-imidazo[1,5-a][1,4]benzodiazepine-3-carboxylate in 250 ml of tetrahydrofuran was added at −10° to a suspension of 5 g of lithium aluminum hydride in 200 ml of ether. After addition the mixture was stirred between −5° and 0° for 15 min. The mixture was then hydrolized by addition of 25 ml of water. The inorganic material was separated by filtration over Celite and the filtrate was dried and evaporated. Crystallization of the residue from methylene chloride/ether/ethylacetate yielded the solvated product. Recrystallization from 2-propanol/ether gave a solvate with mp 103°-105° dec. which according to analytical and spectral data contained 1 mol of isopropanol.

EXAMPLE 256

8-chloro-6-(2-chlorohenyl)-4H-imidazo[1,5-a][1,4]benzodiazepine-3carboxaldehyde

A mixture of 0.5 g of 8-chloro-6-(2-chlorophenyl)-3-hydroxymethyl-4H-imidazo[1,5-a][1,4]benzodiazepine isopropanolate, 40 ml of methylene chloride and 2.5 g of activated manganese dioxide was stirred at room temperature for 2 hrs. The $MnO_2$ was removed by filtration over Celite and the filtrate was evaporated. Crystallization of the residue from ether gave the final product with mp 213°-215°.

EXAMPLE 257

8-chloro-3-chloromethyl-6-(2-chlorophenyl)-4H-imidazo[1,5-a][1,4]benzodiazepine

Crude 8-chloro-6-(2-chlorophenyl)-3-hydroxymethyl-4H-imidazo-[1,5-a][1,4]benzodiazepine, 6 g, was added slowly to 30 ml of thionyl chloride. Following addition the mixture was stirred for 15 min at room temperature and then gradually diluted with 100 ml of ethylacetate. The precipitate crystals were collected after 15 min and partitioned between methylene chloride and saturated aqueous sodium bicarbonate solution. The methylene chloride layer was dried and evaporated. Crystallization from methylene chloride/ether yielded the final product. The analytical sample was purified by passing over silica gel using 10° (v/v) of ethylacetate in methylene chloride followed by crystallization from ether, mp ca. 165°. The crystals do not melt upon slow heating but on immersion at about 165°.

EXAMPLE 258

3-acetyl-8-chloro-6-(2-chlorophenyl)-4H-imidazo[1,5-a][1,4]benzodiazepine

A solution of 2.8 g (7.8 mmol) of 8-chloro-6-(2-chlorophenyl)-4H-imidazo[1,5-a][1,4]benzodiazepine-3-carboxaldehyde in 150 ml of tetrahydrofuran was added to 50 ml of a 1 molar solution of methyl magnesium iodide in ether. After stirring for 15 min at room temperature the reaction mixture was hydrolysed by addition of water, diluted with tetrahydrofuran dried over sodium sulfate and filtered over Celite. The filtrate was evaporated and the residue was chromatographed over 60 g of silica gel using 5% (v/v) of ethanol in methylene chloride. The clean fractions containing 8-chloro-6-(2-chlorophenyl)-3-(1-hydroxyethyl)-4H-imidazo[1,5-a][1,4]benzodiazepine were combined and evaporated. The residue was dissolved in 100 ml of methylene chloride and stirred for 2 hrs at room temperature after addition of 15 g of activated manganese dioxide. The $MnO_2$ was removed by filtration over Celite and the filtrate was evaporated. The residue was again purified by chromatography over 30 g of silica gel using 10% (v/v) of ethylacetate in methylene chloride. Crystallization of the combined clean fractions from ethylacetate/hexane gave the final product with mp 214°-216°.

EXAMPLE 259

8-Chloro-6-(2-chlorophenyl)-3-methoxymethyl-4H-imidazo[1,5-a][1,4]benzodiazepine A mixture of 2.7 g (7.15 mmol) of 8-chloro-3-chloromethyl-6-(2-chlorophenyl)-4H-imidazo[1,5-a][1,4]benzodiazepine, 50 ml of methanol and 3 ml of triethylamine was heated to reflux for 20 min. The solvent was evaporated and the residue was partitioned between methylene chloride and 10% aqueous sodium carbonate solution. The methylene chloride layer was dried and evaporated and the residue was dissolved in 2-propanol and treated with ethanolic hydrogen chloride. The crystalline dihydrochloride with mp >230° dec. which precipitated was collected and partitioned between methylene chloride and aqueous sodium carbonate solution. The organic phase was dried and evaporated and the residue was crystallized from ether/hexane to yield final product with mp 126°-130°. The analytical sample was recrystallized from ether.

EXAMPLE 260

8-chloro-6-phenyl-1,N,N-trimethyl-4H-imidazo[1,5-a][1,4]benzodiazepine-3-carboxamide A mixture of 1.5 g (4.2 mmol) of 8-chloro-1-methyl-6-phenyl-4H-imidazo[1,5-a][1,4]benzodiazepine-3-carboxylic acid, 1.7 g (8 mmol) of phosphorus pentachloride and 100 ml of methylene chloride was stirred under argon for 3 hrs. Dimethylamine was introduced at room temperature until a clear solution with basic pH resulted. The solution was washed with water, dried and evaporated. Crystallization of the residue from ethylacetate/ether/hexane and recrystallization from ether gave final product with mp 173°–175°.

EXAMPLE 261

8-chloro-6-(2-fluorophenyl)-1-methyl-N-phenyl-4H-imidazo[1,5-a][1,4]benzodiazepine-3-carboxamide Phosphorus pentachloride, 1.3 g (6.25 mmol) was added to a suspension of 1.9 g (5 mmol) of 8-chloro-6-(2-fluorophenyl)-1-methyl-4H-imidazo[1,5-a][1,4]benzodiazepine-3-carboxylic acid in 100 ml of methylene chloride. After stirring for 30 min with cooling over ice/water, 7 ml of aniline was added and stirring was continued for 30 min at room temperature. The reaction mixture was partitioned between 10% aqueous sodium carbonate solution and methylene chloride. The organic layer was dried and evaporated. Crystallization of the residue from ether and recrystallization from methylene chloride/ethanol gave a final product which was recrystallized from tetrahydrofuran/ethanol for analysis, mp 228°–288°.

EXAMPLE 262

8-chloro-N-cyclopropyl-6-(2-fluorophenyl)-1-methyl-4H-imidazo[1,5-a][1,4]benzodiazepine-3-carboxamide Phosphorus pentachloride, 1.3 g (6.25 mmol) was added to a suspension of 1.9 g (5.1 mmol) of 8-chloro-6-(2-fluorophenyl)-1-methyl-4H-imidazo[1,5-a][1,4]benzodiazepine-3-carboxylic acid in 100 ml of methylene chloride. After stirring for 30 min over ice/water 3 ml of cyclopropylamine was added and stirring was continued for 10 min. The reaction mixture was washed with aqueous sodium carbonate solution, dried and evaporated. The residue was passed over a pad of silica gel using 10% (v/v) of ethanol in methylene chloride. Crystallization of the product from ethylacetate/hexane yielded final product as crystals with mp 196°–197°.

EXAMPLE 263

8-chloro-6-(2-chlorophenyl)-1,N,N-trimethyl-4H-imidazo[1,5-a][1,4]benzodiazepine-3-carboxamide A stirred suspension of 3.6 g (0.0093 mole) of 8-chloro-6-(2-chlorophenyl)-1-methyl-4H-imidazo[1,5-a][1,4]benzodiazepine-3-carboxylic acid in 75 ml of dichloromethane was cooled in an ice bath and treated with 2.1 g (0.01 mole) of phosphorus pentachloride in portions. The reaction was protected by a drying tube and stirring in the cold was continued 30 min. longer. With continued cooling dimethylamine was bubbled into the solution for 5 minutes and stirring was continued for an additional 30 min. The mixture was evaporated at reduced pressure to dryness. The gummy residue was stirred with water and basified with ammonium hydroxide. Extraction with methylene chloride followed by drying and evaporation in vacuo gave a tan foam. The foam was dissolved in 600 ml of boiling ether and filtered to remove some insoluble material. After concentrating the filtrate on a steam bath to about 250 ml, it was filtered again. Further concentration to about 100 ml with occasional scratching initiated crystallization. The flask was removed from the heat and cooled at room temperature overnight. The off-white prisms were filtered, washed with ether and air dried on the funnel to final product with mp 225°–230°. Recrystallization of a sample from benzene-ether raised the melting point to 228°–232°.

EXAMPLE 264

8-chloro-5,6-dihydro-6-(2-fluorophenyl)-1-methyl-4H-imidazo[1,5-a][1,4]benzodiazepine-3-carboxylic acid, 2,2-dimethylhydrazide A mixture of 1.2 g (2.9 mmol) of 8-chloro-6-(2-fluorophenyl)-1-methyl-4H-imidazo[1,5-a][1,4]benzodiazepine-3-carboxylic acid, 2,2-dimethylhydrazide, 50 ml of methylene chloride, 5 ml of glacial acetic acid and 2.5 g of zinc dust was stirred at room temperature for 2 hrs. The inorganic material was separated. The filtrate was washed with sodium carbonate solution, dried and evaporated. The residue was crystallized from ethylacetate/ether to yield a final product which was recrystallized from ethylacetate for analysis, mp 218°–219°.

EXAMPLE 265

8-chloro-6-(2-chlorophenyl)-5,6-dihydro-1-methyl-4H-imidazo[1,5-a][1,4]benzodiazepine-3-carboxamide A stirred solution of 7 g (0.018 mole) of 8-chloro-6-(2-chlorophenyl)-1-methyl-4H-imidazo[1,5-a][1,4]benzodiazepine-3-carboxamide in 70 ml of glacial acetic acid was treated with 5.6 g (0.087 g. atm.) of zinc dust in portions. The stirred mixture was heated under argon in an oil bath at 110° for 5 hrs. After cooling to room temperature the mixture was filtered and the solid was washed with methylene chloride. The filtrate was concentrated at reduced pressure at 60° to remove methylene chloride and the residue was poured into cold water and basified with ice cold ammonia. The resulting white solid was filtered, washed with water and partially dried on the funnel. Treatment of the damp solid with 200 ml of 1 N hydrochloric acid by stirring for 5 min and then filtering gave about 3 g of unreacted material as a white solid. When the filtrate was basified with cold, dilute ammonium hydroxide a white solid separated which was collected by filtration, washed with water and air dried on the funnel to give final product.

Recrystallization from ethanol-methylene chloride gave white plates, m.p. 298°–305° dec.

EXAMPLE 266

8-chloro-6-(2-chlorophenyl)-5,6-dihydro-1-methyl-4H-imidazo[1,5-a][1,4]benzodiazepine-3-carboxamide hydrochloride 1⅓ hydrate A suspension of 1.3 g (0.0034 mole) of the base of Example 265 in 75 ml of 95% ethanol was treated with 10 ml of a 5.7 N solution of hydrogen chloride in ethanol and boiled on a steam bath to give a clear solution. The solution was filtered and kept at room temperature overnight. White needles had separated. The product was filtered, washed with ethanol and air dried to give final product, mp 310°–315° dec. after changing to prisms at ca. 250°. Another amount of product, mp

127

305°–310° dec. was obtained by concentrating the mother liquor.

EXAMPLE 267

8-chloro-6-(2-fluorophenyl)-1-methyl-4H-imidazo[1,5-a][1,4]benzodiazepine, and
8-chloro-6-(2-fluorophenyl)-1-methyl-6H-imidazo[1,5-a][1,4]benzodiazepine A solution of 185 mg of 8-chloro-6-(2-fluorophenyl)-1-methyl-4H-imidazo[1,5-a][1,4]benzodiazepine-3-carboxylic acid in 5 ml of ethylene glycol was heated to reflux for 1 hr under an atmosphere of nitrogen. The cooled reaction mixture was partitioned between ether/toluene and saturated sodium bicarbonate solution. The organic phase was separated, dried and evaporated. The residue was chromatographed over 7 g of silica gel using 3% (v/v) of ethanol in methylene chloride to yield both the less polar 8-chloro-6-(2-fluorophenyl)-1-methyl-6H-imidazo[1,5-a][1,4]benzodiazepine with mp 177°–179° and 8-chloro-6-(2-fluorophenyl)-1-methyl-4H-imidazo[1,5-a][1,4]benzodiazepine with mp 151°–153°.

EXAMPLE 268

8-chloro-6-(2-chlorophenyl)-1,3-dimethyl-4H-imidazo[1,5-a][1,4]benzodiazepine

Raney nickel, 40 g, was added to a solution of 3.9 g (0.01 m) of 8-chloro-3-chloromethyl-6-(2-chlorophenyl)-1-methyl-4H-imidazo[1,5-a][1,4]benzodiazepine in 125 ml of dry tetrahydrofuran. After stirring at room temperature for 15 min the nickel was separated by filtration over Celite and the filtrate was evaporated. Crystallization of the residue from ether/hexane yielded crystals with mp 175°–177°. The analytical sample was recrystallized from methylene chloride/hexane and had the same mp.

EXAMPLE 269

8-chloro-6-(2-chlorophenyl)-1-methyl-4H-imidazo[1,5-a][1,4]benzodiazepine-3-acetic acid, ethyl ester A mixture of 0.38 g (1 mmol) of 8-chloro-6-(2-chlorophenyl)-3-cyanomethyl-1-methyl-4H-imidazo[1,5-a][1,4]benzodiazepine and 10 ml of ethanol containing 10% of hydrogen chloride was heated to reflux for 30 min. The reaction mixture was then partitioned between methylene chloride and 10% aqueous sodium carbonate solution. The organic phase was dried and evaporated and the residue was crystallized from ether/hexane to yield product with mp 143°–154°. The analytical sample was recrystallized from ethanol/hexane and had the same mp.

EXAMPLE 270

8-chloro-6-(2-chlorophenyl)-3-(2-hydroxyethyl)-1-methyl-4H-imidazo[1,5-a][1,4]benzodiazepine A solution of 0.43 g (1 mmol) of 8-chloro-6-(2-chlorophenyl)-1-methyl-4H-imidazo[1,5-a][1,4]benzodiazepine-3-acetic acid, ethyl ester in 10 ml of tetrahydrofuran was added to a suspension of 0.3 g of lithium aluminum hydride in 30 ml of ether cooled to −10°. Following the addition the mixture was stirred at 0° to 5° for 10 min and then hydrolysed by addition of water. The inorganic material was separated by filtration and washed with methylene chloride. The filtrate was dried and evaporated. Crystallization of the residue from ethyl acetate/ether yielded product, which was further purified by chromatography over 5 g of silica gel using 5% (v/v) of ethanol in methylene chloride and crystallized from ethyl acetate/hexane, mp 170°–171°.

We claim:

1. A process to produce a compound of the formula

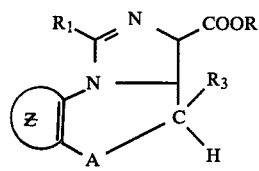

wherein A is

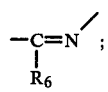

$R_1$ is selected from the group consisting of hydrogen, lower alkyl, alkoxy lower alkyl, halo lower alkyl; R is hydrogen or lower alkyl; $R_3$ is selected from the group consisting of hydrogen and lower akyl; $R_4$ is selected from the group consisting of hydrogen, halogen, cyano, trifluoromethyl, lower alkyl, mono- or di-$C_1$ to $C_7$ alkyl or phenyl, chlorophenyl or tolyl substituted amino, amino, hydroxy lower alkyl and lower alkanoyl; $R_6$ is selected from the group consisting of phenyl, mono-halo or mono-nitro substituted phenyl, di-halo or halo-nitro substituted phenyl, pyridyl and mono-halo or mono-nitro substituted pyridyl; and

is selected from the group consisting of

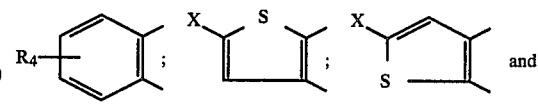

| wherein X is chlorine, bromine, iodine or hydrogen | wherein X is chlorine, bromine, iodine or hydrogen |

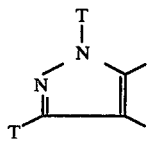

wherein T is hydrogen or lower alkyl which comprises the stepwise reaction of a compound of the formula

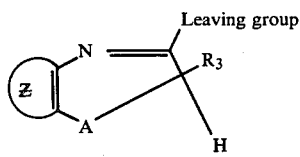

wherein $R_3$, $R_4$, $R_6$, A and

are as above and the leaving group is selected from the group consisting of alkoxides, alkylthio, halo, cyano, phosphate and nitrosoalkylamino (a) with the anion generated from malonic ester, i.e., a compound of the formula

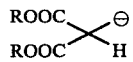

wherein R is lower alkyl;

(b) decarboxylating with an alkali metal hydroxide the product of (a);
(c) nitrosating with nitrous acid the product of (b);
(d) reducing with $H_2$/Raney nickel or zinc/acetic acid the product of (c);
(e) reacting the product of (d) with an alkanoic acid ortho ester of the formula $R_1C(OR)_3$ wherein R is lower alkyl and $R_1$ is selected from the group consisting of hydrogen, lower alkyl, alkoxy lower alkyl, halo lower alkyl, to produce the final product as an ester, i.e., R=lower alkyl;
(f) if desired, hydrolysing with alkali metal hydroxides the product of (e) to the final product as as acid, i.e., R=hydrogen.

* * * * *